US012685760B2

(12) United States Patent
Emmerich et al.

(10) Patent No.: US 12,685,760 B2
(45) Date of Patent: Jul. 21, 2026

(54) IL2 MUTEINS

(71) Applicant: Synthekine, Inc., Menlo Park, CA (US)

(72) Inventors: Jan Emmerich, Menlo Park, CA (US); Steve Kauder, Menlo Park, CA (US); Scott Alan McCauley, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 888 days.

(21) Appl. No.: 17/785,786

(22) PCT Filed: Jan. 14, 2021

(86) PCT No.: PCT/US2021/013514

§ 371 (c)(1),
(2) Date: Jun. 15, 2022

(87) PCT Pub. No.: WO2021/146481

PCT Pub. Date: Jul. 22, 2021

(65) Prior Publication Data

US 2023/0210951 A1 Jul. 6, 2023

Related U.S. Application Data

(60) Provisional application No. 62/960,847, filed on Jan. 14, 2020.

(51) Int. Cl.
*A61K 38/20* (2006.01)
*A61K 45/06* (2006.01)
*A61P 37/00* (2006.01)

(52) U.S. Cl.
CPC .......... *A61K 38/2013* (2013.01); *A61K 45/06* (2013.01); *A61P 37/00* (2018.01)

(58) Field of Classification Search
CPC ..... C07K 14/55; C12N 15/62; A61K 38/2013
See application file for complete search history.

(56) References Cited

U.S. PATENT DOCUMENTS 4,766,106 A 8/1988 Katre et al.
8,012,465 B2 9/2011 Elias et al.
9,567,399 B1 2/2017 Campbell et al.
9,861,705 B2 1/2018 Bossard et al.
10,010,587 B2 7/2018 Addepalli et al.
10,086,046 B2 10/2018 Paulsen et al.
10,150,802 B2 12/2018 Garcia et al.
11,491,205 B2 11/2022 Emmerich et al.
2003/0166163 A1 9/2003 Gillies
2004/0136952 A1 7/2004 Bhaskaran et al.
2004/0175357 A1 9/2004 Shanafelt et al.
2006/0269515 A1 11/2006 Denis-Mize et al.
2006/0292116 A1 12/2006 Epstein et al.
2010/0028350 A1* 2/2010 Jevnikar ............ A61K 31/7105
424/139.1
2013/0195795 A1* 8/2013 Gavin ..................... A61P 11/06
435/375
2014/0046026 A1 2/2014 Garcia et al.
2014/0328791 A1 11/2014 Bossard et al.
2017/0015722 A1 1/2017 Garcia et al.
2018/0016316 A1 1/2018 Garcia et al.
2018/0125941 A1 5/2018 Greve
2019/0119346 A1 4/2019 Garcia et al.
2020/0299349 A1 9/2020 Garcia et al.
2021/0269498 A1 9/2021 Emmerich et al.
2021/0275641 A1 9/2021 Emmerich et al.
2023/0031597 A1 2/2023 Emmerich et al.
2024/0400631 A1 12/2024 Emmerich et al.

FOREIGN PATENT DOCUMENTS

| | | | |
|---|---|---|---|
| CN | 106659757 | A | 5/2017 |
| JP | 2002515247 | A | 5/2002 |
| JP | 2005507870 | A | 3/2005 |
| JP | 2006519170 | A | 8/2006 |
| JP | 2012046552 | A | 3/2012 |
| JP | 201 4502967 | A | 2/2014 |
| JP | 2017518361 | A | 7/2017 |
| KR | 20010043602 | A | 5/2001 |
| KR | 20070003934 | A | 1/2007 |
| RU | 2531936 | C2 | 10/2014 |
| WO | 9960128 | A1 | 11/1999 |
| WO | 2005086751 | A2 | 9/2005 |
| WO | 2008156712 | A1 | 12/2008 |
| WO | 2009061853 | A2 | 5/2009 |
| WO | 2012088446 | A1 | 6/2012 |
| WO | 2012119093 | A1 | 9/2012 |
| WO | 2015164815 | A1 | 10/2015 |
| WO | 2018119114 | A1 | 6/2018 |
| WO | 2018234862 | A1 | 12/2018 |
| WO | 2019028425 | A1 | 2/2019 |
| WO | 2019092181 | A1 | 5/2019 |
| WO | 2019104092 | A1 | 5/2019 |

(Continued)

OTHER PUBLICATIONS

International Search Report in PCT/US2021/013514, mailed May 5, 2021.
Anonymous, "Database Accession No. JA808630", Sequence 16 from Patent WO2012088383, Database EPO Proteins, Nov. 27, 2012, 1 page.
Carmenate et al., "Human IL-2 Mutein with Higher Antitumor Efficacy Than Wild Type IL-2", Journal of Immunology, vol. 190, No. 12, Jun. 15, 2013, pp. 6230-6238.
Cassell et al., "Therapeutic Enhancement of IL-2 Through Molecular Design", Current Pharmaceutical Design, vol. 8, No. 24, Nov. 1, 2002, pp. 2171-2183.
Charych et al., "NKTR-214, an Engineered Cytokine with Biased IL2 Receptor Binding, Increased Tumor Exposure, and Marked Efficacy in Mouse Tumor Models", Supplemental to Clinical Cancer Research Journal, 2016.

(Continued)

*Primary Examiner* — Gyan Chandra
(74) *Attorney, Agent, or Firm* — Kilpatrick Townsend & Stockton LLP

(57) ABSTRACT

The present disclosures is related to IL2 muteins and their uses in the treatment of human disease.

14 Claims, 5 Drawing Sheets

Specification includes a Sequence Listing.

(56) References Cited

FOREIGN PATENT DOCUMENTS

| | | | |
|---|---|---|---|
| WO | 2019177986 | A1 | 9/2019 |
| WO | 2019/246404 | A1 | 12/2019 |

OTHER PUBLICATIONS

Charych et al., "NKTR-214, an Engineered Cytokine with Biased IL2 Receptor Binding, Increased Tumor Exposure, and Marked Efficacy in Mouse Tumor Models", Clinical Cancer Research, vol. 22, No. 3, Feb. 1, 2016, pp. 680-690.
Emmerich et al., "Abstract 1744: STK-012, An Alpha/beta Selective IL-2 Mutein for the Activation of the Antigen-activated T Cells in Solid Tumor", Cancer Research, vol. 81, No. 13, Jul. 1, 2021, pp. 1-3.
Application No. EP21741554.6 , "Partial Supplementary European Search Report", Jan. 24, 2024, 18 pages.
Application No. EP21741732.8 , Extended European Search Report, Mailed On Dec. 21, 2023, 8 pages.
Application No. EP18881013.9 , "Partial Supplementary European Search Report", Sep. 10, 2021, 16 pages.
Hargadon et al., "Immune Checkpoint Blockade Therapy for Cancer: An Overview of FDA-Approved Immune Checkpoint Inhibitors", International Immunopharmacology, vol. 62, Sep. 1, 2018, pp. 29-39.
Langowski et al., "The CD122-Biased Immunostimulatory Cytokine NKTR-214 Combined with Checkpoint Blockade Leads to Mobilization of Antitumor Immunity and Synergistic Activity", Cancer Immunology Research, vol. 4, No. 11, Nov. 1, 2016.
Leon et al., "Combining Computational and Experimental Biology to Develop Therapeutically Valuable IL2 Muteins", Seminars in Oncology, vol. 45, No. 1-2, Jan. 1, 2018, pp. 95-104.
Liang et al., "Characterization of Human Interleukin 2 Derived from Escherichia Coli", Biochemical Journal, vol. 229, No. 2, Jul. 15, 1985, pp. 429-439.
Mitra et al., "Interleukin-2 Activity can be Fine Tuned with Engineered Receptor Signaling Clamps", Immunity, vol. 42, No. 5, May 19, 2015, pp. 826-838.
Application No. PCT/US2018/062122 , International Search Report and Written Opinion, Mailed On Mar. 15, 2019, 13 pages.
Application No. PCT/US2021/013456 , International Search Report and Written Opinion, Mailed On Jul. 22, 2021, 15 pages.
Spolski et al., "Biology and Regulation of IL-2: from Molecular Mechanisms to Human Therapy", Nature Reviews, Immunology, vol. 18, No. 10, Oct. 1, 2018, pp. 648-659.

* cited by examiner

IL2 MUTEINS

CROSS-REFERENCE TO RELATED APPLICATION

The present application is a U.S. National Stage of PCT/US2021/013514, international filing date Jan. 14, 2021, which claims priority to U.S. Provisional Patent Application No. 62/960,847, filed on Jan. 14, 2020, the disclosure of each of which is incorporated herein by reference in its entirety for all purposes.

STATEMENT REGARDING GOVERNMENT FUNDING

No United States government funding was used in the conception or reduction to practice of the subject matter of the present disclosure.

SEQUENCE LISTING

The instant application contains a Sequence Listing which has been submitted electronically in ASCII format and is hereby incorporated by reference in its entirety. Said ASCII copy, created on Jun. 13, 2022, is named 1218660-Sequence-Listing.txt and is 37,971 bytes in size.

BACKGROUND OF THE INVENTION

Interleukin 2 (IL-2) is a pluripotent cytokine produced primarily by activated CD4+ T cells that is involved in producing a normal immune response. IL-2 exerts a wide spectrum of effects on the immune system and plays important roles in regulating both immune activation, suppression and homeostasis. IL-2 promotes proliferation and expansion of activated T lymphocytes, potentiates B cell growth, and activates monocytes and natural killer cells. The amino acid sequence of human IL-2 (SEQ ID NO: 1) is found in Genbank under accession locator NP_000577.2.

As an immune system stimulator, IL-2 has found use in the treatment of cancer and chronic viral infections. However, the effects of IL-2 have also been associated with mediation of autoimmunity and transplant rejection. IL2 therapy, especially at high doses, has been associated with significant toxicity in human subjects. Consequently, a therapeutic goal is to maintain desired actions of IL2 while minimizing associated autoimmune or immunosuppressive responses. Because of its roles in immune regulation and disease, the search for new IL-2 analogs and variants remains an active area of research.

IL-2 exerts its effect on mammalian immune cells through interaction with three different cell surface proteins: (1) CD25 (also referred to as the IL2 receptor alpha, IL-2Rα, p55), CD122 (also referred to as the interleukin-2 receptor beta, IL2Rβ, IL15Rβ and p70-75), and CD132 (also referred to as the interleukin 2 receptor gamma, IL-2Rγ; or common gamma chain as it is a component of other multimeric receptors in this family).

CD25 is a 55 kD polypeptide that is constituitively expressed in Treg cells and inducibly expressed on other T cells in response to activation (e.g. by CD3). hIL-2 binds to hCD25 with a Kd of approximately $10^{-8}$M. CD25 is also referred to in the literature as the "low affinity" IL-2 receptor. The human CD25 is expressed as a 272 amino acid pre-protein comprising a 21 amino acid signal sequence which is post-translationally removed to render a 251 amino acid mature protein. Amino acids 22-240) (amino acids 1-219 of the mature protein) correspond to the extracellular domain. Amino acids 241-259 (amino acids 220-238 of the mature protein) correspond to transmembrane domain. Amino acids 260-272 (amino acids 239-251 of the mature protein) correspond to intracellular domain. The intracellular domain of CD25 is comparatively small (13 amino acids) and has not been associated with any independent signaling activity. The IL2/CD25 complex has not been observed to produce a detectable intracellular signaling response. Human CD25 nucleic acid and protein sequences may be found as Genbank accession numbers NM_000417 and NP_0004Q8 respectively.

CD122 is a single pass type I transmembrane protein. The human CD122 (hCD122) is expressed as a 551 amino acid protein, the first 26 amino acids comprising a signal sequence which is post-translationally cleaved in the mature 525 amino acid protein. Amino acids 27-240) (amino acids 1-214 of the mature protein) correspond to the extracellular domain, amino acids 241-265 (amino acids 225-239 of the mature protein) correspond to the transmembrane domain and amino acids 266-551 (amino acids 240)-525 of the mature protein) correspond to the intracellular domain. As used herein, the term CD122 includes naturally occurring variants of the CD122 protein including the S57F and D365E (as numbered in accordance with the mature hCD122 protein). hCD122 is referenced at UniProtKB database as entry P14784. Human CD122 nucleic acid and protein sequences may be found as Genbank accession numbers NM_000878 and NP_000869 respectively.

CD132 is a type 1 cytokine receptor and is shared by the receptor complexes for IL-4, IL-7, IL-9, IL-15, and IL-21, hence the reference to the "common" gamma chain. Human CD132 (hCD132) is expressed as a 369 amino acid preprotein comprising a 22 amino acid N-terminal signal sequence. Amino acids 23-262 (amino acids 1-240 of the mature protein) correspond to the extracellular domain, amino acids 263-283 (amino acids 241-262 of the mature protein) correspond to the 21 amino acid transmembrane domain, and amino acids 284-369 (amino acids 262-347 of the mature protein) correspond to the intracellular domain. hCD132 is referenced at UniProtKB database as entry P31785. Human CD132 nucleic acid and protein sequences may be found as Genbank accession numbers: NM_000206 and NP_000197 respectively.

The IL2 receptor proteins combine to produce two additional IL-2 receptor complexes: (a) an "intermediate affinity" IL2 receptor comprising CD122 and CD132 (also referred to as IL2Rβγ) and (b) a "high affinity" IL2 receptor complex comprising the CD25, CD122 and CD132 proteins (also referred to as IL2Rαβγ"). hIL-2 possesses a Kd of approximately 10e-9M with respect to the intermediate affinity CD122/CD132 (IL2βγ) receptor complex. The intermediate affinity CD122/CD132 (IL2βγ) receptor complex is predominantly expressed on resting T-cells and NK cells. hIL-2 possesses a Kd of approximately 10e-11M with respect to the high IL-2 affinity receptor complex. Most cells, such as resting T cells, demonstrate low responsiveness to IL-2 since they only express the CD122 and CD132 which have comparatively low affinity for IL-2 relative to the CD25/CD122/CD132 high affinity receptor complex. The high affinity receptor complex is predominantly identified on activated lymphocytes which inducibly express CD25 and Treg cells that express CD25 constituitively.

In light of the pluripotent effects of the IL2 molecule and its demonstrated ability to modulate the activities of a wide variety of cell types associated with human disease, IL-2 muteins that retain certain desirable features of the native molecule while minimizing undesirable features, depending on the therapeutic context, would be useful in the treatment of human disease.

Garcia, et al. (International Application Number PCT/2018/062122, PCT International Publication No. WO 2019/104092 A1 published May 31, 2019, hereinafter "Garcia '092") describes certain IL2 muteins having modifications including positions 18, 22 and 126 that, among other things, exhibit diminished binding for CD132 while retaining partial IL2 activity.

The present disclosure provides IL-2 muteins that function as IL-2 partial agonists and antagonists.

SUMMARY OF THE DISCLOSURE

The present disclosure provides methods and compositions for the treatment and/or prevention of inflammatory, infectious or autoimmune diseases, disorders or conditions by the administration of a therapeutically effective amount of an human IL-2 muteins that have decreased binding affinity for CD132 yet retain significant binding affinity for CD122 and/or CD25 comparable to the activity of wild-type human IL-2.

In some embodiments, the disclosure methods and compositions for the treatment and/or prevention of inflammatory, infectious or autoimmune diseases, disorders or conditions by the administration of a therapeutically effective amount of an human IL-2 muteins that have decreased binding affinity for CD132 yet retain significant binding affinity for CD122 and/or CD25 comparable to the activity of wild-type human that function as IL-2 in combination with a supplementary agents, including but not limited to one or more of chemotherapeutics, immune checkpoint modulators, radiotherapy and/or physical interventional treatment methods such as surgery.

In some embodiments the present disclosure provides methods and compositions for the treatment and/or prevention of inflammatory, infectious or autoimmune diseases, disorders or conditions by the administration of a therapeutically effective amount of an human IL-2 muteins that have decreased binding affinity for CD132 yet retain significant binding affinity for CD122 and/or CD25 comparable to the activity of wild-type human that function as IL-2 wherein the serum concentration of said IL2 mutein is maintained for a period of time at a serum concentration at or above the effective concentration of the IL2 mutein sufficient to promote proliferation of CD3-activated primary human T-cells with respect to such IL2 mutein but at a serum concentration at or below of the effective concentration at a serum concentration of such IL2 mutein sufficient to induce activation of T-cells with respect to such IL2 mutein.

In some embodiments, the present disclosure provides human interleukin-2 (IL-2) muteins providing modified binding properties to one or more IL2 receptors for the treatment of inflammatory, infectious or autoimmune diseases, disorders or conditions. In some embodiments, the IL-2 muteins possess decreased binding affinity to the extracellular domain of hCD132.

In some embodiments, the IL-2 muteins possess decreased binding affinity to the extracellular domain of hCD132 while retaining significant binding to the hCD25/hCD122 receptor complex and/or activation of the hCD25/hCD122/hCD132 receptor complex.

In some embodiments, the IL-2 muteins possess decreased binding affinity to CD132 while retaining substantial binding affinity for hCD25.

In one aspect, the present disclosure provides hIL-2 muteins exhibiting significant or enhanced binding affinity for hCD25 and reduced binding affinity for the extracellular domain of hCD132 receptor as compared to wild type human IL-2 (hIL-2). In some embodiments, the IL-2 muteins comprise one or more amino acid substitutions that decrease CD132 receptor binding affinity selected from amino acid positions 18, 22, and 126, numbered in accordance with mature wild type hIL-2.

In another aspect, the present disclosure provides a polypeptide comprising an amino acid sequence of the formula (SEQ ID NO: 97):

$(AA1)_a$-$(AA2)_b$-$(AA3)_c$-$(AA4)_d$-$(AA5)_e$-$(AA6)_f$-$(AA7)_g$-$(AA8)_h$-$(AA9)_i$-T10-Q11-L12-Q13-L14-E15-H16-L17-(AA18)-L19-D20-L21-(AA22)-M23-124-L25-N26-G27-128-N29-N30-Y31-K32-N33-P34-(AA35)-L36-T37-(AA38)-(AA39)-L40-T41-F42-K43-F44-Y45-M46-P47-K48-K49-A50-T51-E52-L53-K54-(AA55)-L56-Q57-C58-L59-E60-E61-E62-L63-K64-P65-L66-E67-E68-(AA69)-L70-N71-L72-A73-(AA74)-S75-K76-N77-F78-H79-(AA80-(AA81)-P82-R83-D84-(AA85)-(AA86)-S87-N88-(AA89)-N90-(AA91)-(AA92)-V93-L94-E95-L96-(AA97)-G98-S99-E100-T101-T102-F103-(AA104)-C105-E106-Y107-A108-(AA109)-E110-T111-A112-(AA113)-I114-V115-E116-F117-L118-N119-R120-W121-1122-T123-F124-(AA125)-(AA126)-S127-I128-I129-(AA130)-T131-L132-T133 wherein:

- each of a, b, c, d, e, f, g, h, and i is individually selected from 0 or 1;
- AA1 is A (wild type, a=1) or deleted (a=0);
- AA2 is P (wild type, b=1) or deleted (b=0);
- AA3 is T (wild type, c=1), C, A, G, Q, E, N, D, R, K, P, or deleted (c=0);
- AA4 is S (wild type, d=1) or deleted (d=0);
- AA5 is S (wild type, e=1) or deleted (e=0);
- AA6 is S (wild type, f=1) or deleted (f=0);
- AA7 is T (wild type, g=1) or deleted (g=0);
- AA8 is K (wild type, h=1) or deleted (h=0);
- AA9 is K (wild type, i=1) or deleted (i=0);
- AA18 is L (wild type) or R, L, G, M, F, E, H, W, K, Q, S, V, I, Y, H, D or T;
- AA22 is Q (wild type) or F, E, G, A, L, M, F, W, K, S, V, I, Y, H, R, N, D, T, or F;
- AA35 is K (wildtype) or E;
- AA38 is R (wild type), W or G;
- AA39 is M (wildtype), L or V;
- AA55 is H (wildtype) or Y;
- AA69 is V (wildtype) or A;
- AA74 is Q (wild type), P, N, H, S;
- AA80 is L (wild type), F or V;
- AA81 is R (wild type), I, D or T;
- AA85 is L (wild type) or V;
- AA86 is I (wild type) or V;
- AA89 is I (wild type) or V;
- AA91 is V (wild type), R or K;
- AA92 is I (wild type) or F;
- AA97 is K (wild type) or Q;
- AA104 is M (wild type) or A;
- AA109 is D (wildtype), C or a non-natural amino acid with an activated side chain;
- AA113 is T (wild type) or N;
- AA125 is C (wild type), A or S;
- AA126 is Q (wild type) or H, M, K, C, D, E, G, I, R, S, or T; and
- AA130 is S (wild type), T, G or R; and with the proviso that if AA18 is R and AA22 is E, then AA126 is not H, M, K, C, D, E, G, I, R, S, or T.

In some embodiments of this aspect,

AA18 is selected from the group consisting of L (wild type) or R, L, G, M, F, E, H, W, K, Q, S, V, I, Y, H, D or T;

AA22 is selected from the group consisting of Q (wild type) or F, E, G, A, L, M, F, W, K, S, V, I, Y, H, R, N, D, T, or F; and AA126 is selected from the group consisting of Q (wild type) or H, M, K, C, D, E, G, I, R, S, or T.

In some embodiments, the polypeptide comprises a set of mutations selected from the group consisting of: L18R, Q22E and Q126M; L18R, Q22E Q126T; L18R; Q22E; Q126H; L18R, and Q126H; Q22E, and Q126H; L18G, Q22E and Q126H; L18A, Q22E and Q126H; L18M, Q22E and Q126H; L18F, Q22E and Q126H; L18W, Q22E and Q126H; L18K, Q22E and Q126H; L18Q, Q22E and Q126H; L18E, Q22E and Q126H; L18S, Q22E and Q126H; L18V, Q22E and Q126H; L18I, Q22E and Q126H; L18Y, Q22E and Q126H; L18H, Q22E and Q126H; L18N, Q22E and Q126H; L18D, Q22E and Q126H; L18T, Q22E and Q126H; L18R, Q22G and Q126H; L18R, Q22A and Q126H; L18R, Q22L and Q126H; L18R, Q22M and Q126H; L18R, Q22F and Q126H; L18R, Q22W and Q126H; L18R, Q22K and Q126H; L18R, Q22S and Q126H; L18R, Q22V and Q126H; L18R, Q221 and Q126H; L18R Q22Y and Q126H; L18R Q22H and Q126H; L18R Q22R and Q126H; L18R Q22N and Q126H; L18R Q22D and Q126H; and L18R Q22T and Q126H.

In some embodiments, the polypeptide is PEGylated. In some embodiments, the polypeptide is PEGylated and the PEG component of such PEGylated polypeptide has a molecular weight of from about 10 kD to about 70 kD.

In some embodiments, the polypeptide is a fusion protein. In certain embodiments, the fusion protein comprises an Fc domain.

In another aspect, the disclosure provides a nucleic acid encoding a polypeptide described herein. In some embodiments, the nucleic acid is DNA.

In another aspect, the disclosure provides a recombinant expression vector comprising the nucleic acid described herein. In some embodiments, the vector is a viral vector. In certain embodiments, the vector is a non-viral vector.

In another aspect, the disclosure provides a host cell transformed with a vector described herein.

In another aspect, the disclosure provides a pharmaceutical formulation comprising a polypeptide, a nucleic acid, or a vector described herein.

In another aspect, the disclosure provides a method of treating a mammalian subject suffering from an autoimmune or inflammatory disease, disorder or condition or viral infection, the method comprising administering a therapeutically-effective amount of pharmaceutical formulation described herein.

In some embodiments, the method further comprises administering one or more supplementary agents selected from the group consisting of a corticosteroid, a Janus kinase inhibitor, a calcineurin inhibitor, a mTor inhibitor, an IMDH inhibitor, a biologic, a vaccine, and a therapeutic antibody. In certain embodiments, the therapeutic antibody is an antibody that binds a protein selected from the group consisting of BLyS, CD11a, CD20, CD25, CD3, CD52,IgEIL-12/IL-23, IL-17a, IL-1ß, IL-4Rα, IL-5, IL-6R, integrin-α4β7, RANKL, TNFα, VEGF-A, and VLA-4.

In some embodiments, the disease, disorder or condition is selected from viral infections, heliobacter *pylori* infection, HTLV, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome, psoriasis, psoriatic arthritis, dermatitis (eczema), exfoliative dermatitis or atopic dermatitis, *pityriasis rubra* pilaris, *pityriasis* rosacea, parapsoriasis, *pityriasis* lichenoiders, lichen planus, lichen *nitidus*, ichthyosiform dermatosis, keratodermas, dermatosis, alopecia areata, pyoderma gangrenosum, vitiligo, pemphigoid, urticaria, prokeratosis, rheumatoid arthritis: seborrheic dermatitis, solar dermatitis: seborrheic keratosis, senile keratosis, actinic keratosis, photo-induced keratosis, keratosis follicularis: acne vulgaris: keloids: nevi: warts including verruca, condyloma or condyloma *acuminatum*, and human papilloma viral (HPV) infections.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
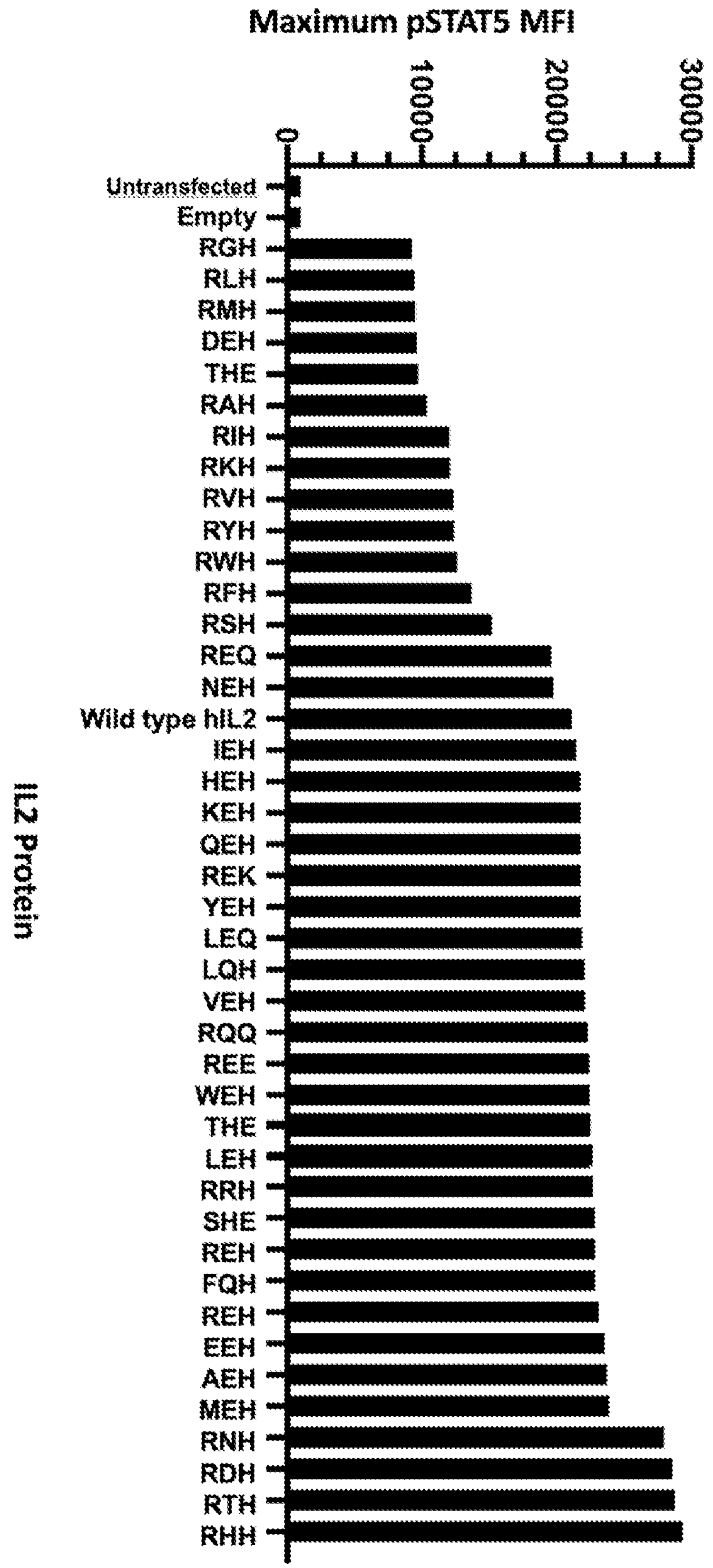
FIG. 1 provides a graphical representation of pSTAT5 levels as measured in NKL cells treated with 293T transfection supernatant containing the indicated IL2 muteins (and controls) as described in the Examples. The vertical axis represents the level of IL2 activity as measured in accordance with the Examples and each bar indicates the level of activity of the particular IL2 peptide evaluated associated with the construct as identified by its 3 letter abbreviation as described in the Examples.

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this invention is not limited to particular method or composition described, as such may, of course, vary. It is also to be understood that the terminology used herein is for the purpose of describing particular embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s): pl=picoliter(s): s or sec=second(s); min=minute(s); h or hr=hour(s): AA or aa=amino acid(s); kb=kilobase(s); nt=nucleotide(s): pg=picogram; ng-nanogram: μg=microgram; mg=milligram: g=gram; kg=kilogram: dl or dL=deciliter: μl or μL=microliter; ml or mL=milliliter: 1 or L=liter; μM=micromolar; mM=millimolar: M=molar: kDa=kilodalton; i.m.=intramuscular(ly); i.p.=intraperitoneal (ly): SC or SQ=subcutaneous(ly): QD=daily: BID=twice daily: QW=once weekly: QM=once monthly; HPLC=high performance liquid chromatography: BW=body weight: U=unit; ns=not statistically significant: PBS=phosphate-buffered saline: PCR=polymerase chain reaction; HSA=human serum albumin: MSA=mouse serum albumin: DMEM=Dulbeco's Modification of Eagle's Medium: EDTA=ethylenediaminetetraacetic acid.

It will be appreciated that throughout this disclosure reference is made to amino acids according to the single letter or three letter codes. For the reader's convenience, the single and three letter amino acid codes are provided in Table 1 below:

TABLE 1

| Amino Acid Abbreviations | | |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Unless otherwise indicated, the following terms are intended to have the meaning set forth below. Other terms are defined elsewhere throughout the specification.

Definitions

Activate: As used herein the term "activate" is used in reference to a receptor or receptor complex to reflect the biological effect of the binding of an agonist ligand to the receptor. Activators are molecules that increase, activate, facilitate, enhance activation, sensitize, or up-regulate, e.g., a gene, protein, ligand, receptor, or cell. For example, the binding of an IL2 agonist to an IL2 receptor (e.g., the high affinity CD25/CD122/CD132 receptor complex) "activates" the signaling of the receptor to produce one or more intracellular biological effects (e.g. the phosphorylation of STAT5).

Activity: As used herein, the term "activity" is used with respect to a molecule to describe a property of the molecule with respect to a test system or biological function such as the degree of binding of the molecule to another molecule.

Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a biological activity per unit of administered agent such as [catalytic activity]/[mg protein], [immunological activity]/[mg protein], international units (IU) of activity, [STAT5 phosphorylation]/[mg protein], [T-cell proliferation]/[mg protein], plaque forming units (pfu), etc.

Administer/Administration: The terms "administration" and "administer" are used interchangeably herein to refer the act of contacting a subject, including contacting a cell, tissue, organ, or biological fluid in vitro, in vivo and/or ex vivo of a subject with an agent (e.g. an IL-2 mutein or a pharmaceutical formulation thereof). Administration of an agent may be achieved through any of a variety of art recognized methods including but not limited to the topical, intravascular injection (including intravenous or intraarterial infusion), intradermal injection, subcutaneous injection, intramuscular injection, intraperitoneal injection, intracranial injection, intratumoral injection, intranodal injection, transdermal, transmucosal, iontophoretic delivery, intralymphatic injection (Senti and Kundig (2009) Current Opinions in Allergy and Clinical Immunology 9(6): 537-543), intragastric infusion, intraprostatic injection, intravesical infusion (e.g., bladder), respiratory inhalers including nebulizers, intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell. The term "administration" includes the ex vivo contact of a cell (or population of cells) that may be isolated from a subject and contacted with an agent and the cell (or population of cells) is administered to the same subject (e.g. autologous cell transfer) or a different subject (e.g. allogeneic cell transfer).

Adverse Event: As used herein, the term "adverse event" refers to any undesirable experience associated with the use of a therapeutic or prophylactic agent in a subject. Adverse events do not have to be caused by the administration of the therapeutic or prophylactic agent (e.g. the IL2 mutein) but may arise from unrelated circumstances. Adverse events are typically categorized as mild, moderate, or severe. As used herein, the classification of adverse events as used herein is in accordance with the Common Terminology Criteria for Adverse Events v5.0 (CTCAE) dated published Nov. 27, 2017 published by the United States Department of Health and Human Services, the National Institutes of Health and the National Cancer Institute.

Affinity: As used herein the term "affinity" refers to the degree of specific binding of a first molecule (e.g. a ligand) to a second molecule (e.g. a receptor) and is measured by the binding kinetics expressed as $K_d$, a ratio of the dissociation constant between the molecule and the its target ($K_{off}$) and the association constant between the molecule and its target ($K_{on}$).

Agonist: As used herein, the term "agonist" refers an agent that specifically binds a second molecule ("target") and interacts with the target to cause or promote an increase in the activation of the target. Agonists are activators that modulate cell activation, enhance activation, sensitize cells to activation by a second agent, or up-regulate, e. g . . . a gene, protein, ligand, receptor, biological pathway including an immune checkpoint pathway in a cell, or cell proliferation. In some embodiments, an agonist is an agent that binds to a receptor and alters the receptor state, resulting in a biological response. The response mimics the effect of the endogenous activator of the receptor. The term "agonist" includes partial agonists, full agonists and superagonists. An agonist may be described as a "full agonist" when such agonist which leads to full response (i.e. the response associated with the naturally occurring ligand/receptor binding interaction) induced by receptor under study, or a partial agonist. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist. A "superagonist" is a type of agonist that is capable of producing a maximal response greater than the endogenous agonist for the target receptor, and thus has an efficacy of more than 100%. An IL-2 superagonist of the present disclosure may have greater than 110%, alternatively greater than 120%, alternatively greater than 130%, alternatively greater than 140%, alternatively greater than 150%, alternatively greater than 160%, or alternatively greater than 170% of the activity of WHO International Standard (NIBSC code: 86/500) wild type mature human IL-2 when evaluated at similar concentrations in a comparable assay.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or downregulate, e.g., a gene, protein, ligand, receptor, biological pathway, or cell Antibody: As used herein, the term "antibody" refers collectively to: (a) glycosylated and non-glycosylated the immunoglobulins (including but not limited to mammalian immunoglobulin classes IgG1, IgG2, IgG3 and IgG4) that specifically binds to target molecule and (b) immunoglobulin derivatives including but not limited to IgG(1-4)delta$C_H$2, $F(ab)_2$, Fab, ScFv, $V_H$, $V_L$, tetrabodies, triabodies, diabodies, dsFv, $F(ab)_3$, scFv-Fc and $(scFv)_2$ that competes with the immunoglobulin from which it was derived for binding to the target molecule. The term antibody is not restricted to immunoglobulins derived from any particular mammalian species and includes murine, human, equine, camelids, antibodies, human antibodies. The term antibody includes so called "heavy chain antibodies" or "VHHs" or "Nanobodies®" as typically obtained from immunization of camelids (including camels, llamas and alpacas (see, e.g. Hamers-Casterman, et al. (1993) Nature 363:446-448). Antibodies having a given specificity may also be derived from non-mammalian sources such as VHHs obtained from immunization of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies. The term ""human antibody" includes antibodies obtained from human beings as well as antibodies obtained from transgenic mammals comprising human immunoglobulin genes such that, upon stimulation with an antigen the transgenic animal produces antibodies comprising amino acid sequences characteristic of antibodies produced by human beings. The term antibody includes both the parent antibody and its derivatives such as affinity matured, veneered, CDR grafted (including CDR grafted VHHs), humanized, camelized (in the case of non-camel derived VHHs), or binding molecules comprising binding domains of antibodies (e.g., CDRs) in non-immunoglobulin scaffolds. The term "antibody" is not limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries or chemically synthesized (e.g., solid phase protein synthesis). In one embodiment, an "antibody" is a mammalian immunoglobulin. In some embodiments, the antibody is a "full length antibody" comprising variable and constant domains providing binding and effector functions. In most instances, a full-length antibody comprises two light chains and two heavy chains, each light chain comprising a variable region and a constant region. In some embodiments the term "full length antibody" is used to refer to conventional IgG immunoglobulin structures comprising two light chains and two heavy chains, each light chain comprising a variable region and a constant region providing binding and effector functions. The term antibody includes antibody conjugates comprising modifications to prolong duration of action such as fusion proteins or conjugation to polymers (e.g. PEGylated) as described in more detail below:

Biological Sample: As used herein, the term "biological sample" or "sample" refers to a sample obtained or derived from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow; and an immunoglobulin enriched fraction derived from one or more of these tissues. In some embodiments, the sample is obtained from a subject who has been exposed to a therapeutic treatment regimen including a pharmaceutical formulation of a an IL2 mutein, such as the repeated exposure to the same IL2 mutein. In other embodiments, the sample is obtained from a subject who has not recently been exposed to the IL2 mutein or obtained from the subject prior to the planned administration of the IL2 mutein.

"CAR" or "Chimeric Antigen Receptor": As used herein, the terms "chimeric antigen receptor" and "CAR" are used interchangeably to refer to a chimeric polypeptide comprising multiple functional domains arranged from amino to carboxy terminus in the sequence: (a) an extracellular domain (ECD) comprising an antigen binding domain (ABD) and "hinge" domain, (b) a transmembrane domain (TD); and (c) one or more cytoplasmic signaling domains (CSDs) wherein the foregoing domains may optionally be linked by one or more spacer domains. The CAR may also further comprise a signal peptide sequence which is conventionally removed during post-translational processing and presentation of the CAR on the cell surface of a cell transformed with an expression vector comprising a nucleic acid sequence encoding the CAR. CARs may be prepared in accordance with principles well known in the art. See e.g., Eshhar, et al. (U.S. Pat. No. 7,741,465 B1 issued Jun. 22, 2010): Sadelain, et al. (2013) Cancer Discovery 3 (4): 388-398: Campana and Imai (U.S. Pat. No. 8,399,645 issued Mar. 19, 2013) Jensen and Riddell (2015) Current Opinions in Immunology 33:9-15: Gross, et al. (1989) PNAS (USA) 86 (24): 10024-10028; Curran, et al. (2012) J Gene Med 14 (6): 405-15: Brogdon, et al. (U.S. Pat. No. 10,174,095 issued Jan. 8, 2019) Guedan, et al. (2019) Engineering and Design of Chimeric Antigen Receptors (2019) Molecular Therapy: Methods & Clinical Development Vol. 12:145-156.

CAR-T Cell: As used herein, the terms "chimeric antigen receptor T-cell" and "CAR-T cell" are used interchangeably to refer to a T-cell that has been recombinantly modified to express a chimeric antigen receptor. Examples of commercially available CAR-T cell products include axicabtagene ciloleucel (marketed as Yescarta® commercially available from Gilead Pharmaceuticals) and tisagenlecleucel (marketed as Kymriah® commercially available from Novartis).

CD25: As used herein, the terms "CD25", "IL2 receptor alpha", "IL-2Rα", "IL2Ra" and "p55" are used interchangeably to the 55 kD polypeptide that is constituitively expressed in Treg cells and inducibly expressed on other T cells in response to activation (e.g. by CD3CD25 is also referred to in the literature as the "low affinity" IL-2 receptor. Human CD25 nucleic acid and protein sequences may be found as Genbank accession numbers NM_000417 and NP_0004Q8 respectively. The human CD25 is expressed as a 272 amino acid pre-protein comprising a 21 amino acid signal sequence which is post-translationally removed to render a 251 amino acid mature protein. Amino acids 22-240 (amino acids 1-219 of the mature protein) correspond to the extracellular domain. Amino acids 241-259 (amino acids 220-238 of the mature protein) correspond to transmembrane domain. Amino acids 260-272 (amino acids 239-251 of the mature protein) correspond to intracellular domain. The amino acid sequence of the mature form of hCD25 is:

(SEQ ID NO:. 1)

ELCDDDPPEIPHATFKAMAYKEGTMLNCECKRGFRRIKSGSLYMLCTGN

SSHSSWDNQCQCTSSATRNTTKQVTPQPEEQKERKTTEMQSPMQPVDQA

SLPGHCREPPPWENEATERIYHFVVGQMVYYQCVQGYRALHRGPAESVC

KMTHGKTRWTQPQLICTGEMETSQFPGEEKPQASPEGRPESETSCLVTT

TDFQIQTEMAATMETSIFTTEYQVAVAGCVFLLISVLLLSGLTWQRRQR

KSRRTI

CD122: As used herein, the terms "CD122", "interleukin-2 receptor beta", "IL2Rb", "IL2Rβ", "IL15Rβ" and "p70-75" are used interchangeably to refer to the human CD122 transmembrane protein. The human CD122 (hCD122) is expressed as a 551 amino acid protein, the first 26 amino acids comprising a signal sequence which is post-translationally cleaved in the mature 525 amino acid protein. Amino acids 27-240 (amino acids 1-214 of the mature protein) correspond to the extracellular domain, amino acids 241-265 (amino acids 225-239 of the mature protein) correspond to the transmembrane domain and amino acids 266-551 (amino acids 240-525 of the mature protein) correspond to the intracellular domain. As used herein, the term CD122 includes naturally occurring variants of the CD122 protein including the S57F and D365E (as numbered in accordance with the mature hCD122 protein). hCD122 is referenced at UniProtKB database as entry P14784. Human CD122 nucleic acid and protein sequences may be found as Genbank accession numbers NM_000878 and NP_000869 respectively. The amino acid sequence of the mature hCD122 protein is:

(SEQ ID NO: 2)
AVNGTSQFTCFYNSRANISCVWSQDGALQDTSCQVHAWPDRRRWNQTCE

LLPVSQASWACNLILGAPDSQKLTTVDIVTLRVLCREGVRWRVMAIQDF

KPFENLRLMAPISLOVVHVETHRCNISWEISQASHYFERHLEFEARTLS

PGHTWEEAPLLTLKQKQEWICLETLTPDTQYEFQVRVKPLQGEFTTWSP

WSQPLAFRTKPAALGKDTIPWLGHLLVGLSGAFGFIILVYLLINCRNTG

PWLKKVLKCNTPDPSKFFSQLSSEHGGDVQKWLSSPFPSSSFSPGGLAP

EISPLEVLERDKVTQLLLQQDKVPEPASLSSNHSLTSCFTNQGYFFFHL

PDALEIEACQVYFTYDPYSEEDPDEGVAGAPTGSSPQPLQPLSGEDDAY

CTFPSRDDLLLFSPSLLGGPSPPSTAPGGSGAGEERMPPSLQERVPRDW

DPQPLGPPTPGVPDLVDFQPPPELVLREAGEEVPDAGPREGVSFPWSRP

PGQGEFRALNARLPLNTDAYLSLQELQGQDPTHLV

And the amino acid sequence of the extracellular domain of the hCD122 is:

(SEQ ID NO: 3)
AVNGTSQFTCFYNSRANISCVWSQDGALQDTSCQVHAWPDRRRWNQTCE

LLPVSQASWACNLILGAPDSQKLTTVDIVTLRVLCREGVRWRVMAIQDF

KPFENLRLMAPISLOVVHVETHRCNISWEISQASHYFERHLEFEARTLS

PGHTWEEAPLLTLKQKQEWICLETLTPDTQYEFQVRVKPLQGEFTTWSP

WSQPLAFRTKPAALGKDT

CD132: As used herein, the terms “CD132”, “IL2 receptor gamma”, “IL2Rg, “IL2Rγ” refers to a type 1 cytokine receptor and is shared by the receptor complexes for IL-4, IL-7, IL-9, IL-15, and IL-21, hence the reference to the “common” gamma chain. Human CD132 (hCD132) is expressed as a 369 amino acid pre-protein comprising a 22 amino acid N-terminal signal sequence. Amino acids 23-262 (amino acids 1-240 of the mature protein) correspond to the extracellular domain, amino acids 263-283 (amino acids 241-262 of the mature protein) correspond to the 21 amino acid transmembrane domain, and amino acids 284-369 (amino acids 262-347 of the mature protein) correspond to the intracellular domain. hCD132 is referenced at UniProtKB database as entry P31785. Human CD132 nucleic acid and protein sequences may be found as Genbank accession numbers: NM_000206 and NP_000197 respectively. The amino acid sequence of the mature hCD132 protein is:

(SEQ ID NO: 4)
LNTTILTPNGNEDTTADFFLTTMPTDSLSVSTLPLPEVQCFVENVEYMN

CTWNSSSEPQPTNLTLHYWYKNSDNDKVQKCSHYLFSEEITSGCQLQKK

EIHLYQTFVVQLQDPREPRRQATQMLKLQNLVIPWAPENLTLHKLSESQ

LELNWNNRFLNHCLEHLVQYRTDWDHSWTEQSVDYRHKFSLPSVDGQKR

-continued

YTFRVRSRENPLCGSAQHWSEWSHPIHWGSNTSKENPFLFALEAVVISV

GSMGLIISLLCVYFWLERTMPRIPTLKNLEDLVTEYHGNFSAWSGVSKG

LAESLOPDYSERLCLVSEIPPKGGALGEGPGASPCNQHSPYWAPPCYTL

KPET

CDRs. As used herein, the term “CDR” or “complementarity determining region” is intended to mean the non-contiguous antigen combining sites found within the variable region of both heavy and light chain immunoglobulin polypeptides (or heavy chains in the case of VHHs). CDRs have been described by Kabat, et al. (1977) *J. Biol. Chem.* 252:6609-6616: Kabat, et al. (1991) U.S. Dept. of Health and Human Services, “Sequences of proteins of immunological interest” (also referred to herein as “Kabat 1991”): by Chothia et al. (1987) *J. Mol. Biol.* 196:901-917; and MacCallum et al., *J. Mol. Biol.* 262:732-745 (1996), where the definitions include overlapping or subsets of amino acid residues when compared against each other. In the context of the present disclosure, the numbering of CDR positions is provided according to Kabat numbering conventions.

Comparable: As used herein, the term “comparable” is used to describe the degree of difference in two measurements of an evaluable quantitative or qualitative parameter. For example, where a first measurement of an evaluable quantitative parameter (e.g. the level of IL-2 activity as determined by an CTLL-2 proliferation or phospho-STAT5 assay) and a second measurement of the evaluable parameter do not deviate beyond a range that the skilled artisan would recognize as not producing a statistically significant difference in effect between the two results in the circumstances, the two measurements would be considered “comparable.” In some instances, measurements may be considered “comparable” if one measurement deviates from another by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Derived From: As used herein in the term “derived from”, in the context of an amino acid sequence or polynucleotide sequence (e.g., an amino acid sequence “derived from” an IL-2 polypeptide), is meant to indicate that the polypeptide or nucleic acid has a sequence that is based on that of a reference polypeptide or nucleic acid (e.g., a naturally occurring IL-2 polypeptide or an IL-2-encoding nucleic acid), and is not meant to be limiting as to the source or method in which the protein or nucleic acid is made. By way of example, the term “derived from” includes homologs or variants of reference amino acid or DNA sequences.

Enriched: As used herein in the term “enriched” refers to a sample is non-naturally manipulated so that a molecule of interest is present in: (a) a greater concentration (e.g., at least 3-fold greater, alternatively at least 5-fold greater, alternatively at least 10-fold greater, alternatively at least 50-fold greater, alternatively at least 100-fold greater, alternatively at least 1000-fold greater) than the concentration of the molecule in the starting sample, such as a biological sample (e.g., a sample in which the molecule naturally occurs or in which it is present after administration): or (b) a concentration greater than the environment in which the molecule was made (e.g., as in a recombinantly modified bacterial or mammalian cell).

Extracellular Domain: As used herein the term "extracellular domain" or its abbreviation "ECD" refers to the portion of a cell surface protein (e.g. a cell surface receptor) which is outside of the plasma membrane of a cell. The term "ECD" may include the extra-cytoplasmic portion of a transmembrane protein or the extra-cytoplasmic portion of a cell surface (or membrane associated protein).

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

IL-2: As used herein, the term "interleukin-2" or "IL-2" refers to a naturally occurring IL-2 polypeptide that possesses IL-2 activity. In some embodiments, IL-2 refers to mature wild type human IL-2. Mature wild type human IL-2 (hIL2) occurs as a 133 amino acid mature polypeptide (less the signal peptide, consisting of an additional 20 N-terminal amino acids), as described in Fujita, et. al., PNAS USA, 80, 7437-7441 (1983). An amino acid sequence of naturally occurring variant of mature wild type human IL-2 (hIL2) is:

```
                                    (SEQ ID NO: 5)
APTSSSTKKT QLQLEHLLLD LQMILNGINN YKNPKLTRML

TFKFYMPKKA TELKHLQCLE EELKPLEEVL NLAQSKNFHL

RPRDLISNIN VIVLELKGSE TTFMCEYADE TATIVEFLNR

WITFCQSIIS TLT
```

As used herein, the numbering of residues of the hIL2 muteins is based on the hIL2 sequence UniProt ID P60568 excluding the signal peptide which is the same as that of SEQ ID NO:5.

IL2 Activity: The term "IL2 activity" refers to one or more the biological effects on a cell in response to contacting the cell with an effective amount of an IL2 polypeptide. IL2 activity may be measured, for example, in a cell proliferation assay using CTLL-2 mouse cytotoxic T cells, in substantial accordance with the teaching of Gearing, A. J. H. and C. B. Bird (1987) in Lymphokines and Interferons, A Practical Approach. Clemens, M. J. et al. (eds): IRL Press. 295. The specific activity of recombinant human IL-2 (rhIL2) is approximately $2.1\times10^4$ IU/μg, which is calibrated against recombinant human IL-2 WHO International Standard (NIBSC code: 86/500). IL2 activity may be expressed as the level of STAT5 phosphorylation which may be determined by flow cytometric methods known in the art (Bitar, et al (2019) *Evaluating STAT5 Phosphorylation As A Mean to Assess T Cell Proliferation* (2019) Frontiers In Immunology Volume 10, Article 722, pages 1-11.

IL-2 mutein: As used herein, the term "IL-2 mutein" refers to a mutein derived from a naturally occurring form of IL2 comprising modifications to amino acid sequence of the IL2 molecule. The IL-2 muteins are characterized by amino acid insertions, deletions, substitutions and modifications at one or more sites in or at the other residues of the native parent IL-2 polypeptide chain. In some embodiments, IL2 muteins of the present retain CD122 binding activity comparable to the activity of WHO International Standard (NIBSC code: 86/500) wild type mature human IL-2 when evaluated at similar concentrations in a comparable assay. Exemplary muteins can include substitutions of 1, 2, 3, 4, 5, 6, 7, 8, 9, 10 or more amino acids.

In An Amount Sufficient Amount to Effect a Change: As used herein the phrase "in an amount sufficient to effect a change" refers to the amount of a test agent sufficient to provide a detectable difference between a level of an indicator measured before (e.g., a baseline level) and after the application of the test agent to a system such as biological function evaluated in a cell based assay in response to the administration of a quantity of the test agent. "An amount sufficient to effect a change" may be sufficient to be a therapeutically effective amount but "in an amount sufficient to effect a change" may be more or less than a therapeutically effective amount.

In Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise.

In Need of Prevention: As used herein the term "in need of prevention" refers to a judgment made by a physician or other caregiver with respect to a subject that the subject requires or will potentially benefit from preventative care. This judgment is made based upon a variety of factors that are in the realm of a physician's or caregiver's expertise.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

Kabat Numbering: The term "Kabat numbering" as used herein is a term recognized in the art of antibody engineering to refer to a system of numbering amino acid residues which are more variable than other amino acid residues (e.g., hypervariable residues) in the heavy and light chain regions of immunoglobulins (Kabat, et al., (1971) *Ann. NY Acad. Sci.* 190:382-93: Kabat, et al., (1991) *Sequences of Proteins of Immunological Interest*, Fifth Edition, U.S. Department of Health and Human Services, NIH Publication No. 91-3242). For purposes of the present disclosure, the positioning of CDRs in the variable region of an antibody as disclosed herein follows Kabat numbering or simply, "Kabat."

Ligand: As used herein, the term "ligand" refers to a molecule that exhibits specific binding to a receptor and results in a change in the biological activity of the receptor so as to effect a change in the activity of the receptor to which it binds. In one embodiment, the term "ligand" refers to a molecule, or complex thereof, that can act as an agonist or antagonist of a receptor. As used herein, the term "ligand" encompasses natural and synthetic ligands. "Ligand" also encompasses small molecules, e.g., peptide mimetics of cytokines and peptide mimetics of antibodies. The complex of a ligand and receptor is termed a "ligand-receptor complex."

Modified IL-2 Mutein: As used herein the term "modified IL-2 muteins" is used to refer to IL-2 muteins that have comprise one or more extra further modifications (i.e. modifications outside the core amino acid sequence of the IL2 mutein) such as pegylation, glycosylation (N- and O-linked), acylation, or polysialylation or by conjugation (either chemical or as fusion proteins) with other polypeptide carrier molecules including but not limited to albumin fusion polypeptides comprising serum albumin (e.g., human serum albumin (HSA) or bovine serum albumin (BSA) or and Fc-fusion proteins or with targeting moieties such as IgG comprising IL2 orthogonal polypeptide fusion proteins, targeted IL-2 mutein polypeptides such as ScFv-IL2 mutein polypeptide fusion proteins and VHH-IL-2 mutein polypeptide fusion proteins. Modified IL2 muteins may be prepared to order to enhance one or more properties for example, modulating immunogenicity: methods of increasing water solubility, bioavailability, serum half-life, and/or therapeutic half-life; and/or modulating biological activity. Certain modifications can also be useful to, for example, raise of antibodies for use in detection assays (e.g., epitope tags) and to provide for ease of protein purification. In some embodiments, the modified IL-2 mutein is at least 95, 96, 97, 98, or 99% identical to SEQ ID NO:5 and has a one of the combinations of three modifications relative to SEQ ID NO:5 as set forth in Table 2. Algorithms that are suitable for determining percent sequence identity and sequence similarity are the BLAST and BLAST 2.0 algorithms, which are described in Altschul et al. (1990) *J. Mol. Biol.* 215:403-410 and Altschul et al. (1977) *Nucleic Acids Res.* 25:3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues: always >0) and N (penalty score for mismatching residues: always <0). For amino acid sequences, a scoring matrix is used to calculate the cumulative score. Extension of the word hits in each direction are halted when: the cumulative alignment score falls off by the quantity X from its maximum achieved value: the cumulative score goes to zero or below; due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

Modulate: As used herein, the terms "modulate", "modulation" and the like refer to the ability of a test agent to affect a response, either positive or negative or directly or indirectly, in a system, including a biological system or biochemical pathway.

Mutein: As used herein, the term "mutein" is used to refer to modified versions of wild type polypeptides comprising modifications to the primary structure (i.e. amino acid sequence) of such polypeptide. The term mutein may refer to the polypeptide itself, a composition comprising the polypeptide, or a nucleic acid sequence that encodes it. In some embodiments, the mutein polypeptide comprises from about one to about ten amino acid modifications relative to the parent polypeptide, alternatively from about one to about five amino acid modifications compared to the parent, alternatively from about one to about three amino acid modifications compared to the parent, alternatively from one to two amino acid modifications compared to the parent, alternatively a single amino acid modification compared to the parent. A mutein may be at least about 99% identical to the parent polypeptide, alternatively at least about 98% identical, alternatively at least about 97% identical, alternatively at least about 95% identical, or alternatively at least about 90% identical.

N-Terminus: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Numbered in accordance with IL-2: The term "numbered in accordance with IL-2" as used herein refers to the identification of a location of particular amino acid with reference to the position at which that amino acid normally occurs in the mature sequence of the mature wild type hIL-2, for example R81 refers to the eighty-first amino acid, arginine, that occurs in SEQ ID NO:5.

Operably Linked: The term "operably linked" is used herein to refer to the relationship between nucleic acid sequences encoding differing functions when combined into a single nucleic acid sequence that, when introduced into a cell, provides a nucleic acid which is capable of effecting the transcription and/or translation of a particular nucleic acid sequence in a cell. For example, DNA for a signal sequence is operably linked to DNA for a polypeptide if it is expressed as a preprotein that participates in the secretion of the polypeptide: a promoter or enhancer is operably linked to a coding sequence if it affects the transcription of the sequence: or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, certain genetic elements such as enhancers need not be contiguous with respect to the sequence to which they provide their effect.

Parent Polypeptide: As used herein the terms "parent polypeptide", "parent protein", "precursor polypeptide", or "precursor protein" are used interchangeably to refer to unmodified polypeptide that is subsequently modified to generate a variant polypeptide or mutein. A parent polypeptide may be a wild type (or native) polypeptide.

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Clinically, partial agonists can be used to activate receptors to give a desired submaximal response when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. An IL-2 partial agonist of the present disclosure may have greater than 10%, alternatively greater than 20%, alternatively greater than 30%, alternatively greater than 40%, alternatively greater than 50%, alternatively greater than 60%, or alternatively greater than 70% of the activity of WHO International Standard (NIBSC code: 86/500) wild type mature human IL-2 when evaluated at similar concentrations in a comparable assay.

PEG-IL2 mutein: As used herein the term "PEG-IL2 mutein" refers to an IL2 mutein covalently bound to at least one polyethylene glycol (PEG) molecule, the at least one PEG molecule being covalently attached to at least one amino acid residue of an IL-2 mutein. The PEGylated polypeptide may be further referred to as monopegylated, dipegylated, tripegylated (and so forth) to denote PEG-IL2 muteins comprising one, two, three (or more) PEG moieties attached to the IL-2 mutein, respectively. In some embodiments, the PEG may be covalently attached directly to the IL-2 mutein (e.g., through a lysine side chain, sulfhydryl group of a cysteine or N-terminal amine) or optionally employ a linker between the PEG and the IL-2 mutein. In some embodiments the PEG-IL2 mutein comprises more than one PEG molecule each of which is attached to a different amino acid residue. In some embodiments, the PEG-IL2 mutein is derived from Sequence ID NO: 2 (naturally occurring hIL2). PEGylated forms of IL2 and the methodology of PEGylation of IL2 polypeptides is well known in the art (see, e.g., Katre, et al U.S. Pat. No. 4,931,544 issued Jun. 5, 1990; Katre, et al., U.S. Pat. No. 5,206,344 issued Apr. 27, 1993; and Bossard, et al., U.S. Pat. No. 9,861,705 issued Jan. 9, 2018) In some embodiments, the IL2 mutein may be modified by the incorporation of non-natural amino acids with non-naturally occurring amino acid side chains to facilitate site specific PEGylation as described in Ptacin, et al. United States Patent Application Publication US20170369871A1 published Dec. 28, 2017. In other embodiments, cysteine residues may be incorporated at various positions within the IL2 molecule to facilitate site-specific PEGylation via the cysteine side chain as described in Greve, et al. PCT International Patent Application Number PCT/US2015/044462 published as WO2016/025385 on Feb. 18, 2016.

Polypeptide: As used herein the terms "polypeptide." "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence: fusion proteins with heterologous and homologous leader sequences: fusion proteins with or without N-terminus methionine residues: fusion proteins with immunologically tagged proteins: fusion proteins of immunologically active proteins (e.g. antigenic diphtheria or tetanus toxin fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed due to genetic, experiential or environmental factors to having a particular disease, disorder or condition. In certain instances, the terms "prevent", "preventing", "prevention" are also used to refer to the slowing of the progression of a disease, disorder or condition from a present its state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a "soluble" receptor that is not associated with a cell surface. The soluble form of hCD25 is an example of a soluble receptor that specifically binds hIL2. In some embodiments, the receptor is a cell surface receptor that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of the ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface molecule having not associated with any intracellular signaling alone but upon ligand binding facilitates the formation of a heteromultimeric including heterodimeric (e.g. the intermediate affinity CD122/CD132 IL2 receptor), heterotrimeric (e.g. the high affinity CD25/CD122/CD132 hIL2 receptor) or homomultimeric (e.g. homodimeric, homotrimeric, homotetrameric) complex that results in the activation of an intracellular signaling cascade (e.g. the Jak/STAT pathway).

Recombinant: As used herein, the term recombinant to refer to polypeptides generated using recombinant DNA technology. The techniques and protocols for recombinant DNA technology are well known in the art.

Response: As used herein, the term "response," refers, for example, to a cell, tissue, organ, or organism, and encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors: whereas the terms "inhibition", "down-regulation" and the like refer to the opposite effects.

Selective: As used herein, the term "selective" is used to refer to a property of an agent to preferentially bind to and/or activate a particular cell type based on a certain property of a population of such cells. In some embodiments, the disclosure provides muteins that are CD25 selective in that such muteins display preferential activation of cells that expressing the CD25 and/or CD25/CD122 receptors relative to the cells expressing the CD132 receptor. Selectivity is typically assessed by activity measured in an assay characteristic of the activity induced in response to ligand/receptor binding. In some embodiments, the selective IL2 mutein exhibits significantly reduced binding. In some embodiments, selectivity is measured by activation of cells expressing CD25 (e.g. YTCD25POS or $YT^{CD25+}$ cells) versus the activation of that display significantly lower (preferably undetectable) levels of CD25 (e.g. YTCD25NEG or $YT^{CD25-}$ cells). In some embodiments, the selectivity is measured by activation of T cells expressing CD25 (e.g. Tregs) versus low levels of CD25 (e.g. non stimulated CD8+ or CD4+ T cells). In some embodiments, IL2 muteins of the present disclosure possess at least 3 fold, alternatively least 5 fold, alternatively at least 10 fold, alternatively at least 20 fold, alternatively at least 30 fold, alternatively at least 40 fold, alternatively at least 50 fold, alternatively at least 100 fold, alternatively at least 200 fold difference in EC50 on CD25+ versus CD25− cells as measured in the same assay.

Significantly Reduced Binding: As used herein, the term "exhibits significantly reduced binding" is used with respect to the affinity of the binding of the modified ligand (e.g., an IL2 mutein or modified IL2 mutein) to a receptor relative to the binding of a naturally occurring form of such ligand for such cognate receptor. A IL2 mutein exhibits significantly reduced binding if the IL2 mutein binds to the native form of the receptor with less than 40%, alternatively less than about 30%, alternatively less than about 20%, alternatively less than about 10%, alternatively less than about 5%, alternatively less than about 2%, alternatively less than about 1% of the naturally occurring ligand.

Specifically Binds: As used herein the term "specifically binds" refers to the degree of selectivity or affinity for which one molecule binds to another. In the context of binding pairs (e.g. a ligand/receptor, antibody/antigen, antibody/ligand, antibody/receptor binding pairs) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the second molecule of the binding pair (e.g. a protein, antigen, ligand, or receptor) if the equilibrium dissociation constant between antibody and to the second molecule of the binding pair is greater than about $10^6$M, alternatively greater than about $10^8$ M, alternatively greater than about $10^{10}$ M, alternatively greater than about $10^{11}$ M, alternatively greater than about $10^{10}$ M, greater than about $10^{12}$ M as determined by, e.g., Scatchard analysis (Munsen, et al. 1980) Analyt. Biochem. 107:220-239). In one embodiment where the ligand is an IL2 mutein and the receptor comprises an orthogonal CD122 ECD, the IL2 mutein specifically binds if the equilibrium dissociation constant of the IL2 mutein/orthogonal CD122 ECD is greater than about $10^5$M, alternatively greater than about $10^6$ M, alternatively greater than about $10^7$M, alternatively greater than about $10^8$M, alternatively greater than about $10^9$ M, alternatively greater than about $10^{10}$ M, or alternatively greater than about $10^{11}$ M. Specific binding may be assessed using techniques known in the art including but not limited to competition ELISA, radioactive ligand binding assays (e.g., saturation binding, Scatchard plot, nonlinear curve fitting programs and competition binding assays): non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore S200, Biacore T200 (GE Healthcare Bio-Sciences, 100 Results Way, Marlborough MA 01752)): liquid phase ligand binding assays (e.g., real-time polymerase chain reaction (RT-qPCR), and immunoprecipitation); and solid phase ligand binding assay's (e.g., multiwell plate assays, on-bead ligand binding assays, on-column ligand binding assays, and filter assays).

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Suffering From: As used herein, the term "suffering from" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment. The term suffering from is typically used in conjunction with a particular disease state such as "suffering from an inflammatory, infectious or autoimmune diseases, disorders or conditions disease" refers to a subject which has been diagnosed with the presence of an inflammatory, infectious or autoimmune disease, disorder or condition.

Substantially Pure: As used herein in the term "substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve $CD8^+$ T cells, cytotoxic $CD8^+$ T cells, naïve $CD4^+$ T cells, helper T cells, e.g. $T_H1$, $T_H2$, $T_H9$, $T_H11$, $T_H22$, $T_{FH}$: regulatory T cells, e.g. $T_R1$, Tregs, inducible Tregs: memory T cells, e.g. central memory T cells, effector memory T cells, NKT cells, tumor infiltrating lymphocytes (TILs) and engineered variants of such T-cells including but not limited to CAR-T cells, recombinantly modified TILs and TCR engineered cells.

Therapeutically Effective Amount: The phrase "therapeutically effective amount" as used herein in reference to the administration of an agent to a subject, either alone or as part of a pharmaceutical composition or treatment regimen, in a single dose or as part of a series of doses in an amount capable of having any detectable, positive effect on any symptom, aspect, or characteristic of a disease, disorder or condition when administered to the subject. The therapeutically effective amount can be ascertained by measuring relevant physiological effects, and it may be adjusted in connection with a dosing regimen and in response to diagnostic analysis of the subject's condition, and the like. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, biomarkers (such as inflammatory cytokines, IFN-γ, granzyme, and the like), reduction in serum tumor markers, improvement in Response Evaluation Criteria In Solid Tumors (RECIST), improvement in Immune-Related Response Criteria (irRC), increase in duration of survival, extended duration of progression free survival, extension of the time to progression, increased time to treatment failure. extended duration of event free survival, extension of time to next treatment, improvement objective response rate, improvement in the duration of response, reduction of tumor burden, complete response, partial response, stable disease, and the like that that are relied upon by clinicians in the field for the assessment of an improvement in the condition of the subject in response to administration of an agent. As used herein the terms "Complete Response (CR)." "Partial Response (PR)" "Stable Disease (SD)" and "Progressive Disease (PD)" with respect to target lesions and the terms "Complete Response (CR)." "Incomplete Response/Stable Disease (SD)" and Progressive Disease (PD) with respect to non-target lesions are understood to be as defined in the RECIST criteria. As used herein the terms "immune-related Complete Response (irCR)," "immune-related Partial Response (irPR)," "immune-related Progressive Disease (irPD)" and "immune-related Stable Disease (irSD)" as as defined in accordance with the Immune-Related Response Criteria (irRC). As used herein, the term "Immune-Related Response Criteria (irRC)" refers to a system for evaluation of response to immunotherapies as described in Wolchok, et al. (2009) *Guidelines for the Evaluation of Immune Therapy Activity in Solid Tumors: Immune-Related Response Criteria*, Clinical Cancer Research 15 (23): 7412-7420. A therapeutically effective amount may be adjusted over a course of treatment of a subject in connection with the dosing regimen and/or evaluation of the subject's condition and variations in the foregoing factors. In one embodiment, a therapeutically effective amount is an amount of an agent when used alone or in combination with another agent does not result in non-reversible serious adverse events in the course of administration to a mammalian subject.

Transmembrane Domain: The term "transmembrane domain" or "TM" refers to the domain of a membrane spanning polypeptide (e.g. a membrane spanning polypetide such as CD122 or CD132 or a CAR) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments the transmembrane domain is the transmembrane domain natively associated with the ECD domain of the cognate receptor from which the orthogonal receptor is derived. In some embodiments the transmembrane domain is the transmembrane domain natively associated with the ICD domain of the cognate receptor from which the orthogonal receptor is derived. In some embodiments the transmembrane domain is the transmembrane domain natively associated with the proliferation signaling domain. In some embodiments the transmembrane domain is the transmembrane domain natively associated with a different protein. Alternatively, the transmembrane domain of the receptor may be an artificial amino acid sequence which spans the plasma membrane. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treat: The terms "treat", "treating", treatment" and the like refer to a course of action (such as administering an IL-2 mutein, or a pharmaceutical composition comprising same) initiated with respect to a subject after a disease, disorder or condition, or a symptom thereof, has been diagnosed, observed, or the like in the subject so as to eliminate, reduce, suppress, mitigate, or ameliorate, either temporarily or permanently, at least one of the underlying causes of such disease, disorder, or condition afflicting a subject, or at least one of the symptoms associated with such disease, disorder, or condition. The treatment includes a course of action taken with respect to a subject suffering from a disease where the course of action results in the inhibition (e.g., arrests the development of the disease, disorder or condition or ameliorates one or more symptoms associated therewith) of the disease in the subject.

Treg Cell or Regulatory T Cell. The terms "regulatory T cell" or "Treg cell" as used herein refers to a type of $CD4^+$ T cell that can suppress the responses of other T cells including but not limited to effector T cells (Teff). Treg cells are characterized by expression of CD4, the a-subunit of the IL-2 receptor (CD25), and the transcription factor forkhead box P3 (FOXP3) (Sakaguchi, Annu Rev Immunol 22, 531-62 (2004). By "conventional $CD4^+$ T cells" is meant $CD4^+$ T cells other than regulatory T cells.

Variant: The terms "protein variant" or "variant protein" or "variant polypeptide" are used interchangeably herein to refer to a polypeptide that differs from a parent polypeptide by virtue of at least one amino acid modification. The parent polypeptide may be a naturally occurring or wild type (WT) polypeptide or may be a modified version of a WT polypeptide (i.e. mutein).

Wild Type: By "wild type" or "WT" or "native" herein is meant an amino acid sequence or a nucleotide sequence that is found in nature, including allelic variations. A wild type protein, polypeptide, antibody, immunoglobulin, IgG, etc. has an amino acid sequence or a nucleotide sequence that has not been modified by the hand of man.

In some embodiments, the IL2 muteins of the present disclosure provide modifications that modify the binding of the IL2 mutein to other proteins, in particular CD25, CD122 and CD132 as well as combinations of such proteins such as CD122/CD132 (the "intermediate affinity IL2 receptor"), CD25 (the "low affinity IL2 receptor") and CD25/CD122/CD132 (the "high affinity IL2 receptor").

The present disclosure provides methods and compositions for the treatment and/or prevention of inflammatory, infectious or autoimmune diseases, disorders or conditions by the administration of a therapeutically effective amount of an human IL-2 muteins that have decreased binding affinity for CD132 yet retain significant binding affinity for CD122 and/or CD25 comparable to the affinity of wild-type human IL-2.

In some embodiments, the IL-2 muteins possess decreased binding affinity to the extracellular domain of hCD132 (e.g, <50% the affinity of wild type hIL2, alternatively <45% the affinity of wild type hIL2, alternatively <40% the affinity of wild type IL2, alternatively <35% the affinity of wild type hIL2, alternatively <25% the affinity of wild type hIL2, alternatively <20% the affinity of wild type hIL2, alternatively <15% the affinity of wild type IL2, alternatively <10% the affinity of wild type IL2, or alternatively <5% the affinity of wild type IL2) while retaining substantial affinity (e.g., 20% the affinity of wild type hIL2, alternatively >30% the affinity of wild type hIL2, alternatively >40%, alternatively >50% the affinity of wild type hIL2, alternatively >60% the affinity of wild type hIL2, alternatively >65% the affinity of wild type hIL2, alternatively >70% the affinity of wild type hIL2, alternatively >75% the affinity of wild type hIL2, alternatively >80% the affinity of wild type hIL2, alternatively >85% the affinity of wild type hIL2, alternatively >90% the affinity of wild type IL2, alternatively >90% the affinity of wild type IL2, alternatively >95% the affinity of wild type IL2, alternatively >100% the affinity of wild type IL2, alternatively >105% the affinity of wild type hIL2, alternatively >110% the affinity of wild type IL2, alternatively >115% the affinity of wild type hIL2, alternatively >125% the affinity of wild type IL2, or alternatively >150% the affinity of wild type hIL2) binding affinity for the extracellular domain of the wild type human CD122 receptor.

In some embodiments, the IL-2 mutein useful in the practice of the methods of the present disclosure having a reduced binding affinity for CD132 receptor further includes 1, 2, 3, 4, 5, 6, 7, 8, 9, or 10 or more mutations that increase CD122 binding affinity. In certain embodiments, the subject IL-2 mutein useful in the practice of the methods of the present disclosure includes at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild type IL-2 (e.g., SEQ ID NO:5), and binds the CD122 with higher affinity than a wild type IL-2. In certain embodiments, the IL-2 mutein binds CD122 with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% greater than wild type IL-2. The binding affinity of IL-2 mutein can also be expressed as 1.2, 1.4, 1.5, 2, 5, 10, 15, 20, 25, 50, 100, 200, 250 or more fold greater affinity for the CD122 than wild type hIL-2.

In some embodiments, the IL-2 muteins possess decreased binding affinity to the extracellular domain of hCD132 (e.g. <50% the affinity of wild type hIL2, alternatively <45% the affinity of wild type hIL2, alternatively <40% the affinity of wild type hIL2, alternatively <35% the affinity of wild type hIL2, alternatively <25% the affinity of wild type hIL2, alternatively <20% the affinity of wild type hIL2, alternatively <15% the affinity of wild type hIL2, alternatively <10% the affinity of wild type hIL2, or alternatively <5% the affinity of wild type hIL2) while retaining substantial affinity (e.g. >50% the affinity of wild type hIL2, alternatively >60% the affinity of wild type hIL2, alternatively >65% the affinity of wild type hIL2, alternatively >70% the affinity of wild type hIL2, alternatively >75% the affinity of wild type hIL2, alternatively >80% the affinity of wild type hIL2, alternatively >85% the affinity of wild type hIL2, alternatively >90% the affinity of wild type hIL2, alternatively >90% the affinity of wild type hIL2, alternatively >95% the affinity of wild type hIL2, alternatively >100% the affinity of wild type hIL2, alternatively >105% the affinity of wild type hIL2, alternatively >110% the affinity of wild type hIL2, alternatively >115% the affinity of wild type hIL2, alternatively >125% the affinity of wild type hIL2, or alternatively >150% the affinity of wild type IL2) ine the hCD25/hCD122 receptor complex. In certain embodiments, the IL2 muteins of the present disclosure possess reduced affinity for CD132. In some embodiments, such IL2 muteins incorporate modifications to the primary structure of the wild type IL2 incorporating one or more modifications at positions 18, 22, and 126 numbered in accordance with wild type hIL-2.

In some embodiments, the IL-2 muteins possess decreased binding affinity to CD132 while retaining substantial affinity (e.g. >50% the affinity of wild type hIL2, alternatively >60% the affinity of wild type hIL2, alternatively >65% the affinity of wild type hIL2, alternatively >70% the affinity of wild type hIL2, alternatively >75% the affinity of wild type hIL2, alternatively >80% the affinity of wild type hIL2, alternatively >85% the affinity of wild type hIL2, alternatively >90% the affinity of wild type hIL2, alternatively >90% the affinity of wild type IL2, alternatively >95% the affinity of wild type hIL2, alternatively >100% the affinity of wild type IL2, alternatively >105% the affinity of wild type hIL2, alternatively >110% the affinity of wild type hIL2, alternatively >115% the affinity of wild type hIL2, alternatively >125% the affinity of wild type hIL2, alternatively >150% the affinity of wild type hIL2, alternatively >200% the affinity of wild type hIL2, alternatively >300% the affinity of wild type IL2, alternatively >400% the affinity of wild type hIL2, alternatively >500% the affinity of wild type IL2) binding affinity for hCD25.

In one aspect, the present disclosure provides hIL-2 muteins exhibiting significant or enhanced binding affinity for hCD25 and reduced binding affinity for the extracellular domain of hCD132 receptor as compared to wild type human IL-2 (hIL-2).

In some embodiments, the IL-2 muteins comprise one or more amino acid substitutions that decrease CD132 receptor binding affinity selected from amino acid positions 18, 22, and 126, numbered in accordance with mature wild type hIL-2.

In some embodiments, the subject IL-2 muteins useful in the practice of the methods of the present disclosure that are partial agonists have one or more reduced functions as compared to wild type IL-2.

In certain embodiments, the IL-2 muteins useful in the practice of the methods of the present disclosure disrupt the association of the CD122 with the CD132 such that this CD122/CD132 interaction is reduced by about 2%, about 5%, about 10%, about 15%, about 20%, about 50%, about 75%, about 90%, about 95% or more relative to wild type hIL-2. In some embodiments, the one or more mutations reducing the binding affinity of the IL-2 mutein for CD132 is an amino acid substitution. In some embodiments, the subject hIL-2 mutein consists of 1, 2, 3, 4, 5, 6, 7, 8, 9, 10, 11, 12, 13, 14, or 15 amino acid substitutions as compared to a wild type IL-2 (SEQ ID NO:5).

In certain embodiments the IL2 mutein useful in the practice of the methods of the present disclosure is an inhibitor of IL-2 and/or IL-15 phosphorylation in CD8+ T cells. In some embodiments, the mutein is an inhibitor of IL-2 and/or IL-15 induced proliferation of CD8+ T cells. In some embodiments, the mutein is an inhibitor of IL-2 dependent, TCR-induced cell proliferation.

In certain embodiments the IL2 mutein useful in the practice of the methods of the present disclosure is an inhibitor of IL-2 dependent activation of natural killer (NK) cells. IL-2 activation of NK cells can be measured by any suitable method known in the art, for example, by measuring IL-2 induced CD69 expression and/or cytotoxicity, as described herein.

In some embodiments of the disclosure, the IL-2 muteins are partial agonists. In certain embodiments, the IL-2 mutein useful in the practice of the methods of the present disclosure is a partial agonist has reduced capabilities to stimulate one or more signaling pathways that are dependent on CD122/CD132 heterodimerization. In some embodiments, the subject IL-2 mutein has a reduced capability to stimulate phosphorylation in an CD122+ cell as compared to wild type hIL-2. In some embodiments, the IL-2 mutein stimulates STAT5 phosphorylation in an IL-2RP+ cell at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild type IL-2 stimulates STAT5 phosphorylation in the same cell. In some embodiments, the IL-2Rp+ cell is a T cell. In particular embodiments, the T cell is a CD8+ T cell. In some embodiments, the CD8+ T cell is a freshly isolated CD8+ T cell. In other embodiments, the CD8+ T cell is an activated CD8+ T cell. In other embodiments, the CD122+ cell is a natural killer (NK) cell.

In some embodiments, the IL2 mutein useful in the practice of the methods of the present disclosure is a partial agonist has a reduced capability to stimulate signaling in an CD122+ cell as compared to wild type hIL-2. In some embodiments, the IL-2 mutein stimulates pERK1/ERK2 signaling in an CD122+ cell at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild type IL-2 stimulates pERK1/ERK2 signaling in the same cell. In some embodiments, the CD122+ cell is a T cell. In particular embodiments, the CD122+ T cell is a CD8+ T cell. In some embodiments, the CD122+ CD8+ T cell is a CD122+ CD8+ T cell isolated from a subject. In other embodiments, the CD8+ T cell T cell is an activated CD122+ CD8+ T cell. In other embodiments, the CD122+ cell is a natural killer (NK) cell. STAT5 and ERK1/2 signaling can be measure, for example, by phosphorylation of STAT5 and ERK1/2 using any suitable method known in the art. For example, STAT5 and ERK1/2 phosphorylation can be measured using antibodies specific for the phosphorylated version of these molecules in In certain embodiments, the mutein useful in the practice of the methods of the present disclosure is a partial agonist having has a reduced capability to induce lymphocyte proliferation as compared to wild type hIL-2. In some embodiments, the lymphocyte is a T cell. In particular embodiments, the lymphocyte is a primary CD8+ T cell. In other embodiments, the lymphocyte is an activated CD8+ T cell. Cell proliferation can be measured using any suitable method known in the art. For example, lymphocyte proliferation can be measured using a carboxyfluorescein diacetate succinimidyul diester (CFSE) dilution assay or by [31-1]-thymidine incorporation, as described herein. In some embodiments, an IL-2 mutein of the present disclosure induces lymphocyte proliferation at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild type hIL-2 induce lymphocyte proliferation.

In some embodiments, an IL-2 mutein of the present disclosure is a partial agonist that has a reduced capability to activate CD25 expression in a lymphocyte as compared to wild type IL-2. In some embodiments, the IL-2 mutein activates IL-2Ra expression in a lymphocyte at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild type IL-2 activates CD25 expression in the same cell. In some embodiments, the lymphocyte is a CD8+ T cell. In some embodiments, the CD8+ T-cell is a freshly isolated CD8+ T cell. In other embodiments, the CD8+ T cell is an activated CD8+ T cell.

In some embodiments of the disclosure, the IL-2 muteins are full agonists.

In some embodiments of the disclosure, the IL-2 muteins are super agonists.

In some embodiments, the disclosure methods and compositions for the treatment and/or prevention of inflammatory, infectious or autoimmune diseases, disorders or conditions diseases, disorders or conditions by the administration of a therapeutically effective amount of an human IL-2 muteins that have decreased binding affinity for CD132 yet retain significant binding affinity for CD122 and/or CD25 comparable to the activity of wild-type hIL2 in combination with a supplementary agents, including but not limited to one or more of chemotherapeutics, immune checkpoint modulators, radiotherapy and/or physical interventional treatment methods such as surgery.

In some embodiments, the present disclosure provides human interleukin-2 (IL-2) muteins providing modified binding properties to one or more IL2 receptors for the treatment of inflammatory, infectious or autoimmune diseases, disorders or conditions.

In various embodiments, the present disclosure provides polypeptides comprising the amino acid sequence according to the following formula 1:

Formula 1 (SEQ ID NO: 97)

$$\left[ \begin{array}{c} (AA1)_a\text{-}(AA2)_b\text{-}(AA3)_c\text{-}(AA4)_d\text{-}(AA5)_e\text{-}(AA6)_f\text{-}(AA7)_g\text{-}(AA8)_h\text{-} \\ (AA9)_i\text{-T10-Q11-L12-Q13-L14-E15-H16-L17-(AA18)-L19-D20-} \\ \text{L21-(AA22)-M23-I24-L25-N26-G27-I28-N29-N30-Y31-K32-N33-} \\ \text{P34-(AA35)-L36-T37-(AA38)-(AA39)-L40-T41-F42-K43-F44-} \\ \text{Y45-M46-P47-K48-K49-A50-T51-E52-L53-K54-(AA55)-L56-} \\ \text{Q57-C58-L59-E60-E61-E62-L63-K64-P65-L66-E67-E68-(AA69)-} \\ \text{L70-N71-L72-A73-(AA74)-S75-K76-N77-F78-H79-(AA80-} \\ \text{(AA81)-P82-R83-D84-(AA85)-(AA86)-S87-N88-(AA89)-N90-} \\ \text{(AA91)-(AA92)-V93-L94-E95-L96-(AA97)-G98-S99-E100-T101-} \\ \text{T102-F103-(AA104)-C105-E106-Y107-A108-(AA109)-E110-} \\ \text{T111-A112-(AA113)-I114-V115-E116-F117-L118-N119-R120-} \\ \text{W121-I122-T123-F124-(AA125)-(AA126)-S127-I128-I129-} \\ \text{(AA130)-T131-L132-T133} \end{array} \right]$$

wherein:

- each of a, b, c, d, e, f, g, h, and i is individually selected from 0 or 1;
- AA1 is A (wild type, a=1) or deleted (a=0);
- AA2 is P (wild type, b=1) or deleted (b=0);
- AA3 is T (wild type, c=1), C, A, G, Q, E, N, D, R, K, P, or deleted (c=0);
- AA4 is S (wild type, d=1) or deleted (d=0);
- AA5 is S (wild type, e=1) or deleted (e=0);
- AA6 is S (wild type, f=1) or deleted (f=0);
- AA7 is T (wild type, g=1) or deleted (g=0);
- AA8 is K (wild type, h=1) or deleted (h=0);
- AA9 is K (wild type, i=1) or deleted (i=0);
- AA18 is L (wild type) or R, L, G, M, F, E, H, W, K, Q, S, V, I, Y, H, D or T;
- AA22 is Q (wild type) or F, E, G, A, L, M, F, W, K, S, V, I, Y, H, R, N, D, T, or F;
- AA35 is K (wildtype) or E;
- AA38 is R (wild type), W or G;
- AA39 is M (wildtype), L or V;
- AA55 is H (wildtype) or Y;
- AA69 is V (wildtype) or A;
- AA74 is Q (wild type), P, N, H, S;
- AA80 is L (wild type), F or V;
- AA81 is R (wild type), I, D or T;
- AA85 is L (wild type) or V;
- AA86 is I (wild type) or V;
- AA89 is I (wild type) or V;
- AA91 is V (wild type), R or K;
- AA92 is I (wild type) or F;
- AA97 is K (wild type) or Q;
- AA104 is M (wild type) or A;
- AA109 is D (wildtype), C or a non-natural amino acid with an activated side chain;
- AA113 is T (wild type) or N;
- AA125 is C (wild type), A or S;
- AA126 is Q (wild type) or H, M, K, C, D, E, G, I, R, S, or T; and
- AA130 is S (wild type), T, G or R; and with the proviso that if AA18 is R and AA22 is E, then AA126 is not H, M, K, C, D, E, G, I, R, S, or T.

In certain embodiments, the disclosure provides IL2 muteins comprising the following mutations:

- AA18 is selected from the group consisting of L (wild type) or R, L, G, M, F, E, H, W, K, Q, S, V, I, Y, H, D or T;
- AA22 is selected from the group consisting of Q (wild type) or F, E, G, A, L, M, F, W, K, S, V, I, Y, H, R, N, D, T, or F; and
- AA126 is selected from the group consisting of Q (wild type) or H, M, K, C, D, E, G, I, R, S, or T, with the proviso that if AA18 is R and AA22 is E, then AA126 is not H, M, K, C, D, E, G, I, R, S, or T.

In certain embodiments, the disclosure provides IL2 muteins comprising the following mutations:

- a=0;
- AA18 is selected from the group consisting of L (wild type) or R, L, G, M, F, E, H, W, K, Q, S, V, I, Y, H, D or T;
- AA22 is selected from the group consisting of Q (wild type) or F, E, G, A, L, M, F, W, K, S, V, I, Y, H, R, N, D, T, or F; and
- AA126 is selected from the group consisting of Q (wild type) or H, M, K, C, D, E, G, I, R, S, or T.

with the proviso that if AA18 is R and AA22 is F or V, then AA126 is not H, M, K, C, D, E, G, I, R, S, or T.

In some embodiments, the present disclosure provides IL-2 mutein that comprises amino acid substitutions at amino acid positions 18, 22, and 126, numbered in accordance with wild type hIL-2 as described in Table 2 below. Note that the three-letter abbreviation for the particular IL2 mutein reflects an IL2 mutein having the mutations at positions 18, 22 and 126, for example "FEH" is shorthand nomenclature for an IL2 mutein comprising the substitutions L18F, Q22E and Q126H. In particular the IL2 muteins of the present disclosure comprise amino acid substitutions at positions 18 and/or 22, and 126 as described in Table 2 below:

TABLE 2

| IL2 Muteins | | | |
|---|---|---|---|
| | hIL2 Residue Position | | |
| | 18 | 22 | 126 |
| | wt hIL2 (SEQ ID NO 5) | | |
| | L | Q | Q |
| RQQ | R | Q(wt) | Q (wt) |
| LEQ | L (wt) | E | Q (wt) |
| LQH | L (wt) | Q(wt) | H |
| RQH | R | Q(wt) | H |
| LEH | L (wt) | E | H |
| GEH | G | E | H |
| AEH | A | E | H |
| MEH | M | E | H |
| FEH | F | E | H |
| WEH | W | E | H |
| KEH | K | E | H |
| QEH | Q | E | H |
| EEH | E | E | H |
| SHE | S | E | H |
| VEH | V | E | H |
| IEH | I | E | H |
| YEH | Y | E | H |
| HEH | H | E | H |
| NEH | N | E | H |
| DEH | D | E | H |
| TEH | T | E | H |

TABLE 2-continued

IL2 Muteins hIL2 Residue Position

| | 18 | 22 | 126 |
|---|---|---|---|
| | wt hIL2 (SEQ ID NO 5) | | |
| | L | Q | Q |
| RGH | R | G | H |
| RAH | R | A | H |
| RLH | R | L | H |
| RMH | R | M | H |
| RFH | R | F | H |
| RWH | R | W | H |
| RKH | R | K | H |
| RSH | R | S | H |
| RVH | R | V | H |
| RIH | R | I | H |
| RYH | R | Y | H |
| RHH | R | H | H |
| RRH | R | R | H |
| RNH | R | N | H |
| RDH | R | D | H |
| RTH | R | T | H |

Figure 2:
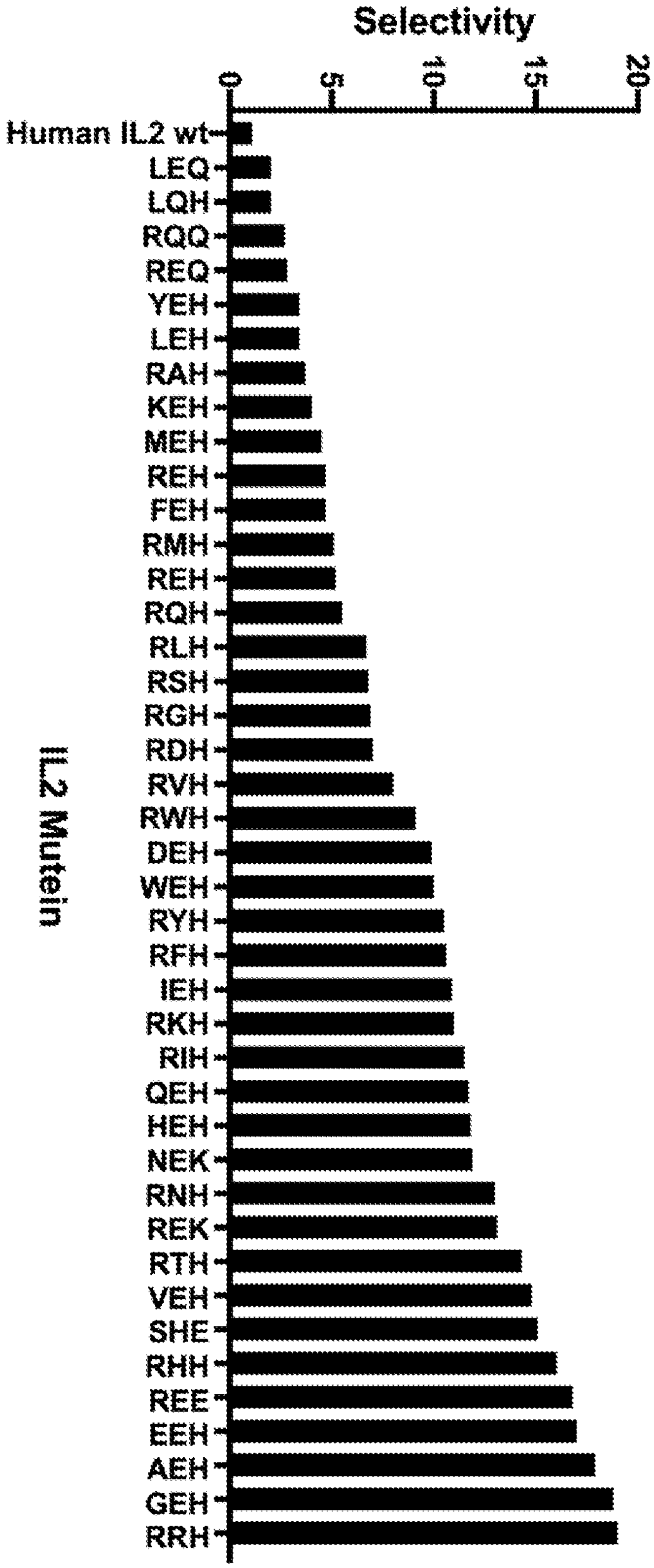
FIG. 2 provides comparative pSTAT5 activity in CD25 positive and CD25 negative YT cells treated with 293T transfection supernatant containing the indicated IL2 muteins (and controls) as described in the Examples. The vertical axis is a measure of selectivity calculated as the ratio of the level of pSTAT5 activity observed on CD25 positive YT cells divided by the level of pSTAT5 activity measured on CD25 negative YT cells and each bar indicates the level of activity of the particular IL2 peptide evaluated as identified by its 3 letter abbreviation as described in the Examples.
Figure 3B:
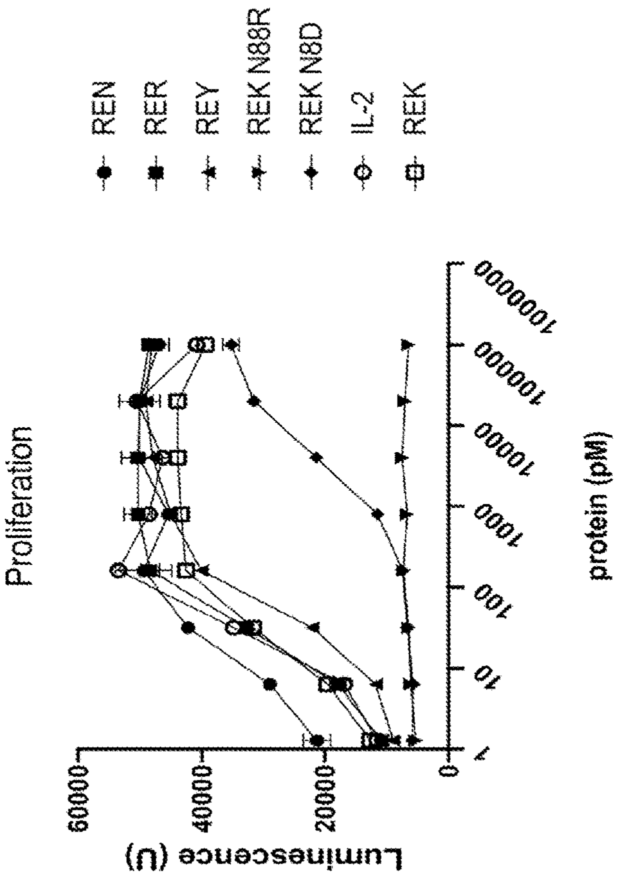
FIGS. 3A-3F provides data relating to the cell proliferation of 3F8 cells contacted with hIL2 muteins as more fully described in the specification and in Example 8.
Figure 3A:
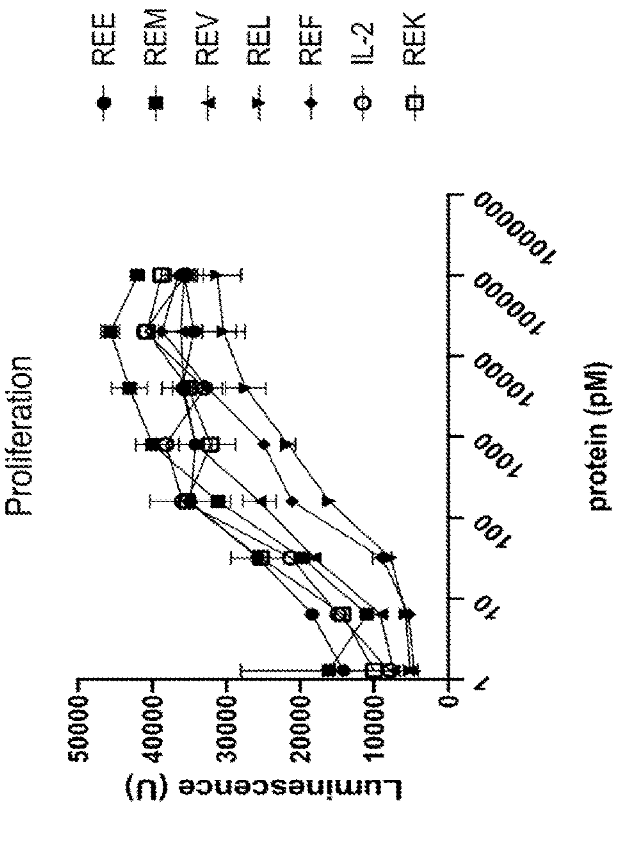
Figure 3C:
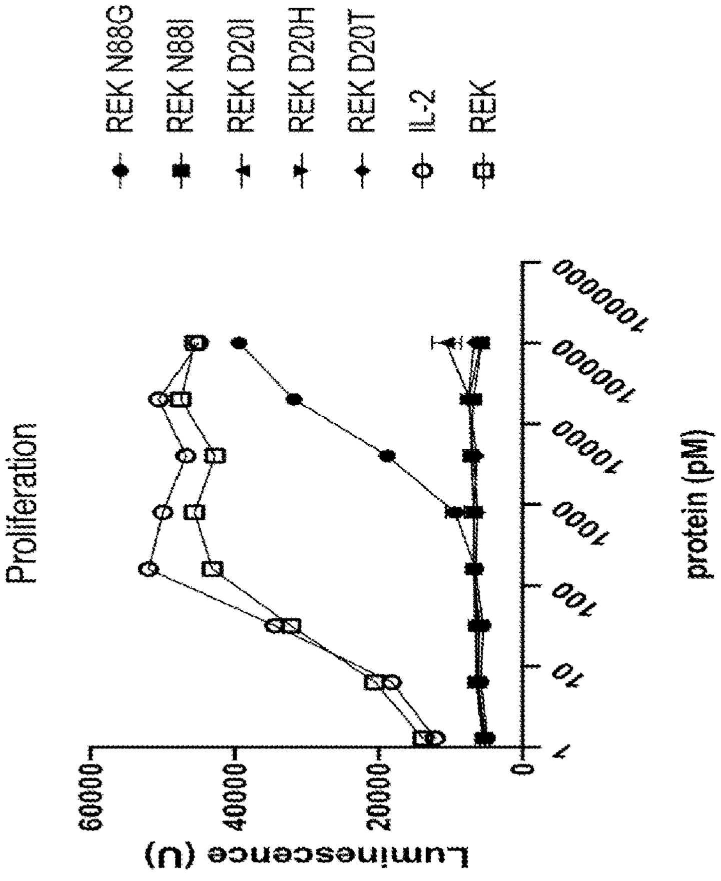
Figure 3D:
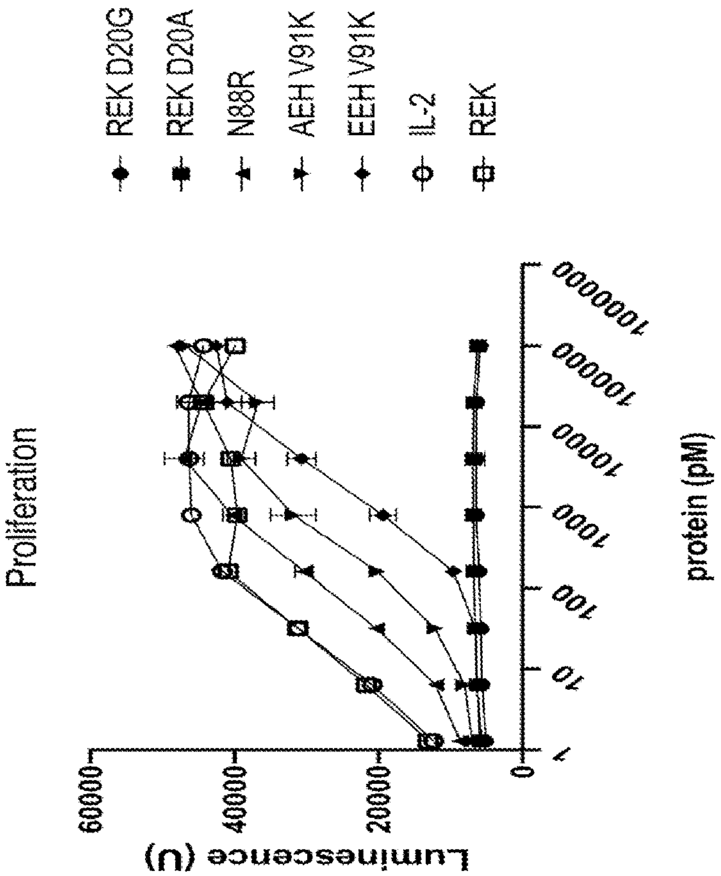
Figure 3E:
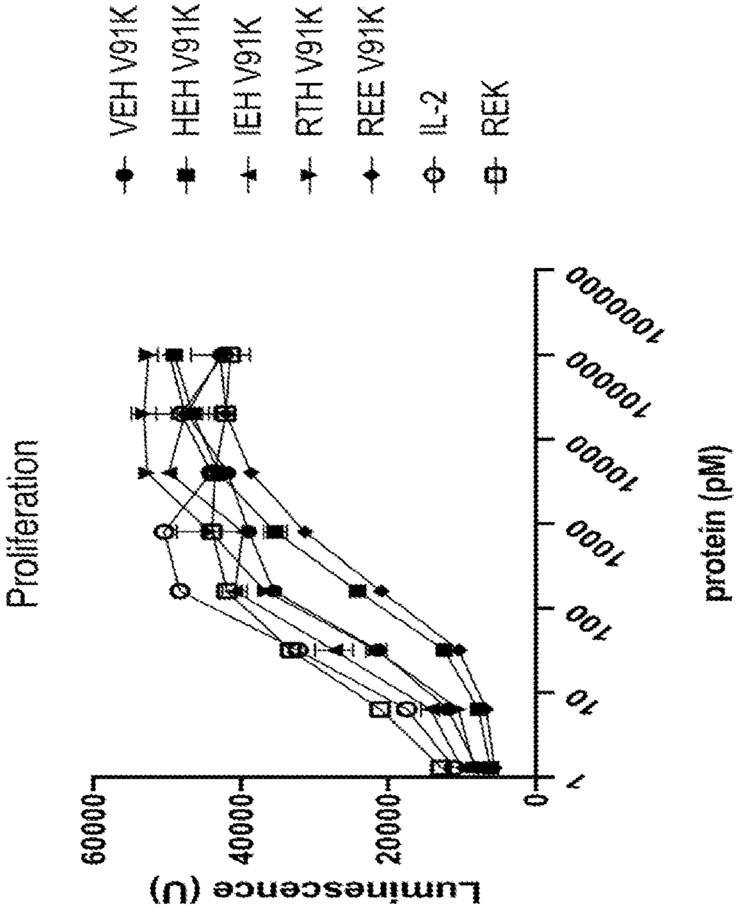
Figure 3F:
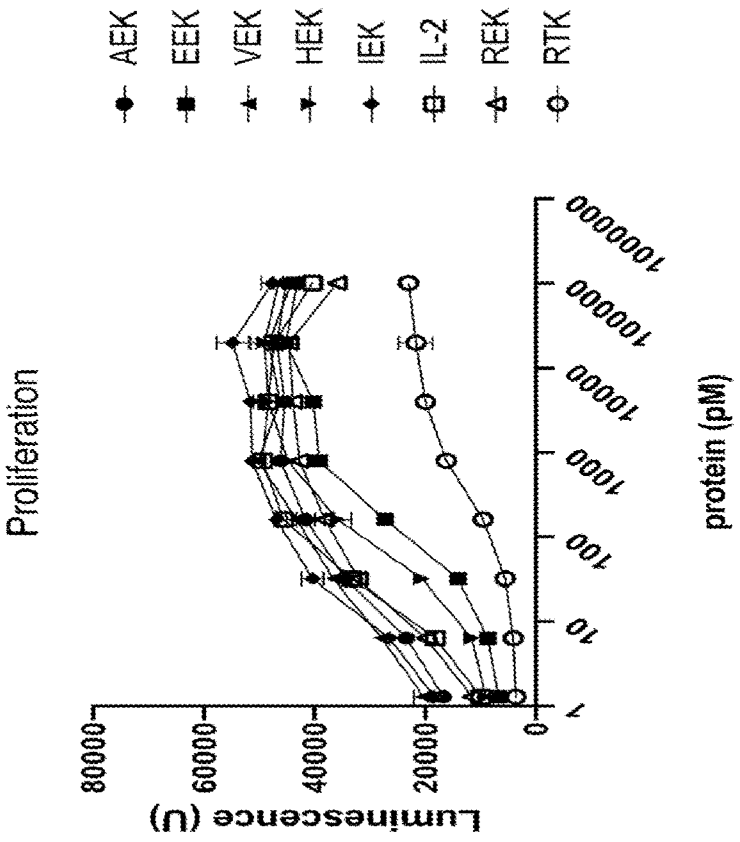

The foregoing IL2 muteins of Table 2 were prepared and tested in substantial accordance with the Examples herein. The results of the experiments are provided in FIGS. 1 and 2 of the attached drawings. As illustrated in FIG. 1, the IL2 muteins of the present invention retained significant IL2 activity. As illustrated in FIG. 2, the IL2 muteins of the present disclosure demonstrated significantly preferential activity on CD25 expressing cells relative to wild type IL2.

The IL2 muteins may also contain one more substitutions, deletions, or insertions within the wild type IL-2 amino acid sequence. The following nomenclature is used herein to refer to substitutions, deletions or insertions. Residues may be designated herein by the one-letter or three-letter amino acid code followed by the IL-2 amino acid position, e.g., "Cys125" or "C125" refers to the cysteine residue at position 125 of SEQ ID NO:5. Substitutions are designated herein by the one letter amino acid code followed by the IL-2 amino acid position followed by the Substituting one letter amino acid code, for example "K35A" refers to a substitution of the lysine (K) residue at position 35 of Sequence ID No. 5 with an alanine (A) residue. A deletion is referred to as "des" followed by the deleted amino acid residue and its position in SEQ ID NO:5. For example the term "des-Ala1" or "desA1" refers to the deletion of the alanine at position 1 of the polypeptide of SEQ ID NO:5.

Mutations to Increase CD122 Affinity

In some embodiments of the invention the IL2 muteins may comprise amino acid substitutions that enhance CD122 binding affinity. Examples of amino acid substitutions that enhance CD122 binding affinity include but are not limited to Q74N, Q74H, Q74S, L80F, L80V, R81D, R81T, L85V, 186V, 189V, and/or 192F or combinations thereof. In certain embodiments, the amino acid substitutions that increase CD122 binding affinity comprise: L80F, R81D, L85V, 186V and 192F. In some embodiments, the amino acid substitutions that increase CD122 binding affinity comprise: N74Q, L80F, R81D, L85V, 186V, 189V, and 192F. In some embodiments, the amino acid substitutions that increase CD122 binding affinity comprise: Q74N, L80V, R81T, L85V, 186V, and 192F. In certain embodiments, the amino acid substitutions that increase CD122 binding affinity comprise: Q74H, L80F, R81D, L85V, 186V and 192F. In some embodiments, the amino acid substitutions that increase CD122 binding affinity comprise: Q74S, L80F, R81D, L85V, 186V and 192F. In certain embodiments, the amino acid substitutions that increase CD122 binding affinity comprise: Q74N, L80F, R81D, L85V, 186V and 192F. In certain embodiments, the amino acid substitutions that increase CD122 binding affinity comprise: Q74S, R81T, L85V, and 192F.

In some embodiments, IL2 muteins may be affinity matured to enhance their affinity for CD25 and/or CD122. An "affinity matured" polypeptide is one having one or more alteration(s) in one or more residues which results in an improvement in the affinity of the orthogonal polypeptide for the cognate orthogonal receptor, or vice versa, compared to a parent polypeptide which does not possess those alteration(s). Affinity maturation can be done to increase the binding affinity of the IL2 mutein by at least about 10%, alternatively at least about 50%, alternatively at least about 100% alternatively at least about 150%, or from 1 to 5 fold as compared to the "parent" polypeptide.

Mutations to Increase CD25 Affinity:

In some embodiments, the IL-2 muteins contain one or more mutations in positions of the IL-2 sequence that either contact CD25 or alter the orientation of other positions contacting CD25 resulting in an IL2 mutein possessing increased affinity for CD25. In some embodiments, the IL2 muteins of the present disclosure comprise one or more the substitutions V69A and Q74P which have been described as increasing the binding affinity of IL2 for CD25.

Removal of Thr3 Glycosylation Site

The IL2 muteins of the present disclosure may further or optionally provide elimination of the O-glycosylation site at position Thr3 of the to facilitate the production of an aglycosylated IL2 mutein when the IL2 mutein expressed in mammalian cells such as CHO or HEK cells. Thus, in certain embodiments the IL2 mutein further comprise a modification which eliminates the O-glycosylation site of IL-2 at a position corresponding to residue 3 of human IL-2. In one embodiment said modification which eliminates the O-glycosylation site of IL-2 at a position corresponding to residue 3 of human IL-2 is an amino acid substitution. Exemplary amino acid substitutions include T3A, T3G, T3Q, T3E, T3N, T3D, T3R, T3K, T3S, T3C and T3P which removes the glycosylation site at position 3 without eliminating biological activity (see U.S. Pat. No. 5,116,943; Weiger et al., (1989) Eur. J. Biochem., 180:295-300). In a specific embodiment, said modification is the amino acid substitution T3A.

Minimizing Vascular Leak Syndrome

In some embodiments of the disclosure, the IL2 mutein may comprise amino acid substitutions to avoid vascular leak syndrome, a substantial negative and dose limiting side effect of the use of IL2 therapy in human beings without out substantial loss of efficacy. See, Epstein, et al., U.S. Pat. No. 7,514,073B2 issued Apr. 7, 2009. Examples of such modifications which are included in the IL2 muteins of the present disclosure include one or more of R38W, R38G, R39L, R39V, F42K, and H55Y.

Oxidation Resistance M104A

The IL2 muteins may optionally further comprise a modification at position M104, in one embodiment the substitution of methionine 104 with an alanine residue (M104A) to provide a more oxidation-resistant IL2 mutein (See Koths, et al. U.S. Pat. No. 4,752,585 issued Jun. 21, 1988).

Cys125

In some embodiments, the cysteine at position 125 is substituted with alanine or serine (C125A or C125S) to minimize potential misfolding of the protein when expressed recombinantly in bacteria and isolated from inclusion bodies as described in N Terminal Deletions When produced recombinantly in bacterial expression systems directly in the absence of a leader sequence, endogenous proteases result in the deletion of the N-terminal Met-Ala1 residues to provide "desAla1" IL2 muteins. In some embodiments, the present disclosure provides hIL2 muteins which are hIL2 polypeptides comprising one of the following sets of amino acid modifications:

IL2 muteins may comprise deletion of the first two amino acids (desAla1-desPro2) as well as substitution of the Thr3 glycosylation with a cysteine residue to facilitate for selective N-terminal modification, especially PEGylation of the sulfhydryl group of the cysteine (See, e.g. Katre, et al. U.S. Pat. No. 5,206,344 issued Apr. 27, 1993).

The IL2 muteins may further comprise elimination of N-terminal amino acids at one or more of positions 1-9 (compounds of the above formula where a, b, c, d, e, f, g, h, and i are all zero), alternatively positions 1-8 (compounds of the above formula where a, b, c, d, e, f, g, and h are all zero), alternatively positions 1-7 (compounds of the above formula where a, b, c, d, e, f, and g are all zero), alternatively positions 1-6 (compounds of the above formula where a, b, c, d, e, and f are all zero), alternatively positions 1-5 (compounds of the above formula where a, b, c, d, and e are all zero), alternatively positions 1-4 (compounds of the above formula where a, b, c and d are all zero), alternatively positions des1-3 (compounds of the above formula where a, b, and c are all zero), or alternatively positions 1-2 (compounds of the above formula where a and b are all zero) while retaining IL2 activity.

Conservative Amino Acid Substitutions

In some embodiments, the IL2 muteins of the present disclosure may further comprise one more conservative amino acid substitution within the wild type IL-2 amino acid sequence. Such conservative substitutions include those described by Dayhoff in The Atlas of Protein Sequence and Structure 5 (1978), and by Argos in EMBO J., 8:779-785 (1989). Conservative substitutions are generally made in accordance with the following chart depicted as Table 3.

TABLE 3

Exemplary Conservative Amino Acid Substitutions

| Wild type Residue | Substitution(s) |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu, Met, Leu, Ile |
| Phe | Met, Leu, Tyr, Trp |
| Ser | Thr |
| Thr | Ser |
| Trp | Tyr, Phe |
| Tyr | Trp, Phe |
| Val | Ile, Leu |

Substantial changes in function or immunological identity may be made by selecting amino acid substitutions that are less conservative than those indicated in Table 3. For example substitutions may be made which more significantly affect the structure of the polypeptide backbone or disrupt secondary or tertiary elements including the substitution of an amino acid with a small uncharged side chain (e.g. glycine) with a large charge bulky side chain (asparagine). In particular, substitution of those IL2 residues which are involved in the amino acids that interact with one or more of CD25, CD122 and/or CD123 as may be discerned from the crystal structure of IL2 in association with its receptors as described in Modifications to Extend Persistence In Vivo As discussed above, the compositions of the present disclosure include IL2 muteins that have been modified to provide for an extended lifetime in vivo and/or extended duration of action in a subject.

Primary Sequence Modifications

In some embodiments, the IL2 mutein may comprise certain amino acid substitutions that result in prolonged in vivo lifetime. For example, Dakshinamurthi, et al. (International Journal of Bioinformatics Research (2009) 1 (2): 4-13) state that one or more of the substitutions in the IL2 polypeptide V91R, K97E and T113N will result in an IL2 variant possessing enhanced stability and activity. In some embodiments, the IL2 muteins of the present disclosure comprise one, two or all three of the V91R, K97E and T113N modifications.

Conjugates and Carrier Molecules

In some embodiments the IL2 mutein is modified to provide an extended duration of action in a subject which may be achieve through conjugation to carrier molecules to provide desired pharmacological properties such as extended half-life. In some embodiments, the IL2 mutein can be covalently linked to the Fc domain of IgG, albumin, or other molecules to extend its half-life, e.g. by PEGylation, glycosylation, fatty acid acylation, and the like as known in the art. In some embodiments, the IL-2 conjugate comprises a plasma half-life in a human subject of greater than 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 10 days, 14 days, or 30 days.

Albumin Fusions

In some embodiments, the IL2 mutein is expressed as a fusion protein with an albumin molecule (e.g. human serum albumin) which is known in the art to facilitate extended exposure in vivo.

In one embodiment of the invention, the hIL2 analog is conjugated to albumin referred to herein as an "IL2 mutein albumin fusion." The term "albumin" as used in the context hIL2 analog albumin fusions include albumins such as human serum albumin (HSA), cyno serum albumin, and bovine serum albumin (BSA). In some embodiments, the HSA the HSA comprises a C34S or K573P amino acid substitution relative to the wild type HSA sequence According to the present disclosure, albumin can be conjugated to a hIL2 mutein at the carboxyl terminus, the amino terminus, both the carboxyl and amino termini, and internally (see, e.g., U.S. Pat. Nos. 5,876,969 and 7,056,701). In the HSA-hIL2 mutein polypeptide conjugates contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a hIL2 analog polypeptide fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker such as a peptide linker or modified version thereof as more fully discussed below:

Alternatively, the hIL2 analog albumin fusion comprises IL2 muteins that are fusion proteins which comprise an albumin binding domain (ABD) polypeptide sequence and an IL2 mutein polypeptide. As alluded to above, fusion proteins which comprise an albumin binding domain (ABD) polypeptide sequence and an hIL2 analog polypeptide can, for example, be achieved by genetic manipulation, such that the nucleic acid coding for HSA, or a fragment thereof, is joined to the nucleic acid coding for the one or more IL2 mutein sequences. In some embodiments, the albumin-binding peptide comprises the amino acid sequence DICL-PRWGCLW (SEQ ID NO:6).

The IL2 mutein polypeptide can also be conjugated to large, slowly metabolized macromolecules such as proteins: polysaccharides, such as sepharose, agarose, cellulose, or cellulose beads: polymeric amino acids such as polyglutamic acid, or polylysine: amino acid copolymers: inactivated virus particles: inactivated bacterial toxins such as toxoid from diphtheria, tetanus, cholera, or leukotoxin molecules: inactivated bacteria, dendritic cells, thyroglobulin: tetanus toxoid: Diphtheria toxoid: polyamino acids such as poly(D-lysine: D-glutamic acid): VP6 polypeptides of rotaviruses: influenza virus hemaglutinin, influenza virus nucleoprotein: Keyhole Limpet Hemocyanin (KLH); and hepatitis B virus core protein and surface antigen Such conjugated forms, if desired, can be used to produce antibodies against a polypeptide of the present disclosure.

In some embodiments, the IL2 mutein is conjugated (either chemically or as a fusion protein) with an XTEN which provides extended duration of akin to PEGylation and may be produced as a recombinant fusion protein in *E. coli.* XTEN polymers suitable for use in conjunction with the IL2 muteins of the present disclosure are provided in Podust, et al. (2016) "*Extension of in vivo half-life of biologically active molecules by XTEN protein polymers*", J Controlled Release 240:52-66 and Haeckel et al. (2016) "*XTEN as Biological Alternative to PEGylation Allows Complete Expression of a Protease-Activatable Killin-Based Cytostatic*" PLOS ONE|DOI: 10.1371/journal.pone.0157193 Jun. 13, 2016. The XTEN polymer may fusion protein may incorporate a protease sensitive cleavage site between the XTEN polypeptide and the IL2 mutein such as an MMP-2 cleavage site.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

PEGylation:

In some embodiments, the IL2 mutein is conjugated to one or more water-soluble polymers. Examples of water soluble polymers useful in the practice of the present invention include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol, polysaccharides, poly-alpha-hydroxy acid, polyvinyl alcohol (PVA), polyphosphazene, polyoxazolines (POZ), poly(N-acryloylmorpholine), or a combination thereof.

In some embodiments the IL2 mutein is conjugated to one or more polyethylene glycol molecules or "PEGylated." Although the method or site of PEG attachment to IL2 mutein may vary, in certain embodiments the PEGylation does not alter, or only minimally alters, the activity of the IL2 mutein.

In some embodiments, a cysteine may be substituted for the threonine at position 3 (3TC) to facilitate N-terminal PEGylation using particular chemistries.

In some embodiments, selective PEGylation of the IL2 mutein (for example by the incorporation of non-natural amino acids having side chains to facilitate selective PEG conjugation chemistries as described Ptacin, et al (PCT International Application No. PCT/US2018/045257 filed Aug. 3, 2018 and published Feb. 7, 2019 as International Publication Number WO 2019/028419A1 may be employed to generate an IL2 mutein with having reduced affinity for one or more subunits (e.g. CD25, CD132) of an IL2 receptor complex. For example, an hIL2 mutein incorporating non-natural amino acids having a PEGylatable specific moiety at those sequences or residues of IL2 identified as interacting with CD25 including amino acids 34-45, 61-72 and 105-109 typically provides an IL2 mutein having diminished binding to CD25. Similarly, an hIL2 mutein incorporating non-natural amino acids having a PEGylatable specific moiety at those sequences or residues of IL2 identified as interacting with hCD132 including amino acids 18, 22, 109, 126, or from 119-133 provides an IL2 mutein having diminished binding to hCD132.

In certain embodiments, the increase in half-life is greater than any decrease in biological activity. PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG used in the present disclosure is not restricted to any particular range. The PEG component of the PEG-IL2 mutein can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the invention, the PEG is a 40 kD branched PEG comprising two 20 kD arms.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons.

Two widely used first generation activated monomethoxy PEGs (mPEGs) are succinimdyl carbonate PEG (SC-PEG: see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

Pegylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

The PEG can be bound to an IL2 mutein of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxy succinylimide polyethylene glycol, which can be prepared by activating succinic acid ester of polyethylene glycol with N-hydroxysuccinylimide.

In some embodiments, the PEGylation of IL2 muteins is facilitated by the incorporation of non-natural amino acids bearing unique side chains to facilitate site specific PEGylation. The incorporation of non-natural amino acids into polypeptides to provide functional moieties to achieve site specific pegylation of such polypeptides is known in the art. See e.g. Ptacin, et al (PCT International Application No. PCT/US2018/045257 filed Aug. 3, 2018 and published Feb. 7, 2019 as International Publication Number WO 2019/028419A1. In one embodiment, the IL2 muteins of the present invention incorporate a non-natural amino acid at position D109 of the IL2 mutein. In one embodiment of the invention the IL2 mutein is a PEGylated at position 109 of the IL2 mutein to a PEG molecule having a molecular weight of about 20 kD, alternatively about 30 kD, alternatively about 40 kD.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present invention include a 10 kDa linear PEG-aldehyde (e.g., Sunbright®: ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g. Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 KDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

As previously noted, the PEG may be attached directly to the IL2 mutein or via a linker molecule. Suitable linkers include "flexible linkers" which are generally of sufficient length to permit some movement between the modified polypeptide sequences and the linked components and molecules. The linker molecules are generally about 6-50 atoms long. The linker molecules can also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Examples of flexible linkers include glycine polymers (G) n, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers (G) n, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the polypeptides disclosed herein.

Further, such linkers may be used to link the IL2 mutein to additional heterologous polypeptide components as described herein, the heterologous amino acid sequence may be a signal sequence and/or a fusion partner, such as, albumin, Fc sequence, and the like.

Acylation

In some embodiments, the IL2 mutein of the present disclosure may be acylated by conjugation to a fatty acid molecule as described in Resh (2016) Progress in Lipid Research 63:120-131. Examples of fatty acids that may be conjugated include myristate, palmitate and palmitoleic acid. Myristoylate is typically linked to an N-terminal glycine but lysines may also be myristoylated. Palmitoylation is typically achieved by enzymatic modification of free cysteine-SH groups such as DHHC proteins catalyze S-palmitoylation. Palmitoleylation of serine and threonine residues is typically achieved enzymatically using PORCN enzymes.

Acetylation

In some embodiments, the IL-2 mutein is acetylated at the N-terminus by enzymatic reaction with N-terminal acetyltransferase and, for example, acetyl COA. Alternatively, or in addition to N-terminal acetylation, the IL-2 mutein is acetylated at one or more lysine residues, e.g. by enzymatic reaction with a lysine acetyltransferase. See, for example Choudhary et al. (2009) Science 325 (5942): 834L2 ortho840.

Fc Fusions

In some embodiments, the IL2 fusion protein may incorporate an Fc region derived from the IgG subclass of antibodies that lacks the IgG heavy chain variable region. The "Fc region" can be a naturally occurring or synthetic polypeptide that is homologous to the IgG C-terminal domain produced by digestion of IgG with papain. IgG Fc has a molecular weight of approximately 50 kDa. The mutant IL-2 polypeptides can include the entire Fc region, or a smaller portion that retains the ability to extend the circulating half-life of a chimeric polypeptide of which it is a part. In addition, full-length or fragmented Fc regions can be variants of the wild type molecule. That is, they can contain mutations that may or may not affect the function of the polypeptides: as described further below, native activity is not necessary or desired in all cases. In certain embodiments, the IL-2 mutein fusion protein (e.g., an IL-2 partial agonist or antagonist as described herein) includes an IgG1, IgG2, IgG3, or IgG4 Fc region. Exemplary Fc regions can include a mutation that inhibits complement fixation and Fc receptor binding, or it may be lytic, i.e., able to bind complement or to lyse cells via another mechanism such as antibody-dependent complement lysis (ADCC).

In some embodiments, the IL2 mutein comprises a functional domain of an Fc-fusion chimeric polypeptide molecule. Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. The "Fc region" useful in the preparation of Fc fusions can be a naturally occurring or synthetic polypeptide that is homologous to an IgG C-terminal domain produced by digestion of IgG with papain. IgG Fc has a molecular weight of approximately 50 kDa. The IL2 muteins may provide the entire Fc region, or a smaller portion that retains the ability to extend the circulating half-life of a chimeric polypeptide of which it is a part. In addition, full-length or fragmented Fc regions can be variants of the wild type molecule. In a typical presentation, each monomer of the dimeric Fc carries a heterologous polypeptide, the heterologous polypeptides being the same or different.

In some embodiments, when the IL2 mutein is to be administered in the format of an Fc fusion, particularly in those situations when the polypeptide chains conjugated to each subunit of the Fc dimer are different, the Fc fusion may be engineered to possess a "knob-into-hole modification." The knob-into-hole modification is more fully described in Ridgway, et al. (1996) Protein Engineering 9 (7): 617-621 and U.S. Pat. No. 5,731,168, issued Mar. 24, 1998. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g. tyrosine or tryptophan) creating a projection from the surface ("knob") and ii) in the CH3 domain of a second heavy chain, an amino acid residue is replaced with an amino acid residue having a smaller side chain (e.g. alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g. an IL2 mutein) on a first Fc monomer with a "knob" modification and a second polypeptide on the second Fc monomer possessing a "hole" modification to facilitate the expression of heterodimeric polypeptide conjugates.

The Fc region can be "lytic" or "non-lytic," but is typically non-lytic. A non-lytic Fc region typically lacks a high affinity Fc receptor binding site and a C1q binding site. The high affinity Fc receptor binding site of murine IgG Fc includes the Leu residue at position 235 of IgG Fc. Thus, the Fc receptor binding site can be inhibited by mutating or deleting Leu 235. For example, substitution of Glu for Leu 235 inhibits the ability of the Fc region to bind the high affinity Fc receptor. The murine C1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C1q binding site. The high affinity Fc receptor binding site includes the Leu residue at position 235 of IgG Fc, and the C1q binding site includes the Glu 318, Lys 320, and Lys 322 residues of IgG 1. Lytic IgG Fc has wild type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., The Immunologist 2:119-124, 1994; and Brekke et al., The Immunologist 2:125, 1994).

In certain embodiments, the amino- or carboxyl-terminus of an IL2 mutein of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

In some embodiments, the Fc domain monomer comprises at least one mutation relative to a wild-type human IgG1, IgG2, or IgG4 Fc region as described in United States Patent No. U.S. Pat. No. 10,259,859B2, the entire teaching of which is herein incorporated by reference. As disclosed therein, the Fc domain monomer comprises:

(a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I:

or (b) (i) a N297A mutation relative to a human IgG1 Fc region;

(ii) a L234A, L235A, and G237A mutation relative to a human IgG1 Fc region;

(iii) a L234A, L235A, G237A, and N297A mutation relative to a human IgG1 Fc region;

(iv) a N297A mutation relative to a human IgG2 Fc region;

(v) a A330S and P331S mutation relative to a human IgG2 Fc region;

(vi) a A330S, P331S, and N297A mutation relative to a human IgG2 Fc region;

(vii) a S228P, E233P, F234V, L235A, and delG236 mutation relative to a human IgG4 Fc region: or (viii) a S228P, E233P, F234V, L235A, delG236, and N297A mutation relative to a human IgG4 Fc region.

In some embodiments, the Fc domain monomer comprises:

(a) one of the following amino acid substitutions relative to wild type human IgG1: T366W, T366S, L368A, Y407V, T366Y, T394W, F405W, Y349T, Y349E, Y349V, L35 IT, L351H, L351N, L351K, P353S, S354D, D356K, D356R, D356S, E357K, E357R, E357Q, S364A, T366E, L368T, L368Y, L368E, K370E, K370D, K370Q. K392E, K392D, T394N, P395N, P396T, V397T, V397Q, L398T, D399K, D399R, D399N, F405T, F405H, F405R, Y407T, Y407H, Y407I, K409E, K409D, K409T, or K409I;

and (b) the Fc domain monomer further comprises (i) a N297A mutation relative to a human IgG1 Fc region;

(ii) a L234A, L235A, and G237A mutation relative to a human IgG1 Fc region:

(iii) a L234A, L235A, G237A, and N297A mutation relative to a human IgG1 Fc region;

(iv) a N297A mutation relative to a human IgG2 Fc region:

(v) a A330S and P331S mutation relative to a human IgG2 Fc region;

(vi) a A330S, P331S, and N297A mutation relative to a human IgG2 Fc region;

(vii) a S228P, E233P, F234V, L235A, and delG236 mutation relative to a human IgG4 Fc region: or (viii) a S228P, E233P, F234V, L235A, delG236, and N297A mutation relative to a human IgG4 Fc region.

In some embodiments, the polypeptide exhibits a reduction of phagocytosis in a phagocytosis assay compared to a polypeptide with a wild-type human IgG Fc region. In some embodiments, the Fc domain monomer is linked to a second polypeptide comprising a second Fc domain monomer to form an Fc domain dimer.

Chimeric Polypeptides Fusion Proteins

In some embodiments, embodiment, the IL2 mutein may comprise a functional domain of a chimeric polypeptide. IL2 mutein fusion proteins of the present disclosure may be readily produced by recombinant DNA methodology by techniques known in the art by constructing a recombinant vector comprising a nucleic acid sequence comprising a nucleic acid sequence encoding the IL2 mutein in frame with a nucleic acid sequence encoding the fusion partner either at the N-terminus or C-terminus of the IL2 mutein, the sequence optionally further comprising a nucleic acid sequence in frame encoding a linker or spacer polypeptide.

In some embodiments, the IL2 mutein is conjugated (either chemically or as a fusion protein in the case of polypeptide agents such as antibodies or vaccines) to an additional chemical or biological agent including therapeutic compounds such as anti-inflammatory, antimicrobial, or antiviral compounds or other agents useful in the treatment of autoimmune disease including biologics (e.g. entaracept), monoclonal antibodies. Anti-microbial agents include aminoglycosides including gentamicin, antiviral compounds such as rifampicin, 3'-azido-3'-deoxy thymidine (AZT) and acylovir, antifungal agents such as azoles including fluconazole, plyre macrolides such as amphotericin B, and candicidin, anti-parasitic compounds such as antimonials, and the like. The IL2 mutein may be conjugated to additional cytokines as CSF, GSF, GMCSF, TNF, erythropoietin, immunomodulators or cytokines such as the interferons or interleukins, a neuropeptide, reproductive hormones such as HGH, FSH, or LH, thyroid hormone, neurotransmitters such as acetylcholine, hormone receptors such as the estrogen receptor. Also included are non-steroidal anti-inflammatoires such as indomethacin, salicylic acid acetate, ibuprofen, sulindac, piroxicam, and naproxen, and anesthetics or analgesics. Also included are radioisotopes such as those useful for imaging as well as for therapy.

The IL-2 mutein also may be conjugated to corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus), IMDH inhibitors (including but not limited to azathioprine, leflunomide and mycophenolate). The IL-2 mutein also may be conjugated to biologics such as abatcept (Orencia®) or etanercept (Enbrel®). The IL-2 mutein also may be conjugated to and therapeutic antibodies such as anti-CD25 antibodies (e.g. daclizumab and basiliximab), anti-VLA-4 antibodies (e.g. natalizumab), anti-CD52 antibodies (e.g. alemtuzumab), anti-CD20 antibodies (e.g. rituximab, ocrelizumab), anti-TNF antibodies (e.g. infliximab, and adalimumab), anti-IL-6R antibodies (e.g. tocilizumab), anti-TNFα antibodies (e.g. adalimumab (Humira®), golimumab, and infliximab), anti-integrin-α4β7 antibodies (e.g. vedolizumab), anti-IL-17a antibodies (e.g. brodalumab or secukinumab), anti-IL-4Rα antibodies (e.g. dupilumab), anti-RANKL (e.g.), antibodies IL-6R antibodies, anti-IL-1ß antibodies (e.g. canakinumab), anti-CD11a antibodies (e.g. efalizumab), anti-CD3 antibodies (e.g. muramonab), anti- IL5 antibodies (e.g. mepolizumab, reslizumab), anti-BLyS antibodies (e.g. belimumab); and anti-IL-12/IL-23 antibodies (e.g ustekinumab).

The IL-2 mutein also may be conjugated to such as HSV vaccines, *Bordetella pertussis, Escherichia coli* vaccines, pneumococcal vaccines including multivalent pneumococcal vaccines such as Prevnar® 13, diptheria toxoid, tetanus toxoid and pertussis vaccines (including combination vaccines such as Pediatrix®) and Pentacel®), varicella vaccines, *Haemophilus influenzae* type B (HIB) vaccines, human papilloma virus (HPV) vaccines such as Garasil®, polio vaccines, Leptospirosis vaccines, combination respiratory vaccine, *Moraxella* vaccines, and attenuated live or killed virus products such as bovine respiratory disease vaccine (RSV), human influenza vaccines such as Fluzone® and Quadravlent Fluzone®), feline leukemia vaccine, transmissible gastroenteritis vaccine, and rabies vaccine.

The IL2 muteins of the present disclosure may be chemically conjugated to such additional agents using well known chemical conjugation methods. Bi-functional cross-linking reagents such as homofunctional and heterofunctional cross-linking reagents well known in the art can be used for this purpose. The type of cross-linking reagent to use depends on the nature of the molecule to be coupled to IL-2 mutein and can readily be identified by those skilled in the art. Alternatively, or in addition, the IL2 mutein and/or the molecule to which it is intended to be conjugated may be chemically derivatized such that the two can be conjugated in a separate reaction as is also well known in the art.

Flag Tags

In other embodiments, the IL2 mutein can be modified to include an additional polypeptide sequence that functions as an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL2 mutein polypeptide further comprises a C-terminal c-myc epitope tag.

His Tags

In some embodiment, the IL2 muteins (including fusion proteins of such IL2 muteins) of the present invention are expressed as a fusion protein with one or more transition metal chelating polypeptide sequences. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present invention are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present invention are peptides comprising 3-6 contiguous histidine residues (SEQ ID NO: 98) such as a six-histidine peptide (His) 6 (SEQ ID NO: 99) and are frequently referred to in the art as "His-tags."

Targeting Moieties:

In some embodiments, the IL2 mutein is provided as a fusion protein with a polypeptide sequence ("targeting domain") to facilitate selective binding to particular cell type or tissue expressing a cell surface molecule that specifically binds to such targeting domain. In some embodiments, the targeting domain is an antibody (in particular a single domain antibody, scFv or VHH) or ligand that specifically binds to the surface protein of a protein selected from the group consisting of BLyS, CD11a, CD20, CD25, CD3, CD52,IgEIL-12/IL-23, IL-17a, IL-1ß, IL-4Rα, IL-5, IL-6R, integrin-α4β7, RANKL, TNFα, VEGF-A, VLA-4.

Preparation of IL2 Muteins

The IL2 muteins may be produced by conventional methodology for the construction of polypeptides including recombinant or solid phase syntheses.

Chemical Synthesis:

In addition to generating mutant polypeptides via expression of nucleic acid molecules that have been altered by recombinant molecular biological techniques, subject IL-2 muteins can be chemically synthesized. Chemically synthesized polypeptides are routinely generated by those of skill in the art. Chemical synthesis includes direct synthesis of a peptide by chemical means of the protein sequence encoding for an IL-2 mutein exhibiting the properties described. This method can incorporate both natural and unnatural amino acids at positions that affect the interactions of IL2 with CD25, CD122 and, CD132.

In some embodiments, the IL2 muteins of the present disclosure may be prepared by chemical synthesis. The chemical synthesis of the IL2 muteins of may proceed via liquid-phase or solid-phase. Solid-phase peptide synthesis (SPPS) allows the incorporation of unnatural amino acids and/or peptide/protein backbone modification. Various forms of SPPS are available for synthesizing IL2 muteins of the present disclosure are known in the art (e.g., Ganesan A. (2006) Mini Rev. Med. Chem. 6:3-10; and Camarero et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers: hydroxy methylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production:

Alternatively, the IL2 muteins of the present disclosure are produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation. The process for the recombinant production of IL2 polypeptides is known in the art and described in Fernandes and Taforo, U.S. Pat. No. 4,604,377 issued Aug. 5, 1986 and IL2 muteins in Mark, et al U.S. Pat. No. 4,512,584 issued May 21, 1985, Gillis, U.S. Pat. No. 4,401, 756 issued Aug. 30, 1983 the entire teachings of which are herein incorporated by reference.

Construction of Nucleic Acid Sequences Encoding the IL2 Mutein

In some embodiments, the IL2 mutein is produced by recombinant methods using a nucleic acid sequence encoding the IL2 mutein (or fusion protein comprising the IL2 mutein). The nucleic acid sequence encoding the desired IL-2 mutein can alternatively be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the IL2 mutein (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the IL2 mutein may be obtained from various commercial sources that provide custom made nucleic acid sequences. Amino acid sequence variants of the IL2 polypeptides to the produce the IL2 muteins of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion is made to arrive at the final construct, provided that the final construct possesses the desired biological activity as defined herein.

Methods for constructing a DNA sequence encoding the IL-2 muteins and expressing those sequences in a suitably transformed host include, but are not limited to, using a PCR-assisted mutagenesis technique. Mutations that consist of deletions or additions of amino acid residues to an IL-2 polypeptide can also be made with standard recombinant techniques. In the event of a deletion or addition, the nucleic acid molecule encoding IL-2 is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

An IL2 mutein of the present disclosure may be produced recombinantly not only directly, but also as a fusion polypeptide with a heterologous polypeptide, e.g. a signal sequence or other polypeptide having a specific cleavage site at the N-terminus or C-terminus of the mature IL2 mutein. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IL2 mutein (i.e. the human IL2 signal sequence). The inclusion of a signal sequence depends on whether it is desired to secrete the IL-2 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL-2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as *Saccharomyces cerevisiae*, the alpha mating factor secretion signal sequence may be employed to achieve extracellular secretion of the IL2 mutein into the culture medium as described in Singh, U.S. Pat. No. 7,198, 919 B1 issued Apr. 3, 2007.

In the event the IL2 mutein to be expressed is to be expressed as a chimera (e.g., a fusion protein comprising an IL2 mutein and a heterologous polypeptide sequence), the chimeric protein can be encoded by a hybrid nucleic acid molecule comprising a first sequence that encodes all or part of the IL-2 mutein and a second sequence that encodes all or part of the heterologous polypeptide. For example, subject IL-2 muteins described herein may be fused to a hexa-histidine tag (SEQ ID NO: 99) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the IL2 mutein. For example, the N-terminus may be linked to a targeting domain and the C-terminus linked to a hexa-histidine tag (SEQ ID NO: 99) purification handle.

The complete amino acid sequence of the polypeptide (or fusion/chimera) to be expressed can be used to construct a back-translated gene. A DNA oligomer containing a nucleotide sequence coding for IL-2 mutein can be synthesized. For example, several small oligonucleotides coding for portions of the desired polypeptide can be synthesized and then ligated. The individual oligonucleotides typically contain 5' or 3' overhangs for complementary assembly.

Codon Optimization:

In some embodiments, the nucleic acid sequence encoding the IL2 mutein may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g. Hawash, et al (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Construction of Expression Vectors:

Once assembled (by synthesis, site-directed mutagenesis or another method), the nucleic acid sequence encoding an IL-2 mutein will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors.

To facilitate efficient expression of the recombinant polypeptide, the nucleic acid sequence encoding the polypeptide sequence to be expressed is operably linked to transcriptional and translational regulatory control sequences that are functional in the chosen expression host.

Selectable Marker:

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Regulatory Control Sequences:

Expression vectors for IL2 muteins of the present disclosure contain a regulatory sequence that is recognized by the host organism and is operably linked to nucleic acid sequence encoding the IL2 mutein. The terms “regulatory control sequence,” “regulatory sequence” or “expression control sequence” are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject IL-2 mutein, particularly as regards potential secondary structures.

Promoters:

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Enhancers:

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context.

Proper assembly of the expression vector can be confirmed by nucleotide sequencing, restriction mapping, and expression of a biologically active polypeptide in a suitable host.

Host Cells:

The present disclosure further provides prokaryotic or eukaryotic cells that contain and express a nucleic acid molecule that encodes a IL-2 mutein. A cell of the present disclosure is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this invention, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant IL-2 muteins or biologically active variants thereof can also be made in eukaryotes, such as yeast or human cells. Suitable eukaryotic host cells include insect cells (examples of Baculovirus vectors available for expression of proteins in cultured insect cells (e.g., Sf) cells) include the pAc series (Smith et al. (1983) Mol. Cell Biol. 3:2156-2165) and the pVL series (Lucklow and Summers (1989) Virology 170:31-39)): yeast cells (examples of vectors for expression in yeast S. cerenvisiae include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)): or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M [TK-], ATCC #CRL-2648), monkey kidney CVI line transformed by SV40 (COS-7, ATCC CRL 1651): human embryonic kidney line (HEK293 or HEK293 cells subcloned for growth in suspension culture: baby hamster kidney cells (BHK, ATCC CCL 10); Chinese hamster ovary cells/-DHFR (CHO): mouse sertoli cells (TM4); monkey kidney cells (CVI ATCC CCL 70): African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75): human liver cells (Hep G2, HB 8065): mouse mammary tumor (MMT 060562, ATCC CCL51): TRI cells: MRC 5 cells: FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40).

The IL-2 mutein can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, IL-2 muteins obtained will be glycosylated or unglycosylated depending on the host organism used to produce the mutein. If bacteria are chosen as the host then the IL-2 mutein produced will be unglycosylated. Eukaryotic cells, on the other hand, will glycosylate the IL-2 muteins, although perhaps not in the same way as native-IL-2 is glycosylated.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection:

The expression constructs of the can be introduced into host cells to thereby produce the IL-2 muteins disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture:

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins:

Recombinantly produced IL2 mutein polypeptides can be recovered from the culture medium as a secreted polypeptide if a secretion leader sequence is employed. Alternatively, the IL2 mutein polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification:

Various purification steps are known in the art and find use, e.g. affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g. gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The IL-2 mutein produced by the transformed host can be purified according to any suitable method. Various methods are known for purifying IL-2. See, e.g. Current Protocols in Protein Science, Vol 2. Eds: John E. Coligan, Ben M. Dunn, Hidde L. Ploehg, David W. Speicher, Paul T. Wingfield, Unit 6.5 (Copyright 1997, John Wiley and Sons, Inc. IL-2 muteins can be isolated from inclusion bodies generated in *E. coli*, or from conditioned medium from either mammalian or yeast cultures producing a given mutein using cation exchange, gel filtration, and or reverse phase liquid chromatography.

The substantially purified forms of the recombinant polypeptides can be purified from the expression system using routine biochemical procedures, and can be used, e.g., as therapeutic agents, as described herein.

The biological activity of the IL-2 muteins can be assayed by any suitable method known in the art and may be evaluated as substantially purified forms or as part of the cell lysate or cell medium when secretion leader sequences are employed for expression. Such activity assays include CTLL-2 proliferation, induction of phospho-STAT5 (pSTAT5) activity in T cells, PHA-blast proliferation and NK cell proliferation.

Formulations

For therapeutic applications, the mutein can be administered to a mammal. Administration may be intravenous, as a bolus or by continuous infusion over a period of time. Alternative routes of administration include intramuscular, intraperitoneal, intra-cerobrospinal, subcutaneous, intra-articular, intrasynovial, intrathecal, oral, topical, or inhalation routes. The IL2 muteins also are suitably administered by intratumoral, peritumoral, intralesional, intranodal or perilesional routes or to the lymph, to exert local as well as systemic therapeutic effects.

In some embodiments, subject IL-2 muteins (and/or nucleic acids can be incorporated into compositions, including pharmaceutical compositions. Such compositions typically include the polypeptide or nucleic acid molecule and a pharmaceutically acceptable carrier. A pharmaceutical composition is formulated to be compatible with its intended route of administration and is compatible with the therapeutic use for which the IL2 mutein is to be administered to the subject in need of treatment or prophyaxis.

Parenteral Formulations:

The mutant IL-2 polypeptides of the invention may be given orally, but it is more likely that they will be administered through a parenteral route. Examples of parenteral routes of administration include, for example, intravenous, intradermal, subcutaneous, transdermal (topical), transmucosal, and rectal administration. Parenteral formulations comprise solutions or suspensions used for parenteral application can include vehicles the carriers and buffers. Pharmaceutical formulations for parenteral administration include sterile aqueous solutions (where water soluble) or dispersions and sterile powders for the extemporaneous preparation of sterile injectable solutions or dispersion.

Carriers: Carriers include a sterile diluent such as water for injection, saline solution, fixed oils, polyethylene glycols, glycerine, propylene glycol or other synthetic solvents. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. For intravenous administration, suitable carriers include physiological saline, bacteriostatic water, Cremophor ELTM. (BASF, Parsippany, N.J.) or phosphate buffered saline (PBS).

Buffers: The term buffers includes buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5).

Dispersions: Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Preservatives: The pharmaceutical formulations for parenteral administration to a subject should be sterile and should be fluid to facilitate easy syringability. It should be stable under the conditions of manufacture and storage and are preserved against the contamination. Prevention of the action of microorganisms can be achieved by various antibacterial and antifungal agents, for example, agents such as benzyl alcohol or methyl parabens; antioxidants such as ascorbic acid or sodium bisulfite; chelating agents such as ethylenediaminetetraacetic acid, parabens, chlorobutanol, phenol, ascorbic acid, thimerosal, and the like. Sterile solutions can be prepared by incorporating the active compound in the required amount in an appropriate solvent with one or a combination of ingredients enumerated above, as required, followed by filtered sterilization.

Tonicity Agents: In many cases, it will be preferable to include isotonic agents, for example, sugars, polyalcohols such as mannitol, sorbitol, sodium chloride in the composition.

Oral Compositions: Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin: an excipient such as starch or lactose, a disintegrating agent such as alginic acid, Primogel™, or corn starch; a lubricant such as magnesium stearate or Sterotes™: a glidant such as colloidal silicon dioxide: a sweetening agent such as sucrose or saccharin: or a flavoring agent such as peppermint, methyl salicylate, or orange flavoring.

Inhalation Formulations: In the event of administration by inhalation, subject IL-2 muteins, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Mucosal and Transdermal: Systemic administration of the subject IL-2 muteins or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories suppositories (e.g., with conventional suppository bases such as cocoa butter and other glycerides) or retention enemas for rectal delivery. For transdermal administration, the active compounds are formulated into ointments, salves, gels, or creams as generally known in the art and may incorporate permeation enhancers such as ethanol or lanolin.

Extended Release and Depot Formulations: In some embodiments, the IL2 mutein is administered in a formulation to provide extended release of the IL2 mutein agent. Examples of extended release formulations of the injectable compositions can be brought about by including in the composition an agent which delays absorption, for example, aluminum monostearate and gelatin. In one embodiment, the subject IL-2 muteins or nucleic acids are prepared with carriers that will protect the mutant IL-2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Administration of Nucleic Acids Encoding the IL2 Mutein (Gene Therapy): In some embodiments, compounds (subject IL-2 muteins or nucleic acids) can also be administered by transfection or infection using methods known in the art, including but not limited to the methods described in McCaffrey et al. (Nature 418:6893, 2002), Xia et al. (Nature Biotechnol. 20:1006-1010, 2002), or Putnam (Am. J. Health Syst. Pharm. 53:151-160, 1996, erratum at Am. J. Health Syst. Pharm. 53:325, 1996). In some embodiments, the IL2 mutein is administered to a subject by the administration of a pharmaceutically acceptable formulation of recombinant expression vector. In one embodiment, the recombinant expression vector is a viral vector. In some embodiments, the recombinant vector is a recombinant viral vector. In some embodiments the recombinant viral vector is a recombinant adenoassociated virus (rAAV) or recombinant adenovirus (rAd), in particular a replication deficient adenovirus derived from human adenovirus serotypes 3 and/or 5. In some embodiments, the replication deficient adenovirus has one or more modifications to the E1 region which interfere with the ability of the virus to initiate the cell cycle and/or apoptotic pathways in a human cell. The replication deficient adenoviral vector may optionally comprise deletions in the E3 domain. In some embodiments the adenovirus is a replication competent adenovirus. In some embodiments the adenovirus is a replication competent recombinant virus engineered to selectively replicate in lymphocytes.

In one embodiment, the IL2 mutein formulation is provided in accordance with the teaching of Fernandes and Taforo, U.S. Pat. No. 4,604,377 issued Aug. 5, 1986 the teaching of which is herein incorporated by reference. And Yasui, et al Unied States U.S. Pat. No. 4,645,830.

The parenteral preparation can be enclosed in ampoules, disposable syringes or multiple dose vials made of glass or plastic. In one embodiment, the formulation is provided in a prefilled syringe for parenteral administration.

Methods of Use

The present disclosure further provides methods of treating a subject suffering from a disease disorder or condition by the administration of a therapeutically effective amount of an IL2 mutein (or nucleic acid encoding an IL2 mutein including recombinant viruses encoding IL2 muteins) of the present disclosure. In the treatment of such diseases, the IL-2 muteins of the present disclosure may be incorporate modifications to provide advantageous properties, such as reduced vascular leak syndrome. Disorders amenable to treatment with IL-2 muteins (including pharmaceutically acceptable formulations comprising IL2 muteins and/or the nucleic acid molecules that encode them including recombinant viruses encoding such IL2 muteins) of the present disclosure include inflammatory or autoimmune diseases including but not limited to, viral infections (e.g., AIDS, influenza, chronic HCV, chronic viral hepatitis B, C or D), heliobacter *pylori* infection, HTLV, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes including Type 1 or type 2 diabetes, inflammation, autoimmune disease, atopic diseases, paraneoplastic autoimmune diseases, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity Enthesopathy Arthropathy Syndrome), juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome (Seronegativity, Enthesopathy, Arthropathy Syndrome).

Other examples of proliferative and/or differentiative disorders amenable to treatment with IL-2 muteins (including pharmaceutically acceptable formulations comprising IL2 muteins and/or the nucleic acid molecules that encode them including recombinant viruses encoding such IL2 muteins) of the present disclosure include, but are not limited to, skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum *spinosum*, stratum *granulosum*, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, *pityriasis rubra* pilaris, *pityriasis* rosacea, parapsoriasis, *pityriasis* lichenoiders, lichen planus, lichen *nitidus*, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma *acuminatum*, and human papilloma viral (HPV) infections such as venereal warts; leukoplakia: lichen planus; and keratitis.

The skin disorder can be dermatitis, e.g., atopic dermatitis or allergic dermatitis, or psoriasis. The compositions of the present disclosure (including pharmaceutically acceptable formulations comprising IL2 muteins and/or the nucleic acid molecules that encode them including recombinant viruses encoding such IL2 muteins) can also be administered to a patient who is suffering from (or may suffer from) psoriasis or psoriatic disorders. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, plaque psoriasis, moderate to severe plaque psoriasis, psoriasis vulgaris, eruptive psoriasis, psoriatic erythroderma, generalized pustular psoriasis, annular pustular psoriasis, or localized pustular psoriasis.

In certain embodiments, the subject IL-2 mutein that function as IL-2 antagonists described herein are useful for the treatment of one or more conditions wherein suppression of one or more IL-2 and/or IL-15 dependent functions is useful. In certain embodiments, the IL-2 muteins described herein is used for the treatment of one or more diseases or conditions wherein suppression of CD122/CD132 heterodimerization and downstream signaling is useful (e.g., GVDH or leukemia). In one embodiment, the method of treatment is for the treatment of graft versus host disease (GVHD). In some embodiments, the treatment includes the step of administering to a subject having GVHD a therapeutically effective amount of an IL-2 mutein (including pharmaceutically acceptable formulations comprising IL2 muteins and/or the nucleic acid molecules that encode them including recombinant viruses encoding such IL2 muteins).

Combination of IL2 Muteins with Additional Therapeutic Agents for Autoimmune Disease:

The present disclosure provides the for the use of the IL2 muteins of the present disclosure in combination with one or more additional active agents ("supplementary agents") in the treatment of autoimmune disease. As used herein, the term "supplementary agents" includes agents that can be administered or introduced separately, for example, formulated separately for separate administration (e.g., as may be provided in a kit) and/or therapies that can be administered or introduced in combination with the IL2 muteins.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g. IL2 mutein) is considered to be administered in combination with a second agent (e.g. a therapeutic autoimmune antibody such as Humira®) if the biological effect resulting from the administration of the first agent persists in the subject at the time of administration of the second agent such that the therapeutic effects of the first agent and second agent overlap. For example, the therapeutic antibodies are sometimes administered by IV infusion every two weeks (e.g. adalimumab in the treatment of Crohn's disease) while the IL2 muteins of the present disclosure may be administered more frequently, e.g. daily, BID, or weekly. However, the administration of the first agent (e.g. entaercept) provides a therapeutic effect over an extended time and the administration of the second agent (e.g. an IL2 mutein) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL2 mutein and the supplementary agent(s) are administered or applied sequentially, e.g., where one agent is administered prior to one or more other agents. In other embodiments, the IL2 mutein and the supplementary agent (s) are administered simultaneously, e.g., where two or more agents are administered at or about the same time: the two or more agents may be present in two or more separate formulations or combined into a single formulation (i.e., a co-formulation). Regardless of whether the agents are administered sequentially or simultaneously, they are considered to be administered in combination for purposes of the present disclosure.

In some embodiments, the supplementary agent is one or more agents selected from the group consisting of corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus), IMDH inhibitors (including but not limited to azathioprine, leflunomide and mycophenolate), biologics such as abatcept (Orencia®) or etanercept (Enbrel®), and therapeutic antibodies. Examples of therapeutic antibodies that may be administered as supplementary agents in combination with the IL2 muteins of the present disclosure in the treatment of autoimmune disease include but are not limited to anti-CD25 antibodies (e.g. daclizumab and basiliximab), anti-VLA-4 antibodies (e.g. natalizumab), anti-CD52 antibodies (e.g. alemtuzumab), anti-CD20 antibodies (e.g. rituximab, ocrelizumab), anti-TNF antibodies (e.g. infliximab, and adalimumab), anti-IL-6R antibodies (e.g. tocilizumab), anti-TNFα antibodies (e.g. adalimumab (Humira®), golimumab, and infliximab), anti-integrin-α4β7 antibodies (e.g. vedolizumab), anti-IL-17a antibodies (e.g. brodalumab or secukinumab), anti-IL-4Rα antibodies (e.g. dupilumab), anti-RANKL antibodies, IL-6R antibodies, anti-IL-1ß antibodies (e.g. canakinumab), anti-CD11a antibodies (e.g. efalizumab), anti-CD3 antibodies (e.g. muramonab), anti-IL5 antibodies (e.g. mepolizumab, reslizumab), anti-BLyS antibodies (e.g. belimumab); and anti-IL-12/IL-23 antibodies (e.g ustekinumab).

Many therapeutic antibodies have been approved for clinical use against autoimmune disease. Examples of antibodies approved by the United States Food and Drug Administration (FDA) for use in the treatment of autoimmune diseases in a subject suffering therefrom that may be administered as supplementary agents in combination with the IL2 muteins of the present disclosure (and optionally additional supplementary agents) for the treatment of the indicated autoimmune disease are provided in Table 4.

TABLE 4

| Name | Target | Indication |
|---|---|---|
| belimumab | BLyS | Systemic lupus erythematosus |
| efalizumab | CD11a | Psoriasis |
| ocrelizumab | CD20 | Multiple sclerosis |
| rituximab | CD20 | Multiple sclerosis |
| basiliximab | CD25 | Transplantation rejection |
| daclizumab | CD25 | Transplantation rejection |
| muromonab | CD3 | Transplantation rejection |
| alemtuzumab | CD52 | Multiple sclerosis |
| omalizumab | IgE | Asthma |
| ustekinumab | IL-12/IL-23 | Plaque psoriasis |
| brodalumab | IL-17a | Psoriasis, psoriatic arthritis, ankylosing spondylitis |
| secukinumab | IL-17a | Psoriasis, psoriatic arthritis, ankylosing spondylitis |
| ixekizumab | IL-17a | Psoriasis, psoriatic arthritis, anky losing spondylitis |
| canakinumab | IL-1β | Cryopyrin-associated periodic syndrome, tumor necrosis factor receptor associated periodic syndrome, hyperimmunoglobulin D syndrome, mevalonate kinase deficiency, familial Mediterranean fever, rheumatoid arthritis |
| dupilumab | IL-4Rα | Asthma, dermatitis |
| mepolizumab | IL-5 | Asthma |
| reslizumab | IL-5 | Asthma |
| tocilizumab | IL-6R | Rheumatoid arthritis |
| vedolizumab | Integrin-α4β7 | Ulcerative colitis, Crohn's disease |
| denosumab | RANKL | Osteoporosis |
| certolizumab | TNFa | Chron's disease, rheumatoid arthritis |
| golimumab | TNFa | Rheumatoid arthritis, psoriatic arthritis, anky losing spondylitis |
| adalimumab | TNFα | Rheumatoid arthritis, juvenile idiopathic arthritis, psoriatic arthritis, ankylosing spondylitis, Crohn's disease, plaque psoriasis |
| infliximab | TNFα | Crohn's disease, ulcerative colitis, rheumatoid arthritis, ankylosing spondylitis, psoriatic arthritis, plaque psoriasis |
| ranibizumab | VEGF-A | Neovascular age-related macular degeneration, macular edema |
| natalizumab | VLA-4 | Multiple sclerosis, relapsing rultiple sclerosis, Crohn's disease |

The foregoing antibodies useful as supplementary agents in the practice of the methods of the present disclosure may be administered alone or in the form of any antibody drug conjugate (ADC) comprising the antibody, linker, and one or more drugs (e.g. 1, 2, 3, 4, 5, 6, 7, or 8 drugs) or in modified form (e.g. PEGylated).

In some embodiments the supplementary agent is a vaccine. The IL2 muteins of the present invention may be administered to a subject in combination with vaccines as an adjuvant to enhance the immune response to the vaccine in accordance with the teaching of Doyle, et al Unite States U.S. Pat. No. 5,800,819 issued Sep. 1, 1998. Examples of vaccines that may be combined with the IL2 muteins of the present invention include are HSV vaccines, *Bordetella pertussis, Escherichia coli* vaccines, pneumococcal vaccines including multivalent pneumococcal vaccines such as Prevnar® 13, diptheria, tetanus and pertussis vaccines (including combination vaccines such as Pediatrix®) and Pentacel®), varicella vaccines, *Haemophilus influenzae* type B vaccines, human papilloma virus vaccines such as Garasil®, polio vaccines, Leptospirosis vaccines, combination respiratory vaccine, *Moraxella* vaccines, and attenuated live or killed virus products such as bovine respiratory disease vaccine (RSV), multivalent human influenza vaccines such as Fluzone® and Quadravlent Fluzone®), feline leukemia vaccine, transmissible gastroenteritis vaccine, and rabies vaccine.

Dosage

Dosage, toxicity and therapeutic efficacy of such subject IL-2 muteins or nucleic acids compounds can be determined by standard pharmaceutical procedures in cell cultures or experimental animals. The data obtained from the cell culture assays and animal studies can be used in formulating a range of dosage for use in humans. The dosage of such compounds lies preferably within a range of circulating concentrations that include the ED50 with minimal acceptable toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a subject IL-2 mutein (i.e., an effective dosage) depends on the polypeptide selected. For instance, single dose amounts in the range of approximately 0.001 to 0.1 mg/kg of patient body weight can be administered: in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization 1st International Standard for Interleukin-2 (human)).

In some embodiments, the pharmaceutically acceptable forms of the IL2 muteins of the present disclosure are administered to a subject in accordance with a "low-dose" treatment protocol as described in Klatzman, et al. U.S. Pat. Nos. 9,669,071 and 10,293,028B2 the entire teachings of which are herein incorporated by reference. Additional low dose protocols are described in Smith, K. A. (1993) Blood 81(6): 1414-1423, He, et al (2016) Nature Medicine 22 (9): 991-993

In accordance with another aspect of the present disclosure, there is provided a method for stimulating the immune system of an animal by administering the IL-2 muteins of the present disclosure. The method is useful to treat disease states where the host immune response is deficient. In treating a subject, a therapeutically effective dose of compound (i.e., active ingredient) is administered. A therapeutically effective dose refers to that amount of the active ingredient that produces amelioration of symptoms or a prolongation of survival of a subject. An effective dose will vary with the characteristics of the IL-2 mutein to be administered, the physical characteristics of the subject to be treated, the nature of the disease or condition, and the like. A single administration can range from about 50,000 IU/kg to about 1,000,000 IU/kg or more, more typically about 600,000 IU/kg. This may be repeated several times a day (e.g., 2-3 times per day) for several days (e.g., about 3-5 consecutive day's) and then may be repeated one or more times following a period of rest (e.g., about 7-14 days). Thus, an effective dose may comprise only a single administration or many administrations over a period of time (e.g., about 20-30 individual administrations of about 600,000 IU/kg each given over about a 10-20 day period).

The compositions can be administered one from one or more times per day to one or more times per week: including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the subject IL-2 muteins can include a single treatment or, can include a series of treatments. In one embodiment, the compositions are administered every 8 hours for five days, followed by a rest period of 2 to 14 days, e.g., 9 days, followed by an additional five days of administration every 8 hours. In another embodiment, the compositions are administered every other day for a period of at least 6 days, optionally at least 10 days, optionally at least 14 days, optionally at least 30 days, optionally at least 60 days. The skilled artisan will recognize that the treatment may be extended for the treatment of chronic conditions and the prevent the reoccurrence of symptoms of chronic diseases such as autoimmune diseases (e.g. psoriasis, IBD, etc)

The pharmaceutical compositions can be included in a container, pack, or dispenser together with instructions for administration.

While compounds that exhibit toxic side effects may be used, care should be taken to design a delivery system that targets such compounds to the site of affected tissue in order to minimize potential damage to uninfected cells and, thereby, reduce side effects. Toxicity and therapeutic efficacy of an IL-2 mutein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. IL-2 mutants that exhibit large therapeutic indices are preferred. The data obtained from these cell culture assays and animal studies can be used in formulating a range of dosages suitable for use in humans. The dosage of such mutants lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition.

The attending physician for patients treated with IL-2 muteins and optionally supplementary agents would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

IL-2 mutants of the invention may be administered to an individual alone as a pharmaceutical preparation appropriately formulated for the route of delivery and for the condition being treated. Suitable routes may include oral, rectal, transdermal, vaginal, transmucosal, or intestinal administration: parenteral delivery, including intramuscular, subcutaneous, intramedullary injections, as well as intrathecal, direct intraventricular, intravenous, intraperitoneal, intranasal, or intraocular injections, and the like. For transmucosal administration, penetrants appropriate to the barrier to be permeated are used in the formulation. Such penetrants are generally known in the art.

IL-2 mutants may be manufactured as a formulation with one or more pharmaceutically acceptable carriers or excipient(s) as is well known in the art. Techniques for formulation and administration may be found in "Remington's Pharmaceutical Sciences," (18th ed., Mack Publishing Co., Easton, Pa., 1990). Specific examples of IL-2 formulations are described in U.S. Pat. Nos. 4,604,377 and 4,766,106. The IL-2 mutant may be formulated as a liquid with carriers that may include a buffer and or salt such as phosphate buffered saline. Alternatively, the IL-2 mutant may be formulated as a solid with carriers or fillers such as lactose, binders such as starches, and/or lubricants such as talc or magnesium stearate and, optionally, stabilizers.

Kits

The present disclosure also contemplates kits comprising pharmaceutical compositions IL2 muteins and a pharmaceutical composition thereof. The kits are generally in the form of a physical structure housing various components, as described below, and can be utilized, for example, in practicing the methods described above. A kit may comprise an IL2 mutein in the form of a pharmaceutical composition suitable for administration to a subject that is ready for use or in a form or requiring preparation for example, thawing, reconstitution or dilution prior to administration. When the IL2 mutein is in a form that needs to be reconstituted by a user, the kit may also comprise a sterile container providing a reconstitution medium comprising buffers, pharmaceutically acceptable excipients, and the like.

A kit of the present disclosure may further comprise one or more supplementary agents in addition to the other components.

A kit of the present disclosure can be designed for conditions necessary to properly maintain the components housed therein (e.g., refrigeration or freezing).

A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL2 mutein or kit comprising) in compliance with governmental regulations (e.g., HIPAA) are provided.

EXAMPLES

The following examples are provided to describe certain embodiments of the invention provided herein and are not to be construed to as limiting.

Example 1: Generation of the Human IL2 Expression Vector pcDNA3.1/Hygro(+)-huIL2

The human IL2 DNA open reading frame ("ORF") (Genbank NM_000586.3) was synthesized (Life Technologies GeneArt Service, Carlsbad, CA), and amplified via PCR using Platinum SuperFi II DNA polymerase kit (commercially available as catalog #12361050, ThermoFisher) in substantial accordance with the manufacturer's protocol, and using primers 5' TATAGTCAGCGCCACCCATGTACAGGATGCAACTCCTGTC 3' (SEQ ID NO: 100), which incorporates an NheI restriction site, and 5' TATAGGGCCCTATCAAGTCAGTGTTGAGATG 3' (SEQ ID NO: 101), which incorporates an ApaI restriction site. The PCR fragment was visualized on a 1% agarose gel (item #54803, Lonza, Rockland, ME), excised from the gel and purified using a QIAquick PCR Purification kit (commercially available as catalog #28106, Qiagen, Germany) according to the manufacturer's protocol.

The purified PCR fragment and mammalian expression vector pcDNA 3.1/Hygro(+) (commercially available as catalog #V87020, ThermoFisher, Carlsbad CA) were digested with NheI and ApaI (commercially available as catalog #R0111S and #R0114L, New England Biolabs, Ipswich, MA) restriction enzymes. The expression vector was further treated with a Quick Dephosphorylation kit (commercially available as catalog #M0508L, New England Biolabs) in substantial accordance with the manufacturer's protocol. The PCR fragment was ligated into pcDNA 3.1/Hygro(+) using the Rapid DNA Ligation Kit (commercially available as catalog #11635379001, Sigma Aldrich, St. Louis, MO) in substantial accordance with the manufacturer's protocol, transformed into One Shot TOP10 Chemically Competent *E. coli* (commercially available as catalog #C404006, Life Technologies, Carlsbad, CA), plated onto LB Agar plates containing 100 ug/ml carbenicillin (commercially available as catalog #L1010, Teknova, Hollister, CA), and grown overnight at 37C.

The following day individual bacterial colonies were picked and used to start a 3 ml bacterial culture in LB Broth (#10855-001, Life Technologies) with 100 ug/ml ampicillin (commercially available as catalog #A9626, Teknova). The cultures were grown overnight at 37C. The following day the *E. coli* were pelleted (6.000 rpm, 10 minutes, tabletop centrifuge #5424, commercially available as catalog Eppendorf, Hauppauge, NY), and the DNA expression vector isolated using QIAprep Spin Miniprep Kit (#27106, Qiagen). The plasmid DNA was sequence verified (MCLab, South San Francisco, CA).

Example 2. Generation of the Human IL2 REH Expression Vector pcDNA3.1/Hygro(+)-huIL2-REH An expression vector which introduced three mutations into the human IL2 ORF (L38R, Q42E and Q146H; all numbering based on the full length human IL2 ORF NM_000586.3 numbering. i.e. the hIL2 as expressed including the signal peptide not the 20 amino acid sequence of the mature hIL2 molecule) was assembled in substantial accordance with the teaching of Example 1 with the following exceptions: The initial template DNA used for PCR was synthesized with the L38R (L18R of the mature protein), Q42E (Q22E of the mature protein) and Q146H (Q126H of the mature protein) mutations.

Example 3. Generation of the Human IL2 REM Expression Vector pcDNA3.1/Hygro(+)-huIL2 REM An expression vector which introduced three mutations into the human IL2 ORF (L38R, Q42E and Q146M; all numbering based on the full length human IL2 ORF NM_000586.3 numbering) was assembled exactly as described for the human IL2 expression vector in pcDNA3.1/Hygro(+), with the following exceptions: The initial template DNA used for PCR was synthesized with the L38R, Q42E and Q146M mutations.

Example 4. Introduction of Mutations or Back-Mutations into pcDNA3.1/Hygro(+)-huIL2 and pcDNA3.1/Hygro(+)-huIL2 REH Expression Vectors All mutations or back-mutations (reverting a mutation in pcDNA3.1/hygro(+)-huIL2-REH back to match the wild type human IL2 ORF) were introduced into the pcDNA3.1/Hygro(+)-huIL2 or pcDNA3.1/Hygro(+)-huIL2-REH expression vectors using a Quik Change II Site Directed Mutagenesis Kit (#200524, Agilent Technologies, Santa Clara, CA) in substantial accordance with the manufacturer's protocol. Table 5 and Table 6 lists the mutations generated, the template into which the mutation was introduced, and the primer sets used to introduce the mutation. The transformation of the Quik Change PCR reactions into *E. coli*, as well as the isolation and sequence analysis of the plasmid DNA, was performed using the same protocol as in the generation of the pcDNA3.1/Hygro-huIL2 expression vector.

TABLE 5

Quik Change Mutagenesis

*Templates
IL2: pcDNA3.1/hygro(+)-huIL2
IL2 REH: pcDNA3.1/Hygro(+)-huIL2 REH
IL2 REK: pcDNA3.1/Hygro(+)-huIL2 REK
IL2 AEH: pcDNA3.1/Hygro(+)-huIL2 AEH
IL2 EEH: pcDNA3.1/Hygro(+)-huIL2 EEH
IL2 VEH: pcDNA3.1/Hygro(+)-huIL2 VEH
IL2 HEH: pcDNA3.1/Hygro(+)-huIL2 HEH
IL2 IEH: pcDNA3.1/Hygro(+)-huIL2 IEH
IL2 RTH: pcDNA3.1/Hygro(+)-huIL2 RTH

| hIL2 Wild Type human IL2 Residue | Full ORF # 38 / Mature Peptide # 18 L | 42 / 22 Q | 146 / 126 Q | Primer Set (5' → 3') | Template* |
|---|---|---|---|---|---|
| REE | R | E | E | GATGGATTACCTTTTGTGAGAGCATCATCTCAACA (SEQ ID NO: 7) TGTTGAGATGATGCTCTCACAAAAGGTAATCCATC (SEQ ID NO: 8) | IL2 REK |
| REM | R | E | M | GGATTACCTTTTGTATGAGCATCATCTCAAC (SEQ ID NO: 9) GTTGAGATGATGCTCATACAAAAGGTAATCC (SEQ ID NO: 10) | IL2 REK |
| REV | R | E | V | GGATTACCTTTTGTGTGAGCATCATCTCAACAC (SEQ ID NO: 11) GTGTTGAGATGATGCTCACACAAAAGGTAATCC (SEQ ID NO: 12) | IL2 REK |
| REL | R | E | L | GGATTACCTTTTGTCTGAGCATCATCTCAACAC (SEQ ID NO: 13) GTGTTGAGATGATGCTCAGACAAAAGGTAATCC (SEQ ID NO: 14) | IL2 REK |
| REF | R | E | F | GGATTACCTTTTGTTTCAGCATCATCTCAACAC (SEQ ID NO: 15) GTGTTGAGATGATGCTGAAACAAAAGGTAATCC (SEQ ID NO: 16) | IL2 REK |
| REN | R | E | N | GGATTACCTTTTGTAACAGCATCATCTCAACAC (SEQ ID NO: 17) GTGTTGAGATGATGCTGTTACAAAAGGTAATCC (SEQ ID NO: 18) | IL2 REK |
| RER | R | E | R | GGATTACCTTTTGTAGGAGCATCATCTCAACAC (SEQ ID NO: 19) GTGTTGAGATGATGCTCCTACAAAAGGTAATCC (SEQ ID NO: 20) | IL2 REK |

TABLE 5-continued

Quik Change Mutagenesis

*Templates
IL2: pcDNA3.1/hygro(+)-huIL2
IL2 REH: pcDNA3.1/Hygro(+)-huIL2 REH
IL2 REK: pcDNA3.1/Hygro(+)-huIL2 REK
IL2 AEH: pcDNA3.1/Hygro(+)-huIL2 AEH
IL2 EEH: pcDNA3.1/Hygro(+)-huIL2 EEH
IL2 VEH: pcDNA3.1/Hygro(+)-huIL2 VEH
IL2 HEH: pcDNA3.1/Hygro(+)-huIL2 HEH
IL2 IEH: pcDNA3.1/Hygro(+)-huIL2 IEH
IL2 RTH: pcDNA3.1/Hygro(+)-huIL2 RTH

| hIL2 Wild Type human IL2 Residue | Full ORF # 38 / Mature Peptide # 18 L | Full ORF # 42 / Mature Peptide # 22 Q | Full ORF # 146 / Mature Peptide # 126 Q | Primer Set (5' → 3') | Template* |
|---|---|---|---|---|---|
| REY | R | E | Y | GGATTACCTTTTGTTACAGCATCATCTCAACA C (SEQ ID NO: 21) GTGTTGAGATGATGCTGTAACAAAAGGTAATC C (SEQ ID NO: 22) | IL2 REK |
| AEK | A | E | K | GGATTACCTTTTGTAAGAGCATCATCTC (SEQ ID NO: 23) GAGATGATGCTCTTACAAAAGGTAATCC (SEQ ID NO: 24) | IL2 AEH |
| EEK | E | E | K | GGATTACCTTTTGTAAGAGCATCATCTC (SEQ ID NO: 25) GAGATGATGCTCTTACAAAAGGTAATCC (SEQ ID NO: 26) | IL2 EEH |
| VEK | V | E | K | GGATTACCTTTTGTAAGAGCATCATCTC (SEQ ID NO: 27) GAGATGATGCTCTTACAAAAGGTAATCC (SEQ ID NO: 28) | IL2 VEH |
| HEK | H | E | K | GGATTACCTTTTGTAAGAGCATCATCTC (SEQ ID NO: 29) GAGATGATGCTCTTACAAAAGGTAATCC (SEQ ID NO: 30) | IL2 HEH |
| IEK | I | E | K | GGATTACCTTTTGTAAGAGCATCATCTC (SEQ ID NO: 31) GAGATGATGCTCTTACAAAAGGTAATCC (SEQ ID NO: 32) | IL2 IEH |
| RTK | R | T | K | GGATTACCTTTTGTAAGAGCATCATCTC (SEQ ID NO: 33) GAGATGATGCTCTTACAAAAGGTAATCC (SEQ ID NO: 34) | IL2 RTH |

TABLE 6 hIL2 Ortholog Constructs

| Name | Primer Set (5' → 3') | Template |
|---|---|---|
| REE | GATGGATTACCTTTTGTGAGAGCATCATCTCA ACA (SEQ ID NO: 35) TGTTGAGATGATGCTCTCACAAAAGGTAATCC ATC (SEQ ID NO: 36) | pExSyn2.0 - hIL2 REK |
| REM | GGATTACCTTTTGTATGAGCATCATCTCAAC (SEQ ID NO: 37) GTTGAGATGATGCTCATACAAAAGGTAATCC (SEQ ID NO: 38) | pExSyn2.0 - hIL2 REK |
| REV | GGATTACCTTTTGTGTGAGCATCATCTCAACAC (SEQ ID NO: 39) GTGTTGAGATGATGCTCACACAAAAGGTAATC C (SEQ ID NO: 40) | pExSyn2.0 - hIL2 REK |
| REL | GGATTACCTTTTGTCTGAGCATCATCTCAACAC (SEQ ID NO: 41) GTGTTGAGATGATGCTCAGACAAAAGGTAATC C (SEQ ID NO: 42) | pExSyn2.0 - hIL2 REK |

TABLE 6-continued hIL2 Ortholog Constructs

| Name | Primer Set (5' → 3') | Template |
|---|---|---|
| REF | GGATTACCTTTTGTTTCAGCATCATCTCAACAC (SEQ ID NO: 43) GTGTTGAGATGATGCTGAAACAAAAGGTAATCC (SEQ ID NO: 44) | pExSyn2.0 - hIL2 REK |
| REN | GGATTACCTTTTGTAACAGCATCATCTCAACAC (SEQ ID NO: 45) GTGTTGAGATGATGCTGTTACAAAAGGTAATCC (SEQ ID NO: 46) | pExSyn2.0 - hIL2 REK |
| RER | GGATTACCTTTTGTAGGAGCATCATCTCAACAC (SEQ ID NO: 47) GTGTTGAGATGATGCTCCTACAAAAGGTAATCC (SEQ ID NO: 48) | pExSyn2.0 - hIL2 REK |
| REY | GGATTACCTTTTGTTACAGCATCATCTCAACAC (SEQ ID NO: 49) GTGTTGAGATGATGCTGTAACAAAAGGTAATCC (SEQ ID NO: 50) | pExSyn2.0 - hIL2 REK |
| REK + N88R | GACTTAATCAGCCGTATCAACGTAATA (SEQ ID NO: 51) TATTACGTTGATACGGCTGATTAAGTC (SEQ ID NO: 52) | pExSyn2.0 - hIL2 REK |
| REK + N88D | GGACTTAATCAGCGATATCAACGTAAT (SEQ ID NO: 53) ATTACGTTGATATCGCTGATTAAGTCC (SEQ ID NO: 54) | pExSyn2.0 - hIL2 REK |
| REK + N88G | GGGACTTAATCAGCGGTATCAACGTAAT (SEQ ID NO: 55) ATTACGTTGATACCGCTGATTAAGTCCC (SEQ ID NO: 56) | pExSyn2.0 - hIL2 REK |
| REK + N88I | GGACTTAATCAGCATTATCAACGTAAT (SEQ ID NO: 57) ATTACGTTGATAATGCTGATTAAGTCC (SEQ ID NO: 58) | pExSyn2.0 - hIL2 REK |
| REK + D20I | GCATTTAAGGCTGATTTTAGAGATGATTTTG (SEQ ID NO: 59) CAAAATCATCTCTAAAATCAGCCTTAAATGC (SEQ ID NO: 60) | pExSyn2.0 - hIL2 REK |
| REK + D20H | GAGCATTTAAGGCTGCATTTAGAGATG (SEQ ID NO: 61) CATCTCTAAATGCAGCCTTAAATGCTC (SEQ ID NO: 62) | pExSyn2.0 - hIL2 REK |
| REK + D20T | GCATTTAAGGCTGACTTTAGAGATGATTTTG (SEQ ID NO: 63) CAAAATCATCTCTAAAGTCAGCCTTAAATGC (SEQ ID NO: 64) | pExSyn2.0 - hIL2 REK |
| REK + D20G | GCATTTAAGGCTGGGTTTAGAGATGA (SEQ ID NO: 65) TCATCTCTAAACCCAGCCTTAAATGC (SEQ ID NO: 66) | pExSyn2.0 - hIL2 REK |
| REK + D20A | GCATTTAAGGCTGGCTTTAGAGATGATTTTG (SEQ ID NO: 67) CAAAATCATCTCTAAAGCCAGCCTTAAATGC (SEQ ID NO: 68) | pExSyn2.0 - hIL2 REK |
| AEH + V91K | CAGCAATATCAACAAGATAGTTCTGGAAC (SEQ ID NO: 69) GTTCCAGAACTATCTTGTTGATATTGCTG (SEQ ID NO: 70) | pExSyn2.0 - hIL2 AEH |
| EEH + V91K | CAGCAATATCAACAAGATAGTTCTGGAAC (SEQ ID NO: 71) GTTCCAGAACTATCTTGTTGATATTGCTG (SEQ ID NO: 72) | pExSyn2.0 - hIL2 EEH |

TABLE 6-continued

| hIL2 Ortholog Constructs | | |
|---|---|---|
| Name | Primer Set (5' → 3') | Template |
| VEH + V91K | CAGCAATATCAACAAGATAGTTCTGGAAC (SEQ ID NO: 73) GTTCCAGAACTATCTTGTTGATATTGCTG (SEQ ID NO: 74) | pExSyn2.0 - hIL2 VEH |
| HEH + V91K | CAGCAATATCAACAAGATAGTTCTGGAAC (SEQ ID NO: 75) GTTCCAGAACTATCTTGTTGATATTGCTG (SEQ ID NO: 76) | pExSyn2.0 - hIL2 HEH |
| IEH + V91K | CAGCAATATCAACAAGATAGTTCTGGAAC (SEQ ID NO: 77) GTTCCAGAACTATCTTGTTGATATTGCTG (SEQ ID NO: 78) | pExSyn2.0 - hIL2 IEH |
| RTH + V91K | CAGCAATATCAACAAGATAGTTCTGGAAC (SEQ ID NO: 79) GTTCCAGAACTATCTTGTTGATATTGCTG (SEQ ID NO: 80) | pExSyn2.0 - hIL2 RTH |
| REE + V91K | CAGCAATATCAACAAGATAGTTCTGGAAC (SEQ ID NO: 81) GTTCCAGAACTATCTTGTTGATATTGCTG (SEQ ID NO: 82) | pExSyn2.0 - hIL2 REE |
| AEK | GGATTACCTTTTGTAAGAGCATCATCTC (SEQ ID NO: 83) GAGATGATGCTCTTACAAAAGGTAATCC (SEQ ID NO: 84) | pExSyn2.0 - hIL2 AEH |
| EEK | GGATTACCTTTTGTAAGAGCATCATCTC (SEQ ID NO: 85) GAGATGATGCTCTTACAAAAGGTAATCC (SEQ ID NO: 86) | pExSyn2.0 - hIL2 EEH |
| VEK | GGATTACCTTTTGTAAGAGCATCATCTC (SEQ ID NO: 87) GAGATGATGCTCTTACAAAAGGTAATCC (SEQ ID NO: 88) | pExSyn2.0 - hIL2 VEH |
| HEK | GGATTACCTTTTGTAAGAGCATCATCTC (SEQ ID NO: 89) GAGATGATGCTCTTACAAAAGGTAATCC (SEQ ID NO: 90) | pExSyn2.0 - hIL2 HEH |
| IEK | GGATTACCTTTTGTAAGAGCATCATCTC (SEQ ID NO: 91) GAGATGATGCTCTTACAAAAGGTAATCC (SEQ ID NO: 92) | pExSyn2.0 - hIL2 IEH |
| RTK | GGATTACCTTTTGTAAGAGCATCATCTC (SEQ ID NO: 93) GAGATGATGCTCTTACAAAAGGTAATCC (SEQ ID NO: 94) | pExSyn2.0 - hIL2 RTH |
| N88R | GACTTAATCAGCCGTATCAACGTAATA (SEQ ID NO: 95) TATTACGTTGATACGGCTGATTAAGTC (SEQ ID NO: 96) | pExSyn2.0 - hIL2 |

Example 5. Transient Transfections in HEK293 Cells

All expression vectors were transiently transfected into HEK293 cells (#CRL-1573, ATCC, Manassas, VA). ~1E6 HEK293 cells were plated into each well of a 6 well tissue culture plate in 2 ml of DMEM (#10569044, Life Technologies) supplemented with 10% Fetal Bovine serum (#SH30071.03, Fisher Scientific, Chicago, IL), and grown overnight at 37C and 5% $CO_2$. The next day the cells were transfected using Lipofectamine 3000 Reagent (#L3000150, Life Technologies) following the manufacturer's protocol, using 2.5 ug DNA, 5 ul P3000 reagent, and 7.5 ul Lipofectamine 3000 per transfection. The transfected cells were grown at 37C, 5% $CO_2$ for 48-72 hours and then the conditioned media was harvested.

Example 6. Analysis of Protein Expression

Protein expression was measured by ELISA using the Human IL2 V-PLEX ELISA kit (#K151QQD-4, Mesoscale Diagnostics, Baltimore, MD) following the manufacturer's protocol (transfected media was diluted 1:4 initially, then 1:2 serially). The plate was read on a Meso Quickplex SQ120 (Mesoscale Diagnostics) using the manufacture's preprogrammed setting for this ELISA kit. The human IL2 standard in the kit was used to compute an approximate expression level in the conditioned media samples.

Example 7 Determination of IL2 Activity (STAT5) on CD25− and CD25+ Cells

Following a 2-3 day incubation, samples of the supernatants from the 293T cells containing the soluble IL2 protein were prepared in accordance with Example 5 above and added to YT cells (CD25NEG) and YT cells which have been engineered to constitutively express CD25 (YTCD25POS) for a period of approximately 20 minutes. The level of phospho-STAT5 (pSTAT5) induction was measured by flow cytometry. The results of the fold induction of pSTAT5 level is show in FIG. 2 of the accompanying drawings. Selectivity of the IL2 proteins for CD25 status was calculated as the level of phospho-STAT5 elevation on CD25+ YT cells ($pSTAT5^{YTCD25}$) divided by the level of phospho-STAT5 in CD25 negative YT cells ($pSTAT5^{YT}$). The results of these experiments are provided in FIG. 2 of the attached drawings.

As can be seen from the data presented, the IL2 muteins of the present disclosure provide for selective induction of pSTAT5 on CD25 positive cells and retain significant IL2 activity.

Example 8. Evaluation of Activity of Orthologs in Human T Cell Clone 3F8

A panel of representative hIL-2 muteins was evaluated for activity in CD4 positive human T cell clone 3F8 cells. The CD4 positive T cell clone 3F8 was generated by activation of PBMC of a healthy donor with the EBV transformed B cell line JY in two successive rounds of Mixed Leukocyte Reactions followed by single cell cloning by limited dilution as described (Yssel and Spits (2002) Current Protocols in Immunology 7.19.1-7.19.12). The CD4 positive T cell clone 3F8 expresses CD25 and CD122 and proliferates and produces IFNγ in response to IL-2.

3F8 cells were contacted with supernatants from 293T cells transfected with hIL-2 muteins as follows: Cells were grown in growth medium consisting of Yssel's medium (Iscove's modified Dulbecco's Medium (ThermoFisher), 0.25% w/v percent human albumin (Sigma), 1 percent penicillin/streptomycin (ThermoFisher), 1 percent ITS-X Insulin, Transferrin, Selenium (Gibco), 30 mg/L Transferrin (Roche), 2 mg/L Palmitic Acid (Sigma), 1 percent LA-OA-Albumin Linoleic Acid, Oleic Acid (Sigma), 1 percent human serum (Gemini) (Yssel et al (1984) J Immunol Methods 72: 219-227) at 0.2 million cells per ml with 50 Gy irradiated JY cells at 0.1 million cells per well and 40 Gy irradiated allogeneic PBMC at 1 million cells per mL. After six days of culture and expansion with human IL-2 at 100 pM, cells were washed and seeded into black, clear bottom 96 well plates (Costar) at 50 thousand cells per well in 75 μl growth medium. Five-fold serial dilutions of transfected 293T cell supernatants were made in growth medium and 75 μl of each dilution was added to plates of 3F8 cells in duplicate at final titrations ranging from 1:2 to 1:78125. Plates were transferred to a humidified incubator (ThermoFisher) and incubated at 37 degrees centigrade, 5 percent carbon dioxide for three days.

Plates were removed from the incubator and 40 μl of culture supernatant was harvested in to a 96 well flat bottom plate (Costar). Supernatants from duplicate wells were pooled. Cells were lysed by adding 100 μl per well of Celltiterglo (Promega) according to manufacturer's instructions. Cell lysates were mixed on an orbital shaker (VWR Scientific) for two minutes at 300 rpm then held at room temperature for 10 minutes. Luminescence for 3F8 cell lysates were read as counts per second on an Envision 2103 Multilabel Plate Reader (Perkin Elmer).

Production of IFNγ in the culture supernatants was measured using the MSD IFNγ V-Plex kit (MSD K151QOD) according to manufacturer's instructions. Briefly, mAb precoated MSD IFNγ assay plates were washed 3 times with 150 μL Tris Wash Buffer and IFNγ standards were diluted in Diluent 2. Culture supernatants were diluted 1:1 with Diluent 2 and 50 μL of samples and standards were added to the IFNγ assay plates and incubated for 120 min on an orbital shaker (VWR Scientific) at 300 rpm at room temperature. Plates were washed 3 times with Tris Wash Buffer and 25 μL 1× detection antibody in Diluent 3 was added to each well. Plates were incubated for 60 min on an orbital shaker (VWR Scientific) at 300 rpm at room temperature. Plates were washed 3 times with Tris Wash Buffer and 150 μL 2× Read Buffer T was added to each well and Luminescence signal was read on a Mesoscale Quickplex SQ120 instrument. Concentration of IFNγ in the supernatants were calculated based on the standard curve with MSD software.

To compare the effect of each hIL-2 mutein upon 3F8 cell proliferation and IFNγ production, CelltiterGlo values and IFNγ concentrations for cells treated with the supernatants were compared to those obtained for control cells treated with growth medium alone, wild-type IL-2 transfection, or supernatant from human REK IL-2 transfection. The data from these experiments is presented in Table 7 and FIGS. 3A-3D. These data demonstrate correlation between activity of the hIL-2 muteins to induce proliferation and IFNγ production.

TABLE 7

Proliferation and IFNγ Production by Human CD4 Positive T Cell Clone 3F8 InResponse to hIL2 Muteins

| Construct | Proliferation $IC_{50}$ (pM) | IFNγ Production $IC_{50}$ (pM) |
|---|---|---|
| IL-2 | 30.7 | 19.7 |
| REK | 14.2 | 17.7 |
| REE | 33.0 | 18.4 |
| REM | 32.6 | 12.7 |
| REV | 20.8 | 21.2 |
| REL | 68.4 | 33.8 |
| REF | 37.6 | 38.3 |
| REN | 13.7 | 15.7 |
| RER | 13.1 | 13.1 |
| REY | 19.3 | 22.1 |
| AEK | 13.7 | 19.0 |
| EEK | 36.0 | 58.7 |
| VEK | 15.5 | 4.6 |
| HEK | 20.9 | 30.4 |
| IEK | 10.0 | 8.8 |
| RTK | 62.8 | NA |

The invention claimed is:

1. A polypeptide having decreased binding affinity, compared to wild type hIL2, to the extracellular domain of hCD132, the polypeptide comprising an amino acid sequence of the formula (SEQ ID NO:97):

$(AA1)_a$-$(AA2)_b$-$(AA3)_c$-$(AA4)_d$-$(AA5)_e$-$(AA6)_f$-$(AA7)_g$-$(AA8)_h$-$(AA9)_i$-T10-Q11-L12-Q13-L14-E15-H16-L17-(AA18)-L19-D20-L21-(AA22)-M23-124-L25-N26-G27-128-N29-N30-Y31-K32-N33-P34-(AA35)-L36-T37-(AA38)-(AA39)-L40-T41-F42-K43-F44-Y45-M46-P47-K48-K49-A50-T51-E52-L53-K54-(AA55)-L56-Q57-C58-L59-E60-E61-E62-L63-K64-P65-L66-E67-E68-(AA69)-L70-N71-L72-A73-(AA74)-S75-K76-N77-F78-H79-(AA80-(AA81)-P82-R83-D84-(AA85)-(AA86)-S87-N88-(AA89)-N90-(AA91)-(AA92)-V93-L94-E95-L96-(AA97)-G98-S99-E100-T101-T102-F103-(AA104)-C105-E106-Y107-A108-(AA109)-E110-T111-A112-(AA113)-I114-V115-E116-F117-L118-N119-R120-W121-1122-T123-F124-(AA125)-(AA126)-S127-I128-I129-(AA130)-T131-L132-T133 wherein:

each of a, b, c, d, e, f, g, h, and i is individually selected from 0 or 1;

AA1 is A (wild type, a=1) or deleted (a=0);

AA2 is P (wild type, b=1) or deleted (b=0);

AA3 is T (wild type, c=1), C, A, G, Q, E, N, D, R, K, P, or deleted (c=0);

AA4 is S (wild type, d=1) or deleted (d=0);

AA5 is S (wild type, e=1) or deleted (e=0);

AA6 is S (wild type, f=1) or deleted (f=0);

AA7 is T (wild type, g=1) or deleted (g=0);

AA8 is K (wild type, h=1) or deleted (h=0);

AA9 is K (wild type, i=1) or deleted (i=0);

AA18 is R;

AA22 is T;

AA35 is K (wildtype) or E;

AA38 is R (wild type), W or G;

AA39 is M (wildtype), L or V;

AA55 is H (wildtype) or Y;

AA69 is V (wildtype) or A;

AA74 is Q (wild type), P, N, H, S;

AA80 is L (wild type), F or V;

AA81 is R (wild type), I, D or T;

AA85 is L (wild type) or V;

AA86 is I (wild type) or V;

AA89 is I (wild type) or V;

AA91 is V (wild type), R or K;

AA92 is I (wild type) or F;

AA97 is K (wild type) or Q;

AA104 is M (wild type) or A;

AA109 is D (wildtype), C or a non-natural amino acid with an activated side chain;

AA113 is T (wild type) or N;

AA125 is C (wild type), A or S;

AA126 is H; and

AA130 is S (wild type), T, G or R.

2. The polypeptide of claim 1 wherein a=0.

3. The polypeptide of claim 1, wherein the polypeptide is PEGylated.

4. The polypeptide of claim 1, wherein the polypeptide is PEGylated and the PEG component of such PEGylated polypeptide has a molecular weight of from about 10 kD to about 70 kD.

5. The polypeptide of claim 1, wherein the polypeptide is a fusion protein.

6. The polypeptide of claim 5 wherein the fusion protein comprises an Fc domain.

7. A nucleic acid encoding a polypeptide of claim 1.

8. The nucleic acid of claim 7 wherein the nucleic acid is DNA.

9. A recombinant expression vector comprising the nucleic acid of claim 7.

10. The vector of claim 9 wherein said vector is a viral vector.

11. The vector of claim 9 wherein said vector is a non-viral vector.

12. A host cell transformed with a vector of claim 9.

13. A pharmaceutical formulation comprising a polypeptide of claim 1.

14. The polypeptide of claim 1 wherein:

AA1 is A or deleted;

AA2 is P;

AA3 is T;

AA4 is S;

AA5 is S;

AA6 is S;

AA7 is T;

AA8 is K;

AA9 is K;

AA18 is R;

AA22 is T;

AA35 is K;

AA38 is R;

AA39 is M;

AA55 is H;

AA69 is V;

AA74 is Q;

AA80 is L;

AA81 is R;

AA85 is L;

AA86 is I;

AA89 is I;

AA91 is V;

AA92 is I;

AA97 is K;

AA104 is M;

AA109 is D;

AA113 is T;

AA125 is C;

AA126 is H; and

AA130 is S.

* * * * *

SEQUENCE LISTING

<160> NUMBER OF SEQ ID NOS: 101

<210> SEQ ID NO 1
<211> LENGTH: 251

<212> TYPE: PRT
<213> ORGANISM: Homo sapiens

<400> SEQUENCE: 1

Glu Leu Cys Asp Asp Asp Pro Pro Glu Ile Pro His Ala Thr Phe Lys
1 5 10 15

Ala Met Ala Tyr Lys Glu Gly Thr Met Leu Asn Cys Glu Cys Lys Arg
20 25 30

Gly Phe Arg Arg Ile Lys Ser Gly Ser Leu Tyr Met Leu Cys Thr Gly
35 40 45

Asn Ser Ser His Ser Ser Trp Asp Asn Gln Cys Gln Cys Thr Ser Ser
50 55 60

Ala Thr Arg Asn Thr Thr Lys Gln Val Thr Pro Gln Pro Glu Glu Gln
65 70 75 80

Lys Glu Arg Lys Thr Thr Glu Met Gln Ser Pro Met Gln Pro Val Asp
85 90 95

Gln Ala Ser Leu Pro Gly His Cys Arg Glu Pro Pro Pro Trp Glu Asn
100 105 110

Glu Ala Thr Glu Arg Ile Tyr His Phe Val Val Gly Gln Met Val Tyr
115 120 125

Tyr Gln Cys Val Gln Gly Tyr Arg Ala Leu His Arg Gly Pro Ala Glu
130 135 140

Ser Val Cys Lys Met Thr His Gly Lys Thr Arg Trp Thr Gln Pro Gln
145 150 155 160

Leu Ile Cys Thr Gly Glu Met Glu Thr Ser Gln Phe Pro Gly Glu Glu
165 170 175

Lys Pro Gln Ala Ser Pro Glu Gly Arg Pro Glu Ser Glu Thr Ser Cys
180 185 190

Leu Val Thr Thr Thr Asp Phe Gln Ile Gln Thr Glu Met Ala Ala Thr
195 200 205

Met Glu Thr Ser Ile Phe Thr Thr Glu Tyr Gln Val Ala Val Ala Gly
210 215 220

Cys Val Phe Leu Leu Ile Ser Val Leu Leu Leu Ser Gly Leu Thr Trp
225 230 235 240

Gln Arg Arg Gln Arg Lys Ser Arg Arg Thr Ile
245 250

<210> SEQ ID NO 2
<211> LENGTH: 525
<212> TYPE: PRT
<213> ORGANISM: Homo sapiens

<400> SEQUENCE: 2

Ala Val Asn Gly Thr Ser Gln Phe Thr Cys Phe Tyr Asn Ser Arg Ala
1 5 10 15

Asn Ile Ser Cys Val Trp Ser Gln Asp Gly Ala Leu Gln Asp Thr Ser
20 25 30

Cys Gln Val His Ala Trp Pro Asp Arg Arg Arg Trp Asn Gln Thr Cys
35 40 45

Glu Leu Leu Pro Val Ser Gln Ala Ser Trp Ala Cys Asn Leu Ile Leu
50 55 60

Gly Ala Pro Asp Ser Gln Lys Leu Thr Thr Val Asp Ile Val Thr Leu
65 70 75 80

Arg Val Leu Cys Arg Glu Gly Val Arg Trp Arg Val Met Ala Ile Gln
85 90 95

-continued

```
Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr Ile Pro Trp Leu Gly His Leu Leu Val Gly
    210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
        275                 280                 285

Pro Gly Gly Leu Ala Pro Glu Ile Ser Pro Leu Glu Val Leu Glu Arg
    290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
    370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Pro Glu
    450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
                485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu Val
```

-continued 515 520 525

<210> SEQ ID NO 3
<211> LENGTH: 214
<212> TYPE: PRT
<213> ORGANISM: Homo sapiens

<400> SEQUENCE: 3

Ala Val Asn Gly Thr Ser Gln Phe Thr Cys Phe Tyr Asn Ser Arg Ala
1 5 10 15

Asn Ile Ser Cys Val Trp Ser Gln Asp Gly Ala Leu Gln Asp Thr Ser
20 25 30

Cys Gln Val His Ala Trp Pro Asp Arg Arg Arg Trp Asn Gln Thr Cys
35 40 45

Glu Leu Leu Pro Val Ser Gln Ala Ser Trp Ala Cys Asn Leu Ile Leu
50 55 60

Gly Ala Pro Asp Ser Gln Lys Leu Thr Thr Val Asp Ile Val Thr Leu
65 70 75 80

Arg Val Leu Cys Arg Glu Gly Val Arg Trp Arg Val Met Ala Ile Gln
85 90 95

Asp Phe Lys Pro Phe Glu Asn Leu Arg Leu Met Ala Pro Ile Ser Leu
100 105 110

Gln Val Val His Val Glu Thr His Arg Cys Asn Ile Ser Trp Glu Ile
115 120 125

Ser Gln Ala Ser His Tyr Phe Glu Arg His Leu Glu Phe Glu Ala Arg
130 135 140

Thr Leu Ser Pro Gly His Thr Trp Glu Glu Ala Pro Leu Leu Thr Leu
145 150 155 160

Lys Gln Lys Gln Glu Trp Ile Cys Leu Glu Thr Leu Thr Pro Asp Thr
165 170 175

Gln Tyr Glu Phe Gln Val Arg Val Lys Pro Leu Gln Gly Glu Phe Thr
180 185 190

Thr Trp Ser Pro Trp Ser Gln Pro Leu Ala Phe Arg Thr Lys Pro Ala
195 200 205

Ala Leu Gly Lys Asp Thr
210

<210> SEQ ID NO 4
<211> LENGTH: 347
<212> TYPE: PRT
<213> ORGANISM: Homo sapiens

<400> SEQUENCE: 4

Leu Asn Thr Thr Ile Leu Thr Pro Asn Gly Asn Glu Asp Thr Thr Ala
1 5 10 15

Asp Phe Phe Leu Thr Thr Met Pro Thr Asp Ser Leu Ser Val Ser Thr
20 25 30

Leu Pro Leu Pro Glu Val Gln Cys Phe Val Phe Asn Val Glu Tyr Met
35 40 45

Asn Cys Thr Trp Asn Ser Ser Ser Glu Pro Gln Pro Thr Asn Leu Thr
50 55 60

Leu His Tyr Trp Tyr Lys Asn Ser Asp Asn Asp Lys Val Gln Lys Cys
65 70 75 80

Ser His Tyr Leu Phe Ser Glu Glu Ile Thr Ser Gly Cys Gln Leu Gln
85 90 95

Lys Lys Glu Ile His Leu Tyr Gln Thr Phe Val Val Gln Leu Gln Asp

```
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Val Val Ile Ser Val Gly Ser Met Gly Leu Ile Ile Ser Leu Leu Cys
                245                 250                 255

Val Tyr Phe Trp Leu Glu Arg Thr Met Pro Arg Ile Pro Thr Leu Lys
            260                 265                 270

Asn Leu Glu Asp Leu Val Thr Glu Tyr His Gly Asn Phe Ser Ala Trp
        275                 280                 285

Ser Gly Val Ser Lys Gly Leu Ala Glu Ser Leu Gln Pro Asp Tyr Ser
    290                 295                 300

Glu Arg Leu Cys Leu Val Ser Glu Ile Pro Pro Lys Gly Gly Ala Leu
305                 310                 315                 320

Gly Glu Gly Pro Gly Ala Ser Pro Cys Asn Gln His Ser Pro Tyr Trp
                325                 330                 335

Ala Pro Pro Cys Tyr Thr Leu Lys Pro Glu Thr
            340                 345


<210> SEQ ID NO 5
<211> LENGTH: 133
<212> TYPE: PRT
<213> ORGANISM: Homo sapiens

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125
```

-continued

Ile Ser Thr Leu Thr
    130

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ile Cys Leu Pro Arg Trp Gly Cys Leu Trp
1               5                   10

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatggattac cttttgtgag agcatcatct caaca 35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgttgagatg atgctctcac aaaaggtaat ccatc 35

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggattacctt ttgtatgagc atcatctcaa c 31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gttgagatga tgctcataca aaaggtaatc c 31

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggattacctt ttgtgtgagc atcatctcaa cac 33

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gtgttgagat gatgctcaca caaaaggtaa tcc 33

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggattacctt ttgtctgagc atcatctcaa cac 33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gtgttgagat gatgctcaga caaaaggtaa tcc 33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ggattacctt ttgtttcagc atcatctcaa cac 33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gtgttgagat gatgctgaaa caaaaggtaa tcc 33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 17

-continued

```
ggattacctt ttgtaacagc atcatctcaa cac                                33


<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

gtgttgagat gatgctgtta caaaaggtaa tcc                                33


<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

ggattacctt ttgtaggagc atcatctcaa cac                                33


<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

gtgttgagat gatgctccta caaaaggtaa tcc                                33


<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

ggattacctt ttgttacagc atcatctcaa cac                                33


<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

gtgttgagat gatgctgtaa caaaaggtaa tcc                                33


<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

ggattacctt ttgtaagagc atcatctc                                      28
```

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
gagatgatgc tcttacaaaa ggtaatcc 28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
ggattacctt ttgtaagagc atcatctc 28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
gagatgatgc tcttacaaaa ggtaatcc 28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
ggattacctt ttgtaagagc atcatctc 28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
gagatgatgc tcttacaaaa ggtaatcc 28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
ggattacctt ttgtaagagc atcatctc 28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gagatgatgc tcttacaaaa ggtaatcc 28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ggattacctt ttgtaagagc atcatctc 28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gagatgatgc tcttacaaaa ggtaatcc 28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
ggattacctt ttgtaagagc atcatctc 28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gagatgatgc tcttacaaaa ggtaatcc 28

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gatggattac cttttgtgag agcatcatct caaca 35

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
tgttgagatg atgctctcac aaaaggtaat ccatc 35

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ggattacctt ttgtatgagc atcatctcaa c 31

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gttgagatga tgctcataca aaaggtaatc c 31

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ggattacctt ttgtgtgagc atcatctcaa cac 33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gtgttgagat gatgctcaca caaaaggtaa tcc 33

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
ggattacctt ttgtctgagc atcatctcaa cac 33

<210> SEQ ID NO 42

<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
gtgttgagat gatgctcaga caaaaggtaa tcc 33

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
ggattacctt ttgtttcagc atcatctcaa cac 33

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
gtgttgagat gatgctgaaa caaaaggtaa tcc 33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
ggattacctt ttgtaacagc atcatctcaa cac 33

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
gtgttgagat gatgctgtta caaaaggtaa tcc 33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
ggattacctt ttgtaggagc atcatctcaa cac 33

<210> SEQ ID NO 48
<211> LENGTH: 33

<212> TYPE: DNA
<213> ORGANISM: Artificial Sequence
<220> FEATURE:
<223> OTHER INFORMATION: Description of Artificial Sequence: Synthetic primer

<400> SEQUENCE: 48
gtgttgagat gatgctccta caaaaggtaa tcc 33

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ggattacctt ttgttacagc atcatctcaa cac 33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gtgttgagat gatgctgtaa caaaaggtaa tcc 33

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gacttaatca gccgtatcaa cgtaata 27

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
tattacgttg atacggctga ttaagtc 27

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
ggacttaatc agcgatatca acgtaat 27

<210> SEQ ID NO 54
<211> LENGTH: 27
<212> TYPE: DNA

<213> ORGANISM: Artificial Sequence
<220> FEATURE:
<223> OTHER INFORMATION: Description of Artificial Sequence: Synthetic
primer

<400> SEQUENCE: 54
attacgttga tatcgctgat taagtcc 27

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
gggacttaat cagcggtatc aacgtaat 28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
attacgttga taccgctgat taagtccc 28

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
ggacttaatc agcattatca acgtaat 27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
attacgttga taatgctgat taagtcc 27

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
gcatttaagg ctgattttag agatgatttt g 31

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
caaaatcatc tctaaaatca gccttaaatg c 31

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
gagcatttaa ggctgcattt agagatg 27

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
catctctaaa tgcagcctta aatgctc 27

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
gcatttaagg ctgactttag agatgatttt g 31

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
caaaatcatc tctaaagtca gccttaaatg c 31

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
gcatttaagg ctgggtttag agatga 26

<210> SEQ ID NO 66
<211> LENGTH: 26
<212> TYPE: DNA
<213> ORGANISM: Artificial Sequence
<220> FEATURE:

<223> OTHER INFORMATION: Description of Artificial Sequence: Synthetic primer

<400> SEQUENCE: 66
tcatctctaa acccagcctt aaatgc 26

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
gcatttaagg ctggctttag agatgatttt g 31

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
caaaatcatc tctaaagcca gccttaaatg c 31

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
cagcaatatc aacaagatag ttctggaac 29

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
gttccagaac tatcttgttg atattgctg 29

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
cagcaatatc aacaagatag ttctggaac 29

<210> SEQ ID NO 72
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
gttccagaac tatcttgttg atattgctg 29

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
cagcaatatc aacaagatag ttctggaac 29

<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
gttccagaac tatcttgttg atattgctg 29

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
cagcaatatc aacaagatag ttctggaac 29

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
gttccagaac tatcttgttg atattgctg 29

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
cagcaatatc aacaagatag ttctggaac 29

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
gttccagaac tatcttgttg atattgctg 29

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 79
cagcaatatc aacaagatag ttctggaac 29

<210> SEQ ID NO 80
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
gttccagaac tatcttgttg atattgctg 29

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
cagcaatatc aacaagatag ttctggaac 29

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
gttccagaac tatcttgttg atattgctg 29

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
ggattacctt ttgtaagagc atcatctc 28

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
gagatgatgc tcttacaaaa ggtaatcc 28

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
ggattacctt ttgtaagagc atcatctc 28

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
gagatgatgc tcttacaaaa ggtaatcc 28

<210> SEQ ID NO 87
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
ggattacctt ttgtaagagc atcatctc 28

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
gagatgatgc tcttacaaaa ggtaatcc 28

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
ggattacctt ttgtaagagc atcatctc 28

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
gagatgatgc tcttacaaaa ggtaatcc 28

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
ggattacctt ttgtaagagc atcatctc 28

<210> SEQ ID NO 92
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
gagatgatgc tcttacaaaa ggtaatcc 28

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
ggattacctt ttgtaagagc atcatctc 28

<210> SEQ ID NO 94
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
gagatgatgc tcttacaaaa ggtaatcc 28

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
gacttaatca gccgtatcaa cgtaata 27

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 96

-continued

```
tattacgttg atacggctga ttaagtc                                          27


<210> SEQ ID NO 97
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A or absent
<220> FEATURE:
<221> NAME/KEY: MOD_RES
<222> LOCATION: (2)..(2)
<223> OTHER INFORMATION: P or absent
<220> FEATURE:
<221> NAME/KEY: MOD_RES
<222> LOCATION: (3)..(3)
<223> OTHER INFORMATION: T, C, A, G, Q, E, N, D, R, K, P, or absent
<220> FEATURE:
<221> NAME/KEY: MOD_RES
<222> LOCATION: (4)..(4)
<223> OTHER INFORMATION: S or absent
<220> FEATURE:
<221> NAME/KEY: MOD_RES
<222> LOCATION: (5)..(5)
<223> OTHER INFORMATION: S or absent
<220> FEATURE:
<221> NAME/KEY: MOD_RES
<222> LOCATION: (6)..(6)
<223> OTHER INFORMATION: S or absent
<220> FEATURE:
<221> NAME/KEY: MOD_RES
<222> LOCATION: (7)..(7)
<223> OTHER INFORMATION: T or absent
<220> FEATURE:
<221> NAME/KEY: MOD_RES
<222> LOCATION: (8)..(8)
<223> OTHER INFORMATION: K or absent
<220> FEATURE:
<221> NAME/KEY: MOD_RES
<222> LOCATION: (9)..(9)
<223> OTHER INFORMATION: K or absent
<220> FEATURE:
<221> NAME/KEY: MOD_RES
<222> LOCATION: (18)..(18)
<223> OTHER INFORMATION: L, R, G, M, F, E, H, W, K, Q, S, V, I, Y, H, D,
      or T
<220> FEATURE:
<221> NAME/KEY: MOD_RES
<222> LOCATION: (22)..(22)
<223> OTHER INFORMATION: Q, F, E, G, A, L, M, F, W, K, S, V, I, Y, H, R,
      N, D, T, or F
<220> FEATURE:
<221> NAME/KEY: MOD_RES
<222> LOCATION: (35)..(35)
<223> OTHER INFORMATION: K or E
<220> FEATURE:
<221> NAME/KEY: MOD_RES
<222> LOCATION: (38)..(38)
<223> OTHER INFORMATION: R, W, or G
<220> FEATURE:
<221> NAME/KEY: MOD_RES
<222> LOCATION: (39)..(39)
<223> OTHER INFORMATION: M, L, or V
<220> FEATURE:
<221> NAME/KEY: MOD_RES
<222> LOCATION: (55)..(55)
<223> OTHER INFORMATION: H or Y
<220> FEATURE:
<221> NAME/KEY: MOD_RES
<222> LOCATION: (69)..(69)
<223> OTHER INFORMATION: V or A
<220> FEATURE:
<221> NAME/KEY: MOD_RES
<222> LOCATION: (74)..(74)
```

<223> OTHER INFORMATION: Q, P, N, H, or S
<220> FEATURE:
<221> NAME/KEY: MOD_RES
<222> LOCATION: (80)..(80)
<223> OTHER INFORMATION: L, F, or V
<220> FEATURE:
<221> NAME/KEY: MOD_RES
<222> LOCATION: (81)..(81)
<223> OTHER INFORMATION: R, I, D, or T
<220> FEATURE:
<221> NAME/KEY: MOD_RES
<222> LOCATION: (85)..(85)
<223> OTHER INFORMATION: L or V
<220> FEATURE:
<221> NAME/KEY: MOD_RES
<222> LOCATION: (86)..(86)
<223> OTHER INFORMATION: I or V
<220> FEATURE:
<221> NAME/KEY: MOD_RES
<222> LOCATION: (89)..(89)
<223> OTHER INFORMATION: I or V
<220> FEATURE:
<221> NAME/KEY: MOD_RES
<222> LOCATION: (91)..(91)
<223> OTHER INFORMATION: V, R, or K
<220> FEATURE:
<221> NAME/KEY: MOD_RES
<222> LOCATION: (92)..(92)
<223> OTHER INFORMATION: I or F
<220> FEATURE:
<221> NAME/KEY: MOD_RES
<222> LOCATION: (97)..(97)
<223> OTHER INFORMATION: K or Q
<220> FEATURE:
<221> NAME/KEY: MOD_RES
<222> LOCATION: (104)..(104)
<223> OTHER INFORMATION: M or A
<220> FEATURE:
<221> NAME/KEY: MOD_RES
<222> LOCATION: (109)..(109)
<223> OTHER INFORMATION: D, C, or a non-natural amino acid with an activated side chain
<220> FEATURE:
<221> NAME/KEY: MOD_RES
<222> LOCATION: (113)..(113)
<223> OTHER INFORMATION: T or N
<220> FEATURE:
<221> NAME/KEY: MOD_RES
<222> LOCATION: (125)..(125)
<223> OTHER INFORMATION: C, A, or S
<220> FEATURE:
<221> NAME/KEY: MOD_RES
<222> LOCATION: (126)..(126)
<223> OTHER INFORMATION: Q, H, M, K, C, D, E, G, I, R, S, or T
<220> FEATURE:
<221> NAME/KEY: MOD_RES
<222> LOCATION: (130)..(130)
<223> OTHER INFORMATION: S, T, G, or R

<400> SEQUENCE: 97

```
Xaa Xaa Xaa Xaa Xaa Xaa Xaa Xaa Xaa Thr Gln Leu Gln Leu Glu His
1               5                   10                  15

Leu Xaa Leu Asp Leu Xaa Met Ile Leu Asn Gly Ile Asn Asn Tyr Lys
            20                  25                  30

Asn Pro Xaa Leu Thr Xaa Xaa Leu Thr Phe Lys Phe Tyr Met Pro Lys
        35                  40                  45

Lys Ala Thr Glu Leu Lys Xaa Leu Gln Cys Leu Glu Glu Glu Leu Lys
    50                  55                  60

Pro Leu Glu Glu Xaa Leu Asn Leu Ala Xaa Ser Lys Asn Phe His Xaa
65                  70                  75                  80

Xaa Pro Arg Asp Xaa Xaa Ser Asn Xaa Asn Xaa Xaa Val Leu Glu Leu
                85                  90                  95
```

-continued

```
Xaa Gly Ser Glu Thr Thr Phe Xaa Cys Glu Tyr Ala Xaa Glu Thr Ala
            100                 105                 110

Xaa Ile Val Glu Phe Leu Asn Arg Trp Ile Thr Phe Xaa Xaa Ser Ile
        115                 120                 125

Ile Xaa Thr Leu Thr
    130


<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 98

His His His His His His
1               5


<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 99

His His His His His His
1               5


<210> SEQ ID NO 100
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

tatagtcagc gccacccatg tacaggatgc aactcctgtc                           40


<210> SEQ ID NO 101
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

tatagggccc tatcaagtca gtgttgagat g                                    31
```